US012595255B2

(12) United States Patent
Lerner et al.

(10) Patent No.: US 12,595,255 B2
(45) Date of Patent: Apr. 7, 2026

(54) HETEROARYL-SUBSTITUTED IMIDAZOLE DERIVATIVES

(71) Applicant: Hoffmann-La Roche Inc., Little Falls, NJ (US)

(72) Inventors: Christian Lerner, Bottmingen (CH); Mingming Li, Shanghai (CN); Yongqiang Liu, Shanghai (CN); Jianhua Wang, Shanghai (CN); Min Wang, Shanghai (CN); Yongguang Wang, Shanghai (CN); Song Yang, Shanghai (CN); Chengang Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 437 days.

(21) Appl. No.: 18/228,924

(22) Filed: Aug. 1, 2023

(65) Prior Publication Data

US 2023/0373978 A1 Nov. 23, 2023

Related U.S. Application Data

(63) Continuation of application No. PCT/EP2022/052812, filed on Feb. 7, 2022.

(30) Foreign Application Priority Data

Feb. 7, 2021 (WO) ................ PCT/CN2021/075825

(51) Int. Cl.

| | |
|---|---|
| ***C07D 403/14*** | (2006.01) |
| ***A61P 31/04*** | (2006.01) |
| ***C07D 401/04*** | (2006.01) |
| ***C07D 401/14*** | (2006.01) |

(52) U.S. Cl.

CPC ............ *C07D 403/14* (2013.01); *A61P 31/04* (2018.01); *C07D 401/04* (2013.01); *C07D 401/14* (2013.01)

(58) Field of Classification Search

CPC .. C07D 403/14; C07D 401/04; C07D 401/14; A61P 31/04

See application file for complete search history.

(56) References Cited

U.S. PATENT DOCUMENTS

| | | | | |
|---|---|---|---|---|
| 2020/0290998 A1* | 9/2020 | Blanc | .................. | C07D 413/14 |
| 2023/0234930 A1* | 7/2023 | Cox | ..................... | C07D 249/08 |
| 2023/0295123 A1* | 9/2023 | Lerner | ................. | C07D 403/14 514/406 |

FOREIGN PATENT DOCUMENTS

| | | |
|---|---|---|
| WO | 2020/126954 A1 | 6/2020 |
| WO | 2020/182648 A1 | 9/2020 |
| WO | 2021/148420 A1 | 7/2021 |

OTHER PUBLICATIONS

International Preliminary Report on Patentability—PCT/EP2022/052812 issued Aug. 3, 2023, pp. 1-7.

International Search Report with Written Opinion—PCT/EP2022/052812 mailed May 3, 2022, pp. 1-11.

* cited by examiner

*Primary Examiner* — Timothy R Rozof

(74) *Attorney, Agent, or Firm* — Genentech, Inc.

(57) ABSTRACT

The invention provides novel heteroaryl-substituted imidazole derivatives having the general formula (I), and pharmaceutically acceptable salts thereof, wherein A and $R^1$ to $R^6$ are as described herein:

(I)

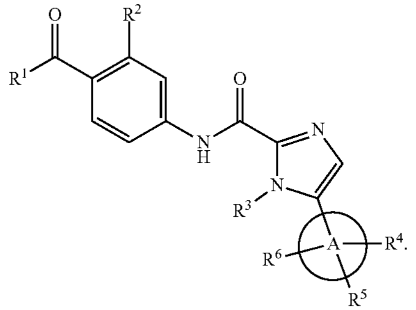

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

25 Claims, No Drawings

HETEROARYL-SUBSTITUTED IMIDAZOLE DERIVATIVES

CROSS-REFERENCE TO RELATED APPLICATIONS

This application is a Continuation of International Patent Application No. PCT/EP2022/052812, filed on Feb. 7, 2022, which claims benefit of priority to International Patent Application No. PCT/CN2021/075825, filed on Feb. 7, 2021, each of which is incorporated herein by reference in its entirety.

BACKGROUND

The present invention relates to novel heteroaryl-substituted imidazole derivatives which exhibit antibacterial properties. The invention also relates to methods of using the compounds for the treatment or prevention of bacterial infections and resulting diseases, in particular for the treatment or prevention of infections with *Acinetobacter baumannii* and resulting diseases.

*Acinetobacter baumannii* is a Gram-negative, aerobic, nonfermenting bacterium recognized over the last decades as an emergining pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistance that allows its survival and spread in the nosocomial setting, making this organism a frequent cause of outbreaks of infection and an endemic, health care-associated pathogen.

Due to increasing antibiotic resistance to most if not all available therapeutic options, Muti-Drug Resistant (MDR) *A. baumanniii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

The present invention provides novel compounds which exhibit activity against drug-susceptible as well as drug-resistant strains of *Acinetobacter baumannii*.

SUMMARY OF THE DISCLOSURE

In a first aspect, the present invention provides novel heteroaryl-substituted imidazole derivatives of formula (I):

(I)

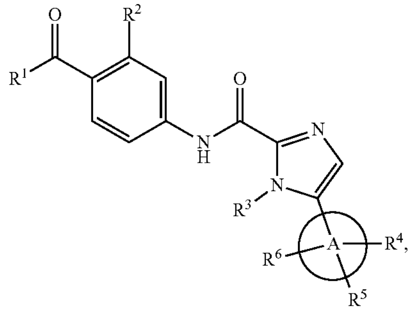

or pharmaceutically acceptable salts thereof, wherein A and $R^1$ to $R^6$ are as described herein.

In one aspect, the present invention provides a process for manufacturing the compounds of formula (I) as described herein, or pharmaceutically acceptable salts thereof, wherein said process is as described in any one of Schemes 1-4 disclosed herein.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use as antibiotic.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The following definitions are provided to facilitate understanding of certain terms used frequently herein and are not meant to limit the scope of the present disclosure. All references referred to herein are incorporated by reference in their entirety.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms, more preferably of 3 to 6 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and spiro[2.3]hexan-5-yl. A particularly preferred, yet non-limiting example of cycloalkyl includes cyclobutyl.

The term "aminoalkyl" refers to an alkyl group, wherein at least one of the hydrogen atoms of the alkyl group has been replaced by an amino group. Preferably, "aminoalkyl" refers to an alkyl group wherein 1, 2 or 3 hydrogen atoms of the alkyl group have been replaced by an amino group. Preferred, yet non-limiting examples of aminoalkyl are aminomethyl and 1-aminoethyl.

The term "aminoalkoxy" refers to an alkoxy group, wherein at least one of the hydrogen atoms of the alkoxy group has been replaced by an amino group. Preferably, "aminoalkoxy" refers to an alkoxy group wherein 1, 2 or 3 hydrogen atoms of the alkoxy group have been replaced by an amino group. Preferred, yet non-limiting examples of aminoalkoxy are aminomethoxy and 1-aminoethoxy.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. A preferred, yet non-limiting example of alkoxyalkyl is 2-ethoxyethyl.

The term "aminoalkoxyalkyl" refers to an alkyl group, wherein at least one of the hydrogen atoms of the alkyl group has been replaced by an aminoalkoxy group. Preferably, "aminoalkoxyalkyl" refers to an alkyl group wherein 1, 2 or 3 hydrogen atoms of the alkyl group have been replaced by an aminoalkoxy group. A preferred, yet non-limiting example of aminoalkoxyalkyl is 2-(2-aminoethoxy)ethyl.

The term "heterocyclyl" or "heterocycloalkyl" refers to a saturated or partly unsaturated mono- or bicyclic, preferably monocyclic ring system of 3 to 14 ring atoms, preferably 3 to 10 ring atoms, more preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, 1-piperidinyl, 2-piperidinyl, 3-piperidinyl, 4-piperidinyl, morpholino, morpholin-2-yl, morpholin-3-yl, pyrrolidinyl (e.g., pyrrolidin-3-yl), piperazinyl (e.g., piperazin-1-yl), 3-azabicyclo[3.1.0]hexan-6-yl, or 2,5-diazabicyclo[2.2.1]heptan-2-yl. Particularly preferred, yet non-limiting examples of heterocyclyl include piperidyl, piperazinyl, pyrrolidinyl and 3-azabicyclo[3.1.0]hexan-6-yl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 6-10 membered heteroaryl comprising 1 to 2 heteroatoms independently selected from O and N. Some non-limiting examples of heteroaryl include 2-pyridyl, 3-pyridyl, 4-pyridyl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, imidazol-1-yl, 1H-imidazol-2-yl, 1H-imidazol-4-yl, 1H-imidazol-5-yl, oxazol-2-yl, oxazol-4-yl, oxazol-5-yl, thiazol-4-yl, 1,2,4-oxadiazol-3-yl, pyrimidin-2-yl, pyrimidin-4-yl, pyrimidin-5-yl, and 2,3-dihydro-1,4-benzodioxinyl. Preferably, "heteroaryl" refers to pyridyl, indolyl, indazolyl, pyrimidinyl or 2,3-dihydro-1,4-benzodioxinyl. Most preferably, "heteroaryl" refers to pyridyl, indolyl, and indazolyl.

The term "hydroxy" refers to an —OH group.

The term "amino" refers to an —$NH_2$ group.

The term "cyano" refers to a —CN (nitrile) group.

The term "carbonyl" refers to a carbon radical having two of the four covalent bonds shared with an oxygen atom (C═O).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl, trifluoroethyl, 2-fluoroethyl, and 2,2-difluoroethyl, especially trifluoromethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are difluoromethoxy and trifluoromethoxy.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and 3-hydroxy-3-methyl-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as formic acid, acetic acid, 2,2,2-trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are formates and 2,2,2-trifluoroacetates.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds of the Invention

In a first aspect, the present invention provides a compound of formula (I):

(I)

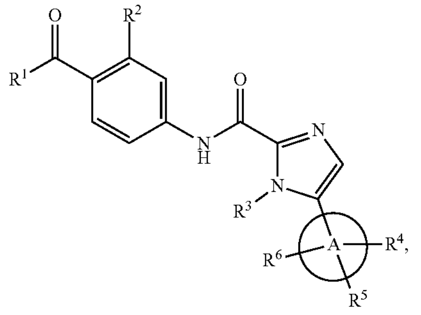

or a pharmaceutically acceptable salt thereof, wherein:

$R^1$ is selected from:

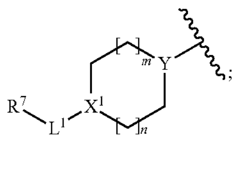

(i) a group

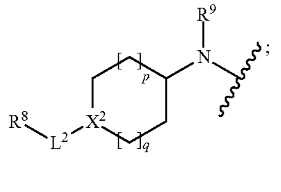

and (iii) a group

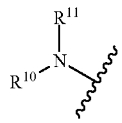

;

$R^2$ is selected from hydrogen, halogen, cyano, $C_1$-$C_6$-alkyl, $C_1$-$C_6$-alkoxy, halo-$C_1$-$C_6$-alkyl, and halo-$C_1$-$C_6$-alkoxy;

$R^3$ is selected from $C_1$-$C_6$-alkyl and halo-$C_1$-$C_6$-alkyl;

$R^4$, $R^5$, and $R^6$ are each independently selected from hydrogen, halogen, cyano, hydroxy, $C_1$-$C_6$-alkyl, $C_1$-$C_6$-alkoxy, halo-$C_1$-$C_6$-alkyl, halo-$C_1$-$C_6$-alkoxy, amino, $C_1$-$C_6$-alkyl-NH—, and $(C_1$-$C_6$-alkyl$)_2$N—;

$R^7$ is selected from hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, $(C_1$-$C_6$-alkyl$)_3N^+$—$C_1$-$C_6$-alkyl-, amino-$C_1$-$C_6$-alkoxy-$C_1$-$C_6$-alkyl, $C_1$-$C_6$-alkyl-NH—$C_1$-$C_6$-alkoxy-$C_1$-$C_6$-alkyl-, $(C_1$-$C_6$-alkyl$)_2$N—$C_1$-$C_6$-alkoxy-$C_1$-$C_6$-alkyl-, $(C_1$-$C_6$-alkyl$)_3N^+$—$C_1$-$C_6$-alkoxy-$C_1$-$C_6$-alkyl, and a group

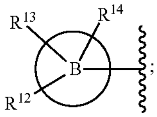

;

$R^8$ is selected from hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, $(C_1$-$C_6$-alkyl$)_3N^+$—$C_1$-$C_6$-alkyl-, amino-$C_1$-$C_6$-alkoxy-$C_1$-$C_6$-alkyl, $C_1$-$C_6$-alkyl-NH—$C_1$-$C_6$-alkoxy-$C_1$-$C_6$-alkyl-, $(C_1$-$C_6$-alkyl$)_2$N—$C_1$-$C_6$-alkoxy-$C_1$-$C_6$-alkyl-, $(C_1$-$C_6$-alkyl$)_3N^+$—$C_1$-$C_6$-alkoxy-$C_1$-$C_6$-alkyl, and a group

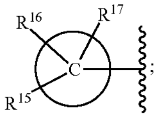

;

$R^9$ and $R^{11}$ are each independently selected from hydrogen and $C_1$-$C_6$-alkyl;

$R^{10}$ is selected from hydrogen, $C_1$-$C_6$-alkyl, hydroxy-$C_1$-$C_6$-alkyl, amino-$C_1$-$C_6$-alkyl-, $C_1$-$C_6$-alkyl-NH—$C_1$-$C_6$-alkyl-, $(C_1$-$C_6$-alkyl$)_2$N—$C_1$-$C_6$-alkyl-, and $(C_1$-$C_6$-alkyl$)_3N^+$—$C_1$-$C_6$-alkyl-;

$R^{12}$, $R^{13}$, $R^{14}$, $R^{15}$, $R^{16}$, and $R^{17}$ are each independently selected from hydrogen, halogen, cyano, hydroxy, amino, $C_1$-$C_6$-alkyl, $C_1$-$C_6$-alkoxy, halo-$C_1$-$C_6$-alkyl, halo-$C_1$-$C_6$-alkoxy, hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, and $(C_1$-$C_6$-alkyl$)_3N^+$—$C_1$-$C_6$-alkyl-;

A is a 5- to 14-membered heteroaryl;

B and C are are each independently selected from 3- to 14-membered heterocycloalkyl, and $C_3$-$C_{10}$-cycloalkyl;

$X^1$, $X^2$, and Y are each independently selected from N and CH;

m, n, p, and q are each independently 0 or 1; and $L^1$ and $L^2$ are each independently selected from carbonyl, —C(O)—$C_1$-$C_6$-alkyl-, —$C_1$-$C_6$-alkyl-C(O)—, —NH—C(O)—, and —C(O)—NH—;

provided that A is not pyrazole.

In one embodiment, the present invention provides a compound of formula (I) as described herein, or a pharmaceutically acceptable salt thereof, wherein $R^1$ is a group

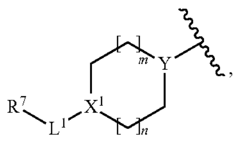

, wherein $R^7$, $L^1$, $X^1$, Y, m, and n are as described herein.

In one embodiment, the present invention provides a compound of formula (I) as described herein, or a pharmaceutically acceptable salt thereof, wherein $R^1$ is a group

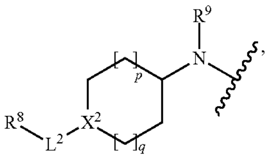

, wherein $R^8$, $R^9$, $L^2$, $X^2$, p, and q are as described herein.

In one embodiment, the present invention provides a compound of formula (I) as described herein, or a pharmaceutically acceptable salt thereof, wherein $R^1$ is a group

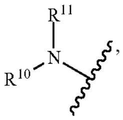

, wherein $R^{10}$ and $R^{11}$ are as described herein.

In one embodiment, the present invention provides a compound of formula (I) as described herein, or a pharmaceutically acceptable salt thereof, wherein:

$R^1$ is selected from:

(i) a group

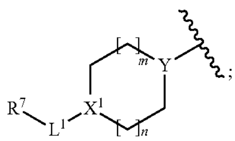

;

(ii) a group

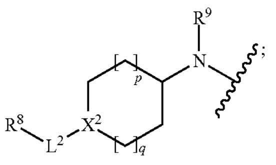

and (iii) a group

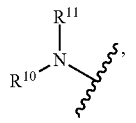

$R^7$ is selected from $(C_1\text{-}C_6\text{-alkyl})_2N—C_1\text{-}C_6\text{-alkyl-}$, $(C_1\text{-}C_6\text{-alkyl})_3N^+—C_1\text{-}C_6\text{-alkyl-}$, and a group

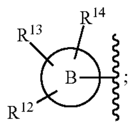

$R^8$ is selected from $(C_1\text{-}C_6\text{-alkyl})_2N—C_1\text{-}C_6\text{-alkyl-}$, $(C_1\text{-}C_6\text{-alkyl})_3N^+—C_1\text{-}C_6\text{-alkyl-}$, $(C_1\text{-}C_6\text{-alkyl})_3N^+—C_1\text{-}C_6\text{-alkoxy-}C_1\text{-}C_6\text{-alkyl}$, and a group

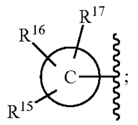

$R^9$ and $R^{11}$ are both hydrogen;

$R^{10}$ is selected from amino-$C_1$-$C_6$-alkyl and $(C_1\text{-}C_6\text{-alkyl})_3N^+—C_1\text{-}C_6\text{-alkyl-}$;

$R^{12}$ is selected from hydrogen, hydroxy, amino-$C_1$-$C_6$-alkyl, and $(C_1\text{-}C_6\text{-alkyl})_3N^+—C_1\text{-}C_6\text{-alkyl-}$;

$R^{13}$, $R^{14}$, $R^{16}$, and $R^{17}$ are each independently selected from hydrogen and $C_1$-$C_6$-alkyl;

$R^{15}$ is hydroxy;

B is selected from 3- to 14-membered heterocycloalkyl and $C_3$-$C_{10}$-cycloalkyl;

C is 3- to 14-membered heterocycloalkyl;

$L^1$ is selected from carbonyl, —$C_1$-$C_6$-alkyl-C(O)—, —NH—C(O)—, and —C(O)—NH—;

$L^2$ is selected from carbonyl and —C(O)—NH—;

$X^1$ and $X^2$ are each independently selected from N and CH;

Y is N;

m and n are both 1; and p and q are both 0;

or p and q are both 1.

In a preferred embodiment, the present invention provides a compound of formula (I) as described herein, or a pharmaceutically acceptable salt thereof, wherein:

$R^1$ is a group

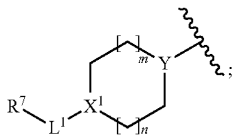

$R^7$ is a group

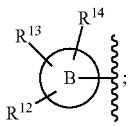

$R^{12}$ is hydrogen or hydroxy;

$R^{13}$ and $R^{14}$ are both hydrogen;

B is a 3- to 14-membered heterocycloalkyl;

$L^1$ is carbonyl or —$C_1$-$C_6$-alkyl-C(O)—;

$X^1$ and Y are both N; and m and n are both 1.

In a particularly preferred embodiment, the present invention provides a compound of formula (I) as described herein, or a pharmaceutically acceptable salt thereof, wherein:

$R^1$ is a group

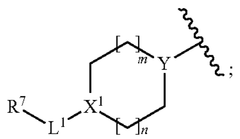

$R^7$ is a group

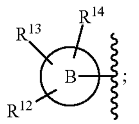

$R^{12}$ is hydrogen or hydroxy;

$R^{13}$ and $R^{14}$ are both hydrogen;

B is piperidine or pyrrolidine;

$L^1$ is carbonyl or —$CH_2$—C(O)—;

$X^1$ and Y are both N; and m and n are both 1.

In one embodiment, the present invention provides a compound of formula (I) as described herein, or a pharmaceutically acceptable salt thereof, wherein $R^7$ is selected from $(C_1\text{-}C_6\text{-alkyl})_2N—C_1\text{-}C_6\text{-alkyl-}$, $(C_1\text{-}C_6\text{-alkyl})_3N^+—C_1\text{-}C_6\text{-alkyl-}$, and a group

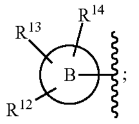

wherein $R^{12}$, $R^{13}$, and $R^{14}$ are as defined herein.

In a preferred embodiment, the present invention provides a compound of formula (I) as described herein, or a pharmaceutically acceptable salt thereof, wherein $R^7$ is a group

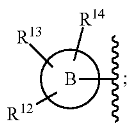

wherein $R^{12}$, $R^{13}$, and $R^{14}$ are as defined herein.

In a preferred embodiment, the present invention provides a compound of formula (I) as described herein, or a pharmaceutically acceptable salt thereof, wherein $R^8$ is selected from $(C_1\text{-}C_6\text{-alkyl})_2N—C_1\text{-}C_6\text{-alkyl-}$, $(C_1\text{-}C_6\text{-alkyl})_3N^+—C_1\text{-}C_6\text{-alkyl-}$, $(C_1\text{-}C_6\text{-alkyl})_3N^+—C_1\text{-}C_6\text{-alkoxy-}C_1\text{-}C_6\text{-alkyl}$, and a group

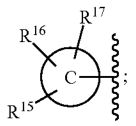

wherein $R^{15}$, $R^{16}$, and $R^{17}$ are as defined herein.

In a preferred embodiment, the present invention provides a compound of formula (I) as described herein, or a pharmaceutically acceptable salt thereof, wherein $R^9$ is hydrogen.

In a preferred embodiment, the present invention provides a compound of formula (I) as described herein, or a pharmaceutically acceptable salt thereof, wherein $R^{10}$ is selected from amino-$C_1$-$C_6$-alkyl and $(C_1\text{-}C_6\text{-alkyl})_3N^+—C_1\text{-}C_6\text{-alkyl-}$.

In a preferred embodiment, the present invention provides a compound of formula (I) as described herein, or a pharmaceutically acceptable salt thereof, wherein $R^{11}$ is hydrogen.

In one embodiment, the present invention provides a compound of formula (I) as described herein, or a pharmaceutically acceptable salt thereof, wherein $R^{12}$ is selected from hydrogen, hydroxy, amino-$C_1$-$C_6$-alkyl, and $(C_1\text{-}C_6\text{-alkyl})_3N^+—C_1\text{-}C_6\text{-alkyl-}$.

In a preferred embodiment, the present invention provides a compound of formula (I) as described herein, or a pharmaceutically acceptable salt thereof, wherein $R^{12}$ is hydrogen or hydroxy.

In one embodiment, the present invention provides a compound of formula (I) as described herein, or a pharmaceutically acceptable salt thereof, wherein $R^{13}$ is selected from hydrogen and $C_1$-$C_6$-alkyl.

In a preferred embodiment, the present invention provides a compound of formula (I) as described herein, or a pharmaceutically acceptable salt thereof, wherein $R^{13}$ is hydrogen.

In one embodiment, the present invention provides a compound of formula (I) as described herein, or a pharmaceutically acceptable salt thereof, wherein $R^{14}$ is selected from hydrogen and $C_1$-$C_6$-alkyl.

In a preferred embodiment, the present invention provides a compound of formula (I) as described herein, or a pharmaceutically acceptable salt thereof, wherein $R^{14}$ is hydrogen.

In a preferred embodiment, the present invention provides a compound of formula (I) as described herein, or a pharmaceutically acceptable salt thereof, wherein $R^{15}$ is hydroxy.

In a preferred embodiment, the present invention provides a compound of formula (I) as described herein, or a pharmaceutically acceptable salt thereof, wherein $R^{16}$ is selected from hydrogen and $C_1$-$C_6$-alkyl.

In a preferred embodiment, the present invention provides a compound of formula (I) as described herein, or a pharmaceutically acceptable salt thereof, wherein $R^{17}$ is selected from hydrogen and $C_1$-$C_6$-alkyl.

In a preferred embodiment, the present invention provides a compound of formula (I) as described herein, or a pharmaceutically acceptable salt thereof, wherein m and n are both 1.

In a preferred embodiment, the present invention provides a compound of formula (I) as described herein, or a pharmaceutically acceptable salt thereof, wherein p and q are both 0 or p and q are both 1

In one embodiment, the present invention provides a compound of formula (I) as described herein, or a pharmaceutically acceptable salt thereof, wherein $X^1$ is selected from N and CH.

In a preferred embodiment, the present invention provides a compound of formula (I) as described herein, or a pharmaceutically acceptable salt thereof, wherein $X^1$ is N.

In a preferred embodiment, the present invention provides a compound of formula (I) as described herein, or a pharmaceutically acceptable salt thereof, wherein $X^2$ is selected from N and CH.

In a preferred embodiment, the present invention provides a compound of formula (I) as described herein, or a pharmaceutically acceptable salt thereof, wherein Y is N.

In one embodiment, the present invention provides a compound of formula (I) as described herein, or a pharmaceutically acceptable salt thereof, wherein B is selected from 3- to 14-membered heterocycloalkyl and $C_3$-$C_{10}$-cycloalkyl.

In a preferred embodiment, the present invention provides a compound of formula (I) as described herein, or a pharmaceutically acceptable salt thereof, wherein B is a 14-membered heterocycloalkyl.

In a particularly preferred embodiment, the present invention provides a compound of formula (I) as described herein, or a pharmaceutically acceptable salt thereof, wherein B is piperidine or pyrrolidine.

In a preferred embodiment, the present invention provides a compound of formula (I) as described herein, or a pharmaceutically acceptable salt thereof, wherein C is a 3- to 14-membered heterocycloalkyl.

In one embodiment, the present invention provides a compound of formula (I) as described herein, or a pharmaceutically acceptable salt thereof, wherein $L^1$ is selected from carbonyl, $—C_1\text{-}C_6\text{-alkyl-}C(O)—$, $—NH—C(O)—$, and $—C(O)—NH—$.

In a preferred embodiment, the present invention provides a compound of formula (I) as described herein, or a pharmaceutically acceptable salt thereof, wherein $L^1$ is carbonyl or $—C_1\text{-}C_6\text{-alkyl-}C(O)—$.

In a particularly preferred embodiment, the present invention provides a compound of formula (I) as described herein, or a pharmaceutically acceptable salt thereof, wherein $L^1$ is carbonyl or $—CH_2—C(O)—$.

In a preferred embodiment, the present invention provides a compound of formula (I) as described herein, or a pharmaceutically acceptable salt thereof, wherein $L^2$ is selected from carbonyl and $—C(O)—NH—$.

In one embodiment, the present invention provides a compound of formula (I) as described herein, or a pharmaceutically acceptable salt thereof, wherein $R^2$ is halogen or $C_1$-$C_6$-alkyl.

In a preferred embodiment, the present invention provides a compound of formula (I) as described herein, or a pharmaceutically acceptable salt thereof, wherein $R^2$ is halogen.

In a particularly preferred embodiment, the present invention provides a compound of formula (I) as described herein, or a pharmaceutically acceptable salt thereof, wherein $R^2$ is chloro.

In one embodiment, the present invention provides a compound of formula (I) as described herein, or a pharmaceutically acceptable salt thereof, wherein $R^2$ is halogen or $C_1$-$C_6$-alkyl; and $R^3$ is $C_1$-$C_6$-alkyl.

In a preferred embodiment, the present invention provides a compound of formula (I) as described herein, or a pharmaceutically acceptable salt thereof, wherein $R^2$ is halogen; and $R^3$ is $C_1$-$C_6$-alkyl.

In a particularly preferred embodiment, the present invention provides a compound of formula (I) as described herein, or a pharmaceutically acceptable salt thereof, wherein $R^2$ is chloro; and $R^3$ is methyl.

In a preferred embodiment, the present invention provides a compound of formula (I) as described herein, or a pharmaceutically acceptable salt thereof, wherein $R^3$ is $C_1$-$C_6$-alkyl.

In a particularly preferred embodiment, the present invention provides a compound of formula (I) as described herein, or a pharmaceutically acceptable salt thereof, wherein $R^3$ is methyl.

In one embodiment, the present invention provides a compound of formula (I) as described herein, or a pharmaceutically acceptable salt thereof, wherein:

$R^4$ is selected from hydrogen, halogen, $C_1$-$C_6$-alkyl, $C_1$-$C_6$-alkoxy, $C_1$-$C_6$-alkyl-NH—, $(C_1$-$C_6$-alkyl$)_2$N—, and halo-$C_1$-$C_6$-alkyl;

$R^5$ is selected from hydrogen, $C_1$-$C_6$-alkyl, $C_1$-$C_6$-alkoxy, halogen, and $(C_1$-$C_6$-alkyl$)_2$N—; and $R^6$ is hydrogen or halogen.

In a preferred embodiment, the present invention provides a compound of formula (I) as described herein, or a pharmaceutically acceptable salt thereof, wherein:

$R^4$ is selected from halogen, $(C_1$-$C_6$-alkyl$)_2$N—, and halo-$C_1$-$C_6$-alkyl;

$R^5$ is selected from hydrogen, halogen, and $C_1$-$C_6$-alkoxy; and $R^6$ is hydrogen or halogen.

In a particularly preferred embodiment, the present invention provides a compound of formula (I) as described herein, or a pharmaceutically acceptable salt thereof, wherein:

$R^4$ is selected from fluoro, (methyl$)_2$N—, and $CF_3$;

$R^5$ is selected from hydrogen, fluoro, and methoxy; and $R^6$ is hydrogen or fluoro.

In one embodiment, the present invention provides a compound of formula (I) as described herein, or a pharmaceutically acceptable salt thereof, wherein $R^4$ is selected from hydrogen, halogen, $C_1$-$C_6$-alkyl, $C_1$-$C_6$-alkoxy, $C_1$-$C_6$-alkyl-NH—, $(C_1$-$C_6$-alkyl$)_2$N—, and halo-$C_1$-$C_6$-alkyl.

In a preferred embodiment, the present invention provides a compound of formula (I) as described herein, or a pharmaceutically acceptable salt thereof, wherein $R^4$ is selected from halogen, $(C_1$-$C_6$-alkyl$)_2$N—, and halo-$C_1$-$C_6$-alkyl.

In a particularly preferred embodiment, the present invention provides a compound of formula (I) as described herein, or a pharmaceutically acceptable salt thereof, wherein $R^4$ is selected from fluoro, (methyl$)_2$N—, and $CF_3$.

In one embodiment, the present invention provides a compound of formula (I) as described herein, or a pharmaceutically acceptable salt thereof, wherein $R^5$ is selected from hydrogen, $C_1$-$C_6$-alkyl, $C_1$-$C_6$-alkoxy, halogen, and $(C_1$-$C_6$-alkyl$)_2$N—.

In a preferred embodiment, the present invention provides a compound of formula (I) as described herein, or a pharmaceutically acceptable salt thereof, wherein $R^5$ is selected from hydrogen, halogen, and $C_1$-$C_6$-alkoxy.

In a particularly preferred embodiment, the present invention provides a compound of formula (I) as described herein, or a pharmaceutically acceptable salt thereof, wherein $R^5$ is selected from hydrogen, fluoro, and methoxy.

In a preferred embodiment, the present invention provides a compound of formula (I) as described herein, or a pharmaceutically acceptable salt thereof, wherein $R^6$ is hydrogen or halogen.

In a particularly preferred embodiment, the present invention provides a compound of formula (I) as described herein, or a pharmaceutically acceptable salt thereof, wherein $R^6$ is hydrogen or fluoro.

In one embodiment, the present invention provides a compound of formula (I) as described herein, or a pharmaceutically acceptable salt thereof, wherein A is a 6- to 14-membered heteroaryl.

In a preferred embodiment, the present invention provides a compound of formula (I) as described herein, or a pharmaceutically acceptable salt thereof, wherein A is a 6- to 9-membered heteroaryl.

In another preferred embodiment, the present invention provides a compound of formula (I) as described herein, or a pharmaceutically acceptable salt thereof, wherein A is selected from pyridyl, indolyl, indazolyl, pyrimidinyl, and 2,3-dihydro-1,4-benzodioxinyl.

In a particularly preferred embodiment, the present invention provides a compound of formula (I) as described herein, or a pharmaceutically acceptable salt thereof, wherein A is selected from pyridyl, indolyl, and indazolyl.

In one embodiment, the present invention provides a compound of formula (I) as described herein, or a pharmaceutically acceptable salt thereof, wherein:

A is a 6- to 9-membered heteroaryl;

$R^4$ is selected from hydrogen, halogen, $C_1$-$C_6$-alkyl, $C_1$-$C_6$-alkoxy, $C_1$-$C_6$-alkyl-NH—, $(C_1$-$C_6$-alkyl$)_2$N—, and halo-$C_1$-$C_6$-alkyl;

$R^5$ is selected from hydrogen, $C_1$-$C_6$-alkyl, $C_1$-$C_6$-alkoxy, halogen, and $(C_1$-$C_6$-alkyl$)_2$N—; and $R^6$ is hydrogen or halogen.

In a preferred embodiment, the present invention provides a compound of formula (I) as described herein, or a pharmaceutically acceptable salt thereof, wherein:

A is a 6- to 9-membered heteroaryl;

R is selected from halogen, $(C_1$-$C_6$-alkyl$)_2$N—, and halo-$C_1$-$C_6$-alkyl;

$R^5$ is selected from hydrogen, halogen, and $C_1$-$C_6$-alkoxy; and $R^6$ is hydrogen or halogen.

In a particularly preferred embodiment, the present invention provides a compound of formula (I) as described herein, or a pharmaceutically acceptable salt thereof, wherein:

A is selected from pyridyl, indolyl, and indazolyl;

$R^4$ is selected from fluoro, (methyl$)_2$N—, and $CF_3$;

$R^5$ is selected from hydrogen, fluoro, and methoxy; and $R^6$ is hydrogen or fluoro.

In one embodiment, the present invention provides a compound of formula (I) as described herein, or a pharmaceutically acceptable salt thereof, wherein:

$R^1$ is selected from:

(i) a group;

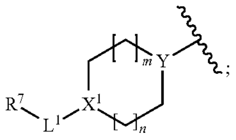

(ii) a group

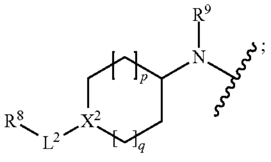

and (iii) a group

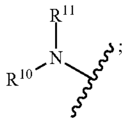

$R^2$ is halogen or $C_1$-$C_6$-alkyl;

$R^3$ is $C_1$-$C_6$-alkyl;

$R^4$ is selected from hydrogen, halogen, $C_1$-$C_6$-alkyl, $C_1$-$C_6$-alkoxy, $C_1$-$C_6$-alkyl-NH—, $(C_1$-$C_6$-alkyl$)_2$N—, and halo-$C_1$-$C_6$-alkyl;

$R^5$ is selected from hydrogen, $C_1$-$C_6$-alkyl, $C_1$-$C_6$-alkoxy, halogen, and $(C_1$-$C_6$-alkyl$)_2$N—;

$R^6$ is hydrogen or halogen $R^7$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, and a group

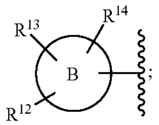

$R^1$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, $(C_1$-$C_6$-alkyl$)_3N^+$—$C_1$-$C_6$-alkoxy-$C_1$-$C_6$-alkyl, and a group

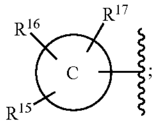

$R^9$ and $R^{11}$ are both hydrogen;

$R^{10}$ is selected from amino-$C_1$-$C_6$-alkyl and $(C_1$-$C_6$-alkyl$)_3N^+$—$C_1$-$C_6$-alkyl-;

$R^{12}$ is selected from hydrogen, hydroxy, amino-$C_1$-$C_6$-alkyl, and $(C_1$-$C_6$-alkyl$)_3N^+$—$C_1$-$C_6$-alkyl-;

$R^{13}$, $R^{14}$, $R^{16}$, and $R^{17}$ are each independently selected from hydrogen and $C_1$-$C_6$-alkyl;

$R^{15}$ is hydroxy;

A is a 6- to 9-membered heteroaryl;

B is selected from 3- to 14-membered heterocycloalkyl and $C_3$-$C_{10}$-cycloalkyl;

C is 3- to 14-membered heterocycloalkyl;

$L^1$ is selected from carbonyl, —$C_1$-$C_6$-alkyl-C(O)—, —NH—C(O)—, and —C(O)—NH—;

$L^2$ is selected from carbonyl and —C(O)—NH—;

$X^1$ and $X^2$ are each independently selected from N and CH;

Y is N;

m and n are both 1; and p and q are both 0;

or p and q are both 1.

In a preferred embodiment, the present invention provides a compound of formula (I) as described herein, or a pharmaceutically acceptable salt thereof, wherein:

$R^1$ is a group

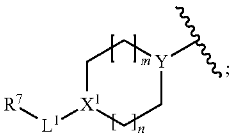

$R^2$ is halogen;

$R^3$ is $C_1$-$C_6$-alkyl;

$R^4$ is selected from halogen, $(C_1$-$C_6$-alkyl$)_2$N—, and halo-$C_1$-$C_6$-alkyl;

$R^5$ is selected from hydrogen, halogen, and $C_1$-$C_6$-alkoxy;

$R^6$ is hydrogen or halogen;

$R^7$ is a group

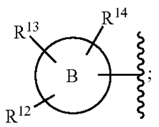

$R^{12}$ is hydrogen or hydroxy;

$R^{13}$ and $R^{14}$ are both hydrogen;

A is a 6- to 9-membered heteroaryl;

B is a 3- to 14-membered heterocycloalkyl;

$L^1$ is carbonyl or —$C_1$-$C_6$-alkyl-C(O)—;

$X^1$ and Y are both N; and m and n are both 1.

In a particularly preferred embodiment, the present invention provides a compound of formula (I) as described herein, or a pharmaceutically acceptable salt thereof, wherein:

$R^1$ is a group

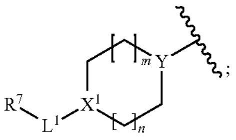

$R^2$ is chloro;

$R^3$ is methyl;

$R^4$ is selected from fluoro, (methyl$)_2$N—, and $CF_3$;

$R^5$ is selected from hydrogen, fluoro, and methoxy;

$R^6$ is hydrogen or fluoro;

$R^7$ is a group

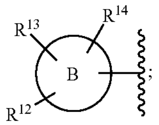

$R^{12}$ is hydrogen or hydroxy;

$R^{13}$ and $R^{14}$ are both hydrogen;

A is selected from pyridyl, indolyl, and indazolyl;

B is piperidine or pyrrolidine;

$L^1$ is carbonyl or $—CH_2—C(O)—$;

$X^1$ and Y are both N; and m and n are both 1.

In one embodiment, the present invention provides a compound of formula (I) as described herein, or a pharmaceutically acceptable salt thereof, wherein said compound of formula (I) is selected from:

Example A1

N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide;

Example A2

N-[3-chloro-4-[4-[2-[(3S)-pyrrolidin-3-yl]acetyl]piperazine-1-carbonyl]phenyl]-5-(6-fluoro-3-methyl-1H-indazol-5-yl)-1-methyl-imidazole-2-carboxamide;

Example A3

N-[3-chloro-4-[4-[2-[(3S)-pyrrolidin-3-yl]acetyl]piperazine-1-carbonyl]phenyl]-1-methyl-5-[3-(trifluoromethyl)-1H-indazol-5-yl]imidazole-2-carboxamide;

Example A4

N-[3-chloro-4-[4-[2-[(3S)-pyrrolidin-3-yl]acetyl]piperazine-1-carbonyl]phenyl]-5-(7-methoxy-1H-indol-4-yl)-1-methyl-imidazole-2-carboxamide;

Example A5

N-[3-chloro-4-[4-(piperidine-4-carbonyl)piperazine-1-carbonyl]phenyl]-5-(2,6-dichloro-3-pyridyl)-1-methyl-imidazole-2-carboxamide;

Example A6

N-[3-chloro-4-[4-(piperidine-4-carbonyl)piperazine-1-carbonyl]phenyl]-5-[6-(dimethylamino)-2-(trifluoromethyl)-3-pyridyl]-1-methyl-imidazole-2-carboxamide;

Example A7

N-[3-chloro-4-[4-(piperidine-4-carbonyl)piperazine-1-carbonyl]phenyl]-5-(2,6-dimethoxy-3-pyridyl)-1-methyl-imidazole-2-carboxamide;

Example A8

5-(5-chloro-2-methoxy-4-pyridyl)-N-[3-chloro-4-[4-(piperidine-4-carbonyl)piperazine-1-carbonyl]phenyl]-1-methyl-imidazole-2-carboxamide;

Example A9

N-[3-chloro-4-[4-[2-[(3S)-pyrrolidin-3-yl]acetyl]piperazine-1-carbonyl]phenyl]-5-[2-(dimethylamino)-4-(trifluoromethyl)pyrimidin-5-yl]-1-methyl-imidazole-2-carboxamide;

Example A10

N-[3-chloro-4-[4-(piperidine-4-carbonyl)piperazine-1-carbonyl]phenyl]-5-[2-methoxy-4-(trifluoromethyl)pyrimidin-5-yl]-1-methyl-imidazole-2-carboxamide;

Example A11

5-(5-chloro-1H-indol-4-yl)-N-[3-chloro-4-[4-[2-[(3S)-pyrrolidin-3-yl]acetyl]piperazine-1-carbonyl]phenyl]-1-methyl-imidazole-2-carboxamide;

Example A12

N-[3-chloro-4-[4-(piperidine-4-carbonyl)piperazine-1-carbonyl]phenyl]-5-(1H-indol-4-yl)-1-methyl-imidazole-2-carboxamide;

Example A13

N-[3-chloro-4-[4-(piperidine-4-carbonyl)piperazine-1-carbonyl]phenyl]-1-methyl-5-(1-methylindol-4-yl)imidazole-2-carboxamide;

Example A14

N-[3-chloro-4-[4-[2-[(3S)-pyrrolidin-3-yl]acetyl]piperazine-1-carbonyl]phenyl]-5-[6-methoxy-2-(trifluoromethyl)-3-pyridyl]-1-methyl-imidazole-2-carboxamide;

Example A15

5-(4-chloro-6-methoxy-3-pyridyl)-N-[3-chloro-4-[4-(piperidine-4-carbonyl)piperazine-1-carbonyl]phenyl]-1-methyl-imidazole-2-carboxamide;

Example A16

N-[3-chloro-4-[4-(piperidine-4-carbonyl)piperazine-1-carbonyl]phenyl]-5-[6-methoxy-2-(trifluoromethyl)-3-pyridyl]-1-methyl-imidazole-2-carboxamide;

Example A17

N-[3-chloro-4-[4-[(2S,4R)-4-hydroxypyrrolidine-2-carbonyl]piperazine-1-carbonyl]phenyl]-5-[6-methoxy-2-(trifluoromethyl)-3-pyridyl]-1-methyl-imidazole-2-carboxamide;

Example A18

N-[4-[4-[(1R,5S)-3-azabicyclo[3.1.0]hexane-6-carbonyl]piperazine-1-carbonyl]-3-chloro-phenyl]-5-[6-methoxy-2-(trifluoromethyl)-3-pyridyl]-1-methyl-imidazole-2-carboxamide;

Example A19

N-[3-chloro-4-[4-(piperidine-4-carbonyl)piperazine-1-carbonyl]phenyl]-5-[2-(difluoromethyl)-6-methoxy-3-pyridyl]-1-methyl-imidazole-2-carboxamide;

Example A20

N-[3-chloro-4-[4-(piperidine-4-carbonyl)piperazine-1-carbonyl]phenyl]-5-(2,3-dihydro-1,4-benzodioxin-6-yl)-1-methyl-imidazole-2-carboxamide;

Example B1

N-[4-(6-aminohexylcarbamoyl)-3-chloro-phenyl]-5-[6-(dimethylamino)-2,5-difluoro-3-pyridyl]-1-methyl-imidazole-2-carboxamide;

Example C1

N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide;

Example C2

N-[4-[4-[2-(dimethylamino)acetyl]piperazine-1-carbonyl]-3-methyl-phenyl]-5-[6-(dimethylamino)-2,5-difluoro-3-pyridyl]-1-methyl-imidazole-2-carboxamide;

Example C3

N-[3-chloro-4-[[3-[[2-(dimethylamino)acetyl]amino]cyclobutyl]carbamoyl]phenyl]-5-[6-(dimethylamino)-2,5-difluoro-3-pyridyl]-1-methyl-imidazole-2-carboxamide;

Example C4

N-[3-chloro-4-[4-[[2-(dimethylamino)acetyl]amino]piperidine-1-carbonyl]phenyl]-5-[6-(dimethylamino)-2,5-difluoro-3-pyridyl]-1-methyl-imidazole-2-carboxamide;

Example D1

[2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]-trimethyl-ammonium;

Example D2

[2-[4-[4-[[5-[6-(dimethylamino)-2,5-difluoro-3-pyridyl]-1-methyl-imidazole-2-carbonyl]amino]-2-methyl-benzoyl]piperazin-1-yl]-2-oxo-ethyl]-trimethyl-ammonium;

Example D3

6-[[2-chloro-4-[[5-[6-(dimethylamino)-2,5-difluoro-3-pyridyl]-1-methyl-imidazole-2-carbonyl]amino]benzoyl]amino]hexyl-trimethyl-ammonium;

Example D4

N-[3-chloro-4-[4-(1,1-dimethylpiperidin-1-ium-4-carbonyl)piperazine-1-carbonyl]phenyl]-5-[6-(dimethylamino)-2,5-difluoro-3-pyridyl]-1-methyl-imidazole-2-carboxamide;

Example D5

N-[3-chloro-4-[4-(1,1-dimethylpyrrolidin-1-ium-3-carbonyl)piperazine-1-carbonyl]phenyl]-5-[6-(dimethylamino)-2,5-difluoro-3-pyridyl]-1-methyl-imidazole-2-carboxamide;

Example D6

N-[3-chloro-4-[4-[(2S,4R)-4-hydroxy-1,1-dimethyl-pyrrolidin-1-ium-2-carbonyl]piperazine-1-carbonyl]phenyl]-5-[6-(dimethylamino)-2,5-difluoro-3-pyridyl]-1-methyl-imidazole-2-carboxamide;

Example D7

N-[3-chloro-4-[4-[2-(1,1-dimethylpiperidin-1-ium-4-yl)acetyl]piperazine-1-carbonyl]phenyl]-5-[6-(dimethylamino)-2,5-difluoro-3-pyridyl]-1-methyl-imidazole-2-carboxamide;

Example D8

[2-[[3-[[2-chloro-4-[[5-[6-(dimethylamino)-2,5-difluoro-3-pyridyl]-1-methyl-imidazole-2-carbonyl]amino]benzoyl]amino]cyclobutyl]amino]-2-oxo-ethyl]-trimethyl-ammonium;

Example D9

[2-[[1-[2-chloro-4-[[5-[6-(dimethylamino)-2,5-difluoro-3-pyridyl]-1-methyl-imidazole-2-carbonyl]amino]benzoyl]-4-piperidyl]amino]-2-oxo-ethyl]-trimethyl-ammonium;

Example D10

2-[3-[4-[[2-chloro-4-[[5-[6-(dimethylamino)-2,5-difluoro-3-pyridyl]-1-methyl-imidazole-2-carbonyl]amino]benzoyl]amino]-1-piperidyl]-3-oxo-propoxy]ethyl-trimethyl-ammonium;

Example D11

[3-[4-[2-chloro-4-[[5-[6-(dimethylamino)-2,5-difluoro-3-pyridyl]-1-methyl-imidazole-2-carbonyl]amino]benzoyl]piperazine-1-carbonyl]cyclobutyl]methyl-trimethyl-ammonium;

Example D12

N-[3-chloro-4-[[1-[(2S,4R)-4-hydroxy-1,1-dimethyl-pyrrolidin-1-ium-2-carbonyl]-4-piperidyl]carbamoyl]phenyl]-5-[6-(dimethylamino)-2,5-difluoro-3-pyridyl]-1-methyl-imidazole-2-carboxamide;

Example D13

1-[2-chloro-4-[[5-[6-(dimethylamino)-2,5-difluoro-3-pyridyl]-1-methyl-imidazole-2-carbonyl]amino]benzoyl]-N-(1,1-dimethylpyrrolidin-1-ium-3-yl)piperidine-4-carboxamide;

Example E1

N-[3-chloro-4-[4-(piperidine-4-carbonyl)piperazine-1-carbonyl]phenyl]-5-[2,5-difluoro-6-(methylamino)-3-pyridyl]-1-methyl-imidazole-2-carboxamide;

Example E2

N-[3-chloro-4-[4-(piperidine-4-carbonyl)piperazine-1-carbonyl]phenyl]-5-[6-(dimethylamino)-2,5-difluoro-3-pyridyl]-1-methyl-imidazole-2-carboxamide;

Example E3

N-[3-chloro-4-[4-(piperidine-4-carbonyl)piperazine-1-carbonyl]phenyl]-5-[6-(dimethylamino)-2-fluoro-3-pyridyl]-1-methyl-imidazole-2-carboxamide;

Example E4

N-[3-chloro-4-[4-(piperidine-4-carbonyl)piperazine-1-carbonyl]phenyl]-5-[6-(dimethylamino)-2-methyl-3-pyridyl]-1-methyl-imidazole-2-carboxamide;

Example E5

5-[2-chloro-6-(dimethylamino)-3-pyridyl]-N-[3-chloro-4-[4-(piperidine-4-carbonyl)piperazine-1-carbonyl]phenyl]-1-methyl-imidazole-2-carboxamide;

Example F1

N-[3-chloro-4-[4-(4-hydroxypiperidine-4-carbonyl)piperazine-1-carbonyl]phenyl]-5-[6-(dimethylamino)-2,5-difluoro-3-pyridyl]-1-methyl-imidazole-2-carboxamide;

Example F2

N-[3-chloro-4-[4-[2-[(3S)-pyrrolidin-3-yl]acetyl]piperazine-1-carbonyl]phenyl]-5-[6-(dimethylamino)-2,5-difluoro-3-pyridyl]-1-methyl-imidazole-2-carboxamide;

Example F3

N-[3-chloro-4-[4-[2-(4-hydroxy-4-piperidyl)acetyl]piperazine-1-carbonyl]phenyl]-5-[6-(dimethylamino)-2,5-difluoro-3-pyridyl]-1-methyl-imidazole-2-carboxamide;

Example F4

N-[3-chloro-4-[4-(pyrrolidine-3-carbonyl)piperazine-1-carbonyl]phenyl]-5-[6-(dimethylamino)-2,5-difluoro-3-pyridyl]-1-methyl-imidazole-2-carboxamide;

Example F5

N-[3-chloro-4-[4-[(2S,4R)-4-hydroxypyrrolidine-2-carbonyl]piperazine-1-carbonyl]phenyl]-5-[6-(dimethylamino)-2,5-difluoro-3-pyridyl]-1-methyl-imidazole-2-carboxamide;

Example F6

N-[3-chloro-4-[4-[2-(4-piperidyl)acetyl]piperazine-1-carbonyl]phenyl]-5-[6-(dimethylamino)-2,5-difluoro-3-pyridyl]-1-methyl-imidazole-2-carboxamide;

Example F7

N-[4-[4-[3-(aminomethyl)cyclobutanecarbonyl]piperazine-1-carbonyl]-3-chloro-phenyl]-5-[6-(dimethylamino)-2,5-difluoro-3-pyridyl]-1-methyl-imidazole-2-carboxamide;

Example F8

N-[4-[[1-[3-(2-aminoethoxy)propanoyl]-4-piperidyl]carbamoyl]-3-chloro-phenyl]-5-[6-(dimethylamino)-2,5-difluoro-3-pyridyl]-1-methyl-imidazole-2-carboxamide;

Example F9

N-[3-chloro-4-[[1-[(2S,4R)-4-hydroxypyrrolidine-2-carbonyl]-4-piperidyl]carbamoyl]phenyl]-5-[6-(dimethylamino)-2,5-difluoro-3-pyridyl]-1-methyl-imidazole-2-carboxamide; and Example F10

1-[2-chloro-4-[[5-[6-(dimethylamino)-2,5-difluoro-3-pyridyl]-1-methyl-imidazole-2-carbonyl]amino]benzoyl]-N-pyrrolidin-3-yl-piperidine-4-carboxamide.

In a preferred embodiment, the present invention provides a compound of formula (I) as described herein, or a pharmaceutically acceptable salt thereof, wherein said compound of formula (I) is selected from:

Example A1

N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide;

Example A3

N-[3-chloro-4-[4-[2-[(3S)-pyrrolidin-3-yl]acetyl]piperazine-1-carbonyl]phenyl]-1-methyl-5-[3-(trifluoromethyl)-1H-indazol-5-yl]imidazole-2-carboxamide;

Example A14

N-[3-chloro-4-[4-[2-[(3S)-pyrrolidin-3-yl]acetyl]piperazine-1-carbonyl]phenyl]-5-[6-methoxy-2-(trifluoromethyl)-3-pyridyl]-1-methyl-imidazole-2-carboxamide;

Example A17

N-[3-chloro-4-[4-[(2S,4R)-4-hydroxypyrrolidine-2-carbonyl]piperazine-1-carbonyl]phenyl]-5-[6-methoxy-2-(trifluoromethyl)-3-pyridyl]-1-methyl-imidazole-2-carboxamide;

Example E2

N-[3-chloro-4-[4-(piperidine-4-carbonyl)piperazine-1-carbonyl]phenyl]-5-[6-(dimethylamino)-2,5-difluoro-3-pyridyl]-1-methyl-imidazole-2-carboxamide; and Example F2

N-[3-chloro-4-[4-[2-[(3S)-pyrrolidin-3-yl]acetyl]piperazine-1-carbonyl]phenyl]-5-[6-(dimethylamino)-2,5-difluoro-3-pyridyl]-1-methyl-imidazole-2-carboxamide.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 3*rd Edition*, Richard C. Larock. John Wiley & Sons, New York, NY. 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Intermediates A can be prepared according to Scheme 1. Protecting the acid group of Nitrobenzoic acid A with PG group gives compound B. Reduction the nitro group to give amine compound C using iron/ammonium chloride. Coupling of C and 5-bromo-1-methyl-imidazole-2-carboxylic acid with a condensing agent, such as HATU/DIPEA in DMSO, affords Intermediate A.

Scheme 1

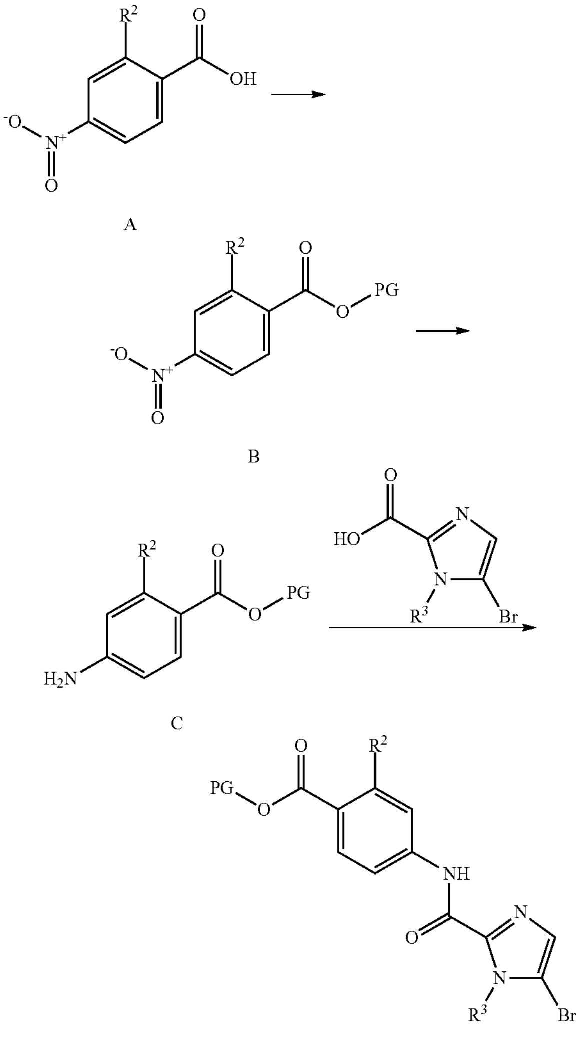

A

B

C

Intermediate A

In Scheme 1, PG denotes a suitable protective group, such as an alkyl group, e.g. Me, Et or iso-butyl, and $R^2$ and $R^3$ are as defined herein.

Intermediates D can be prepared according to Scheme 2. After deprotection of Intermediate A, the product D can couple with an amine in the presence of a condensing agent, such as HATU/DIPEA, in a solvent like DMSO, to afford Intermediate B with. Deprotection of Intermediate B affords Intermediate C which can be further coupled with a carboxylic acid in the presence of a condensing agent, such as HATU/DIPEA, in a solvent like DMSO to yield Intermediate D.

Scheme 2

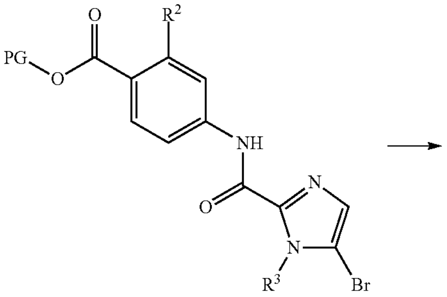

Intermediate A

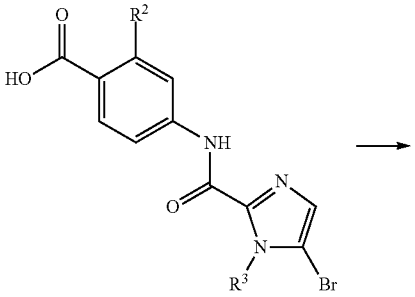

D

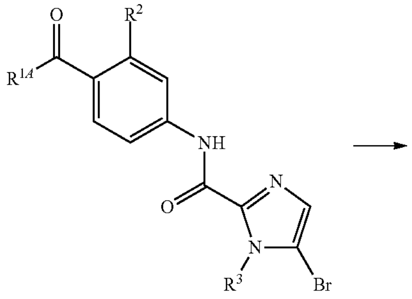

Intermediate B

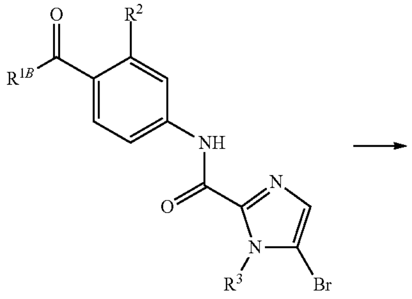

Intermediate C

-continued

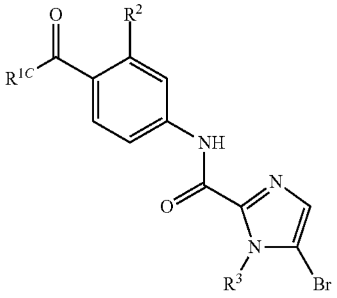

Intermediate D

In scheme 2, PG denotes a suitable protective group, such as an alkyl group, e.g. Me, Et or iso-butyl, and $R^2$ and $R^3$ are as defined herein. Furthermore:

$R^{1A}$ is selected from:

(i) a group

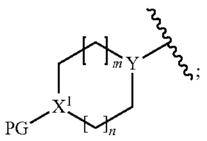

(ii) a group

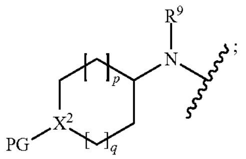

and (iii) a group

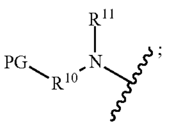

$R^{1B}$ is selected from:

(i) a group

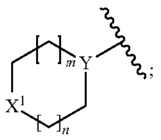

(ii) a group

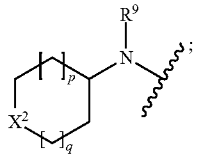

and (iii) a group

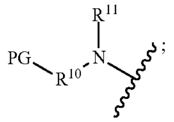

$R^{1C}$ is selected from:

(i) a group

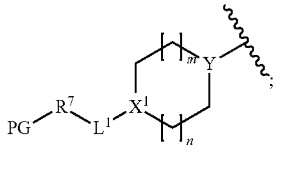

(ii) a group

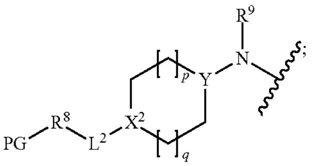

and (iii) a group

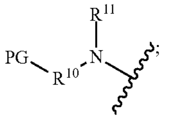

wherein $X^1$, $X^2$, Y, m, n, p, q, $L^1$, $L^2$, and $R^7$ to $R^{11}$ are as defined herein.

Examples A-E can be prepared according to Scheme 3. Suzuki coupling of Intermediate D with boronic acids or esters (Intermediates E or F) can be achieved using palladium catalysts and phosphine ligands to give Intermediates J or M. Further deprotection of Intermediates J or M affords Examples A-E. In some case, Examples A-E are further alkylated to afford quaternary ammonium salt analogues.

Scheme 3

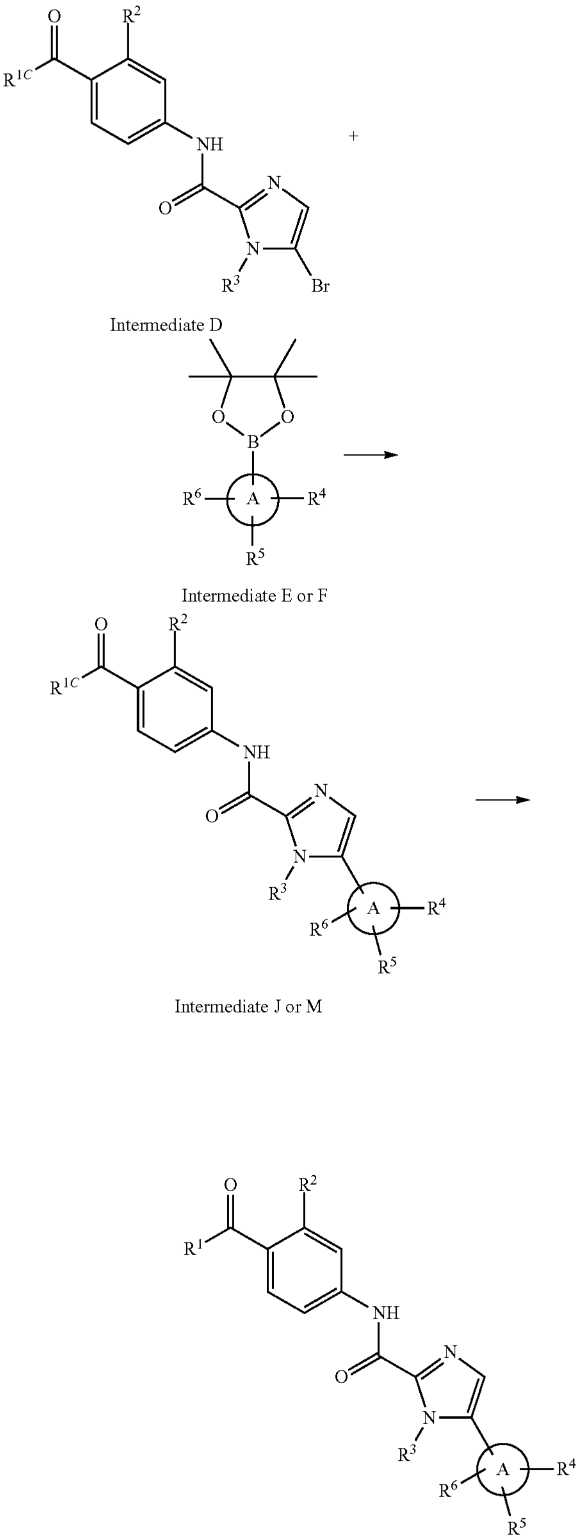

Intermediate D

Intermediate E or F

Intermediate J or M

Intermediate A-E

In Scheme 3, PG denotes a suitable protective group, such as an alkyl group, e.g. Me, Et or iso-butyl, and $R^1$ to $R^6$ and A are as defined herein. Furthermore:

$R^{1C}$ is selected from:

(i) a group

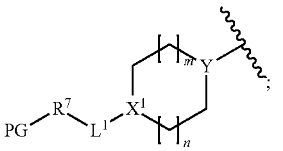

(ii) a group

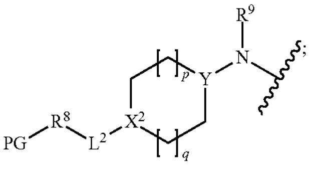

and (iii) a group

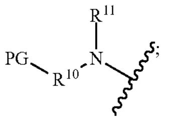

wherein $X^1$, $X^2$, Y, m, n, p, q, $L^1$, $L^2$, and $R^7$ to $R^{11}$ are as defined herein.

Examples A-E can also be prepared according to Scheme 4. Suzuki coupling of Intermediates A with bronic acids or esters (Intermediates E or F) can be achieved using palladium catalysts and phosphine ligands to give Intermediates O. After deprotection of Intermediates O to afford Intermediates H, coupling with amines in the presence of a condensing agent, such as HATU/DIPEA in DMSO, yields Intermediates G. Deprotection of Intermediates G affords Intermediates I, K or L (in some cases, this step can already afford Examples A-E). Intermediates I, K or L can further be coupled with an acid using a condensing agent, such as HATU/DIPEA in DMSO, to yield Intermediates J or M. Final deprotection of Intermediates J or M affords Examples A-E. In some case, Examples A-E are further alkylated to afford quaternary ammonium salt analogues.

Scheme 4

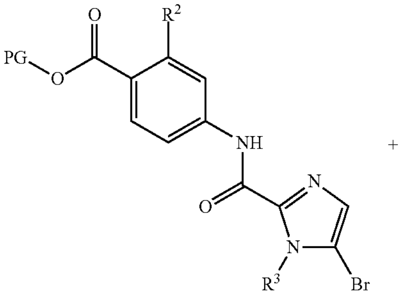

Intermediate A

-continued

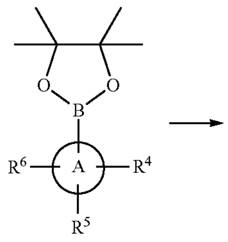

Intermediate E or F

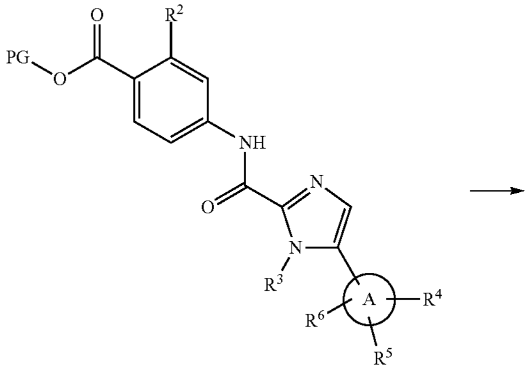

Intermediate O

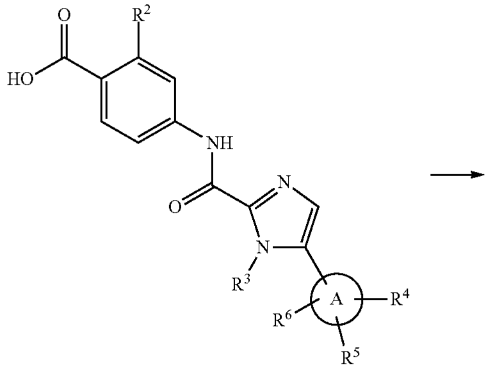

Intermediate H

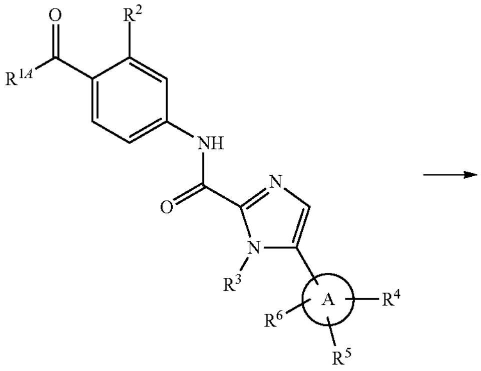

Intermediate G

-continued
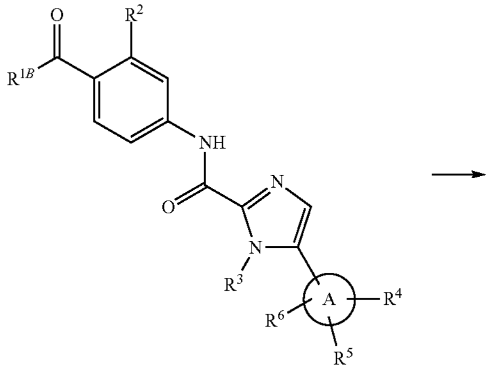
Intermediate I, K or L
Example A-E
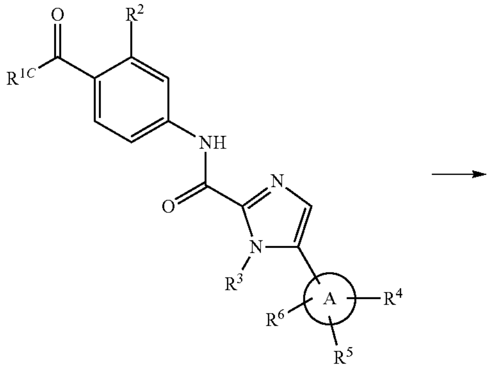
Intermediate J or M
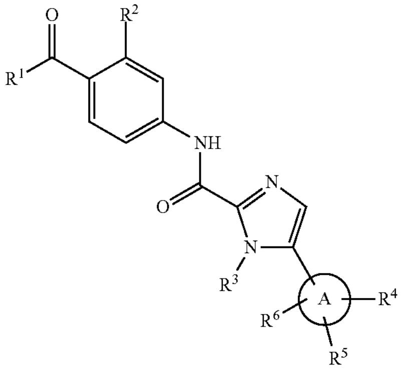
Example A-E
In Scheme 4, PG denotes a suitable protective group, such as an alkyl group, e.g. Me, Et or iso-butyl, and $R^1$ to $R^6$ and A are as defined herein. Furthermore:
$R^{1A}$ is selected from:
(i) a group
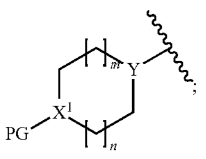
(ii) a group
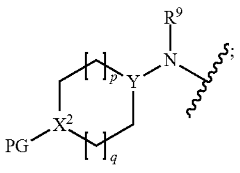
and
(iii) a group
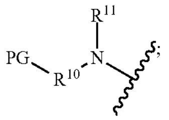
$R^{1B}$ is selected from:
(i) a group
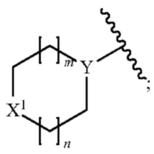
(ii) a group
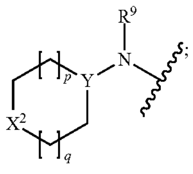
and
(iii) a group
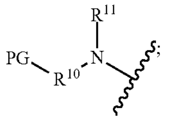
$R^{1C}$ is selected from:
(i) a group
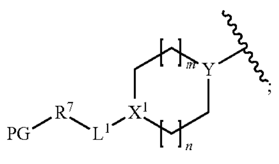

(ii) a group

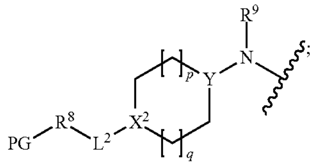

and (iii) a group

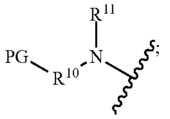

wherein $X^1$, $X^2$, Y, m, n, p, q, $L^1$, $L^2$, and $R^7$ to $R^1$ are as defined herein.

In one aspect, the present invention provides a process for manufacturing the compounds of formula (I) as described herein, or pharmaceutically acceptable salts thereof, wherein said process is as described in any one of Schemes 1-4 disclosed herein.

In a further aspect, the present invention provides a compound of formula (I) as described herein, or a pharmaceutically acceptable salt thereof, when manufactured according to the processes disclosed herein.

Using the Compounds of the Invention

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii.*

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii.*

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii.*

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In one aspect, the present invention provides compounds of formula (I) or their pharmaceutically acceptable salts as described herein for use as therapeutically active substances.

In a further aspect, the present invention provides compounds of formula (I) or their pharmaceutically acceptable salts as described herein, for use as antibiotics.

In a further aspect, the present invention provides the use of a compound of formula (I) as described herein, or a pharmaceutically acceptable salt thereof, as an antibiotic.

In a further aspect, the present invention provides a method for the treatment or prevention of nosocomial infections and resulting diseases, which method comprises administering a compound of formula (I) as described herein, or a pharmaceutically acceptable salt thereof, to a mammal.

In a particular embodiment, said nosocomial infections and resulting diseases are selected from bacteremia, pneumonia, meningitis, urinary tract infection and wound infection, or a combination thereof.

In a further aspect, the present invention provides a method for the treatment or prevention of infections and resulting diseases caused by Gram-negative bacteria, which method comprises administering a compound of formula (I) as described herein, or a pharmaceutically acceptable salt thereof, to a mammal.

In one embodiment, said Gram-negative bacteria are selected from *Klebsiella pneumoniae, Acinetobacter baumannii, Pseudomonas aeruginosa, Enterobacter* species and *E. coli.*

In a particular embodiment, said Gram-negative bacteria are *Acinetobacter baumannii.*

In one embodiment, said infections and resulting diseases caused by said Gram-negative bacteria are selected from bacteremia, pneumonia, meningitis, urinary tract infection and wound infection, or a combination thereof.

In a further aspect, the present invention provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof, which method comprises administering a compound of formula (I) as described herein, or a pharmaceutically acceptable salt thereof, to a mammal.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof, are selected from bacteremia, pneumonia, meningitis, urinary tract infection and wound infection, or a combination thereof.

In a further aspect, the present invention provides a method for the treatment or prevention of bacterial infections and resulting diseases, which method comprises administering a compound of formula (I) or a pharmaceutically acceptable salt thereof as defined above to a mammal.

In one embodiment, said bacterial infections and resulting diseases are selected from bacteremia, pneumonia, meningitis, urinary tract infection, and wound infection.

In one embodiment, said bacterial infections and resulting diseases are caused by by *Acinetobacter* species, most particularly by *Acinetobacter baumannii.*

In a further aspect, the present invention provides the use of a compound of formula (I) as described herein, or a pharmaceutically acceptable salt thereof, in a method described herein.

In a further aspect, the present invention provides a compound of formula (I) as described herein, or a pharmaceutically acceptable salt thereof, for use in a method described herein.

In a further aspect, the present invention provides the use of a compound of formula (I) as described herein, or a pharmaceutically acceptable salt thereof, for the preparation of medicaments useful for the methods described herein.

Pharmaceutical Compositions and Administration

In one aspect, the present invention provides pharmaceutical compositions comprising compounds of formula (I) or their pharmaceutically acceptable salts as defined above and one or more pharmaceutically acceptable excipients. Exemplary pharmaceutical compositions are described in Examples 1 to 4.

In a further aspect, the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including antibiotic agents. If the administration is not simultaneous, the compounds are administered in a close time proximity to each other. Furthermore, it does not matter if the compounds are administered in the same dosage form, e.g. one compound may be administered intravenously and another compound may be administered orally.

Typically, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, and Macrolides (erythromycin).

In one aspect, the present invention provides a pharmaceutical composition described herein, further comprising an additional therapeutic agent.

In one aspect, the present invention provides a pharmaceutical combination comprising a compound of formula (I) described herein and an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

The following abbreviations are used in the present text:

ACN or MeCN Acetonitrile

BINAP 2,2'-Bis(diphenylphosphino)-1,1'-binaphthalene

CFU colony-forming unit d day

DCM dichloromethane

DIPEA N,N-diisopropylethylamine

EtOAc or EA Ethyl acetate

FA Formic acid h(s) or hr(s) hour

HATU 1-[Bis(dimethylamino)methylene]-1H-1,2,3-triazolo[4,5-b]pyridinium 3-oxid hexafluorophosphate HPLC high performance liquid chromatography HPLC-UV high performance liquid chromatography with ultraviolet detector IC50 half maximal inhibitory concentration IC90 90% inhibitory concentration $NaBH_3CN$ Sodium cyanoborohydride PE petroleum ether $PdCl_2(DPPF)$ [1,1'-Bis(diphenylphosphino)ferrocene]dichloropalladium(II)

$Pd2(dba)_3$ Tris(dibenzylideneacetone)dipalladium(0)

PG Protective group

Precat precatalyst prep-HPLC preparative high performance liquid chromatography rt room temperature sat saturated SEM 2-methoxyethyl(trimethyl)silane FA Formic acid TEMPO (2,2,6,6-Tetramethylpiperidin-1-yl)oxyl TFA Trifluoroacetic Acid wt weight X-PHOS 2-Dicyclohexylphosphino-2',4',6'-triisopropylbiphenyl

Intermediate A1 tert-butyl 4-[(5-bromo-1-methyl-imidazole-2-carbonyl)amino]-2-chloro-benzoate

Step 1: tert-butyl 2-chloro-4-nitro-benzoate

To a mixture of 2-chloro-4-nitro-benzoic acid (15.0 g, 74.42 mmol), N,N-dimethylpyridin-4-amine (2.73 g, 22.33 mmol) and N,N-diethylethanamine (31.12 mL, 223.26 mmol) in THF (80 mL) was added a solution of tert-butoxycarbonyl tert-butyl carbonate (24.36 g, 111.63 mmol) in THF (20 mL) at −10° C. The resulting mixture was warmed to 25° C. and stirred for another 14 h. The mixture was concentrated. The residue was treated with EA (50 mL) and $H_2O$ (50 mL). The mixture was extracted with EA. The combined organic layers were concentrated. The crude was then purified by flash column chromatography to afford tert-butyl 2-chloro-4-nitro-benzoate (18.8 g) as a colorless solid.

Step 2: tert-butyl 4-amino-2-chloro-benzoate

To a mixture of tert-butyl 2-chloro-4-nitro-benzoate (18.8 g, 72.96 mmol) and Ammonium chloride (19.51 g, 364.81 mmol) in ethanol (200 mL) and water (200 mL) was added Iron (20.37 g, 364.81 mmol). The mixture was stirred at 25° C. for 14 h. The mixture was filtered by Celite. The filtrate was concentrated to remove ethanol. The mixture was extracted with EA. The combined organic layers were dried over anhydrous $Na_2SO_4$ and concentrated to afford tert-butyl 4-amino-2-chloro-benzoate (16.31 g) as a light yellow solid. MS $[M+H]^+$: 228.1.

Step 3: tert-butyl 4-[(5-bromo-1-methyl-imidazole-2-carbonyl)amino]-2-chloro-benzoate A mixture of 5-bromo-1-methyl-imidazole-2-carboxylic acid hydrochloride (7.0 g, 28.99 mmol), tert-butyl 4-amino-2-chloro-benzoate (6.0 g, 26.35 mmol), HATU (13.23 g, 34.79 mmol) and DIPEA (16.16 mL, 92.77 mmol) in DMF (15 mL) was stirred at 25° C. for 3 h. The mixture was added water (10 mL) and extracted with EA. The combined organic layers were concentrated. The crude was purified by FCC to afford tert-butyl 4-[(5-bromo-1-methyl-imidazole-2-carbonyl)amino]-2-chloro-benzoate (8 g, 19.29 mmol) as a white solid. MS $[M+H]^+$: 414.0.

The following Intermediates were prepared in analogy of Intermediate A1:

| Ex# | Name | Structure | MS ESI $[M + H]^+$ | Starting Material |
|---|---|---|---|---|
| Intermediate A2 | tert-butyl 4-[(5-bromo-1-methyl-imidazole-2-carbonyl)amino]-2-methyl-benzoate | 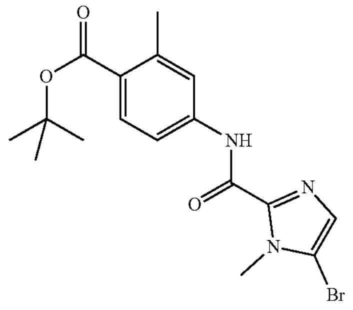 [SMILES: Cc1cc(NC(=O)c2ncc(Br)n2C)ccc1C(=O)OC(C)(C)C] | 394.2 | 2-methyl-4-nitro-benzoic acid and tert-butoxycarbonyl tert-butyl carbonate |

Intermediate B1 tert-butyl 4-[4-[(5-bromo-1-methyl-imidazole-2-carbonyl)amino]-2-chloro-benzoyl]piperazine-1-carboxylate Step 1: 4-[(5-bromo-1-methyl-imidazole-2-carbonyl)amino]-2-chloro-benzoic Acid In a 250 mL round-bottomed flask, a solution of tert-butyl 4-[(5-bromo-1-methyl-imidazole-2-carbonyl)amino]-2-chloro-benzoate (6.5 g, 15.67 mmol) in DCM (30 ml) and TFA (12 ml) was stirred at room temperature for 1 h. Then the clear solution was concentrated in vacuum to afford 4-[(5-bromo-1-methyl-imidazole-2-carbonyl)amino]-2-chloro-benzoic acid (5.5 g) as a light yellow solid. MS $[M+H]^+$: 357.9.

Step 2: tert-butyl 4-[4-[(5-bromo-1-methyl-imidazole-2-carbonyl)amino]-2-chloro-benzoyl]piperazine-1-carboxylate In a 100 mL round-bottomed flask, a mixture of 4-[(5-bromo-1-methyl-imidazole-2-carbonyl)amino]-2-chloro-benzoic acid (4.17 g, 11.64 mmol), tert-butyl piperazine-1-carboxylate (4.34 g, 23.3 mmol), HATU (6.64 g, 17.5 mmol) and DIPEA (4.51 g, 34.9 mmol) in DMF (30 mL) was stirred at room temperature for 16 h. Then the mixture was poured into water. The white solid was collected and dried in vacuum to afford tert-butyl 4-[4-[(5-bromo-1-methyl-imidazole-2-carbonyl)amino]-2-chloro-benzoyl]piperazine-1-carboxylate (5.9 g) as a yellow solid. MS $[M+H]^+$: 526.1.

The following Intermediates were prepared in analogy of Intermediate B1:

Intermediate C1

5-bromo-N-[3-chloro-4-(piperazine-1-carbonyl)phenyl]-1-methyl-imidazole-2-carboxamide A solution of tert-butyl 4-[4-[(5-bromo-1-methyl-imidazole-2-carbonyl)amino]-2-chloro-benzoyl]piperazine-1-carboxylate (5.9 g, 11.2 mmol) in DCM (20 ml) and TFA (15 ml) was stirred at room temperature for 30 min. Then the solution was concentrated and basified by $NH_3{\cdot}H_2O$. The water layer was extracted with DCM. The combined organic layers were dried over anhydrous $Na_2SO_4$ and concentrated in vacuum to afford 5-bromo-N-[3-chloro-4-(piperazine-1-carbonyl)phenyl]-1-methyl-imidazole-2-carboxamide (4.6 g) as a yellow solid. MS $[M+H]^+$: 426.0.

Intermediate D1 tert-butyl (3S)-3-[2-[4-[4-[(5-bromo-1-methyl-imidazole-2-carbonyl)amino]-2-chloro-benzoyl]piperazin-1-yl]-2-oxo-ethyl]pyrrolidine-1-carboxylate A mixture of 5-bromo-N-[3-chloro-4-(piperazine-1-carbonyl)phenyl]-1-methyl-imidazole-2-carboxamide (3 g, 7.03 mmol), 2-[(3S)-1-tert-butoxycarbonylpyrrolidin-3-yl]acetic acid (2.42 g, 10.55 mmol), HATU (4.01 g, 10.55 mmol) and DIPEA (2.73 g, 21.1 mmol) in DMF (15 ml) was stirred at room temperature for 16 h. The mixture was poured into water. The water layer was extracted with DCM. The combined organic layers were washed with water, dried over anhydrous $Na_2SO_4$ and concentrated in vacuum to afford tert-butyl (3S)-3-[2-[4-[4-[(5-bromo-1-methyl-imidazole-2-carbonyl)amino]-2-chloro-benzoyl]piperazin-1-yl]-2-oxo-ethyl]pyrrolidine-1-carboxylate (3.5 g). MS $[M+H]^+$: 636.9.

The following Intermediates were prepared in analogy of Intermediate D1:

| Ex# | Name | Structure | MS ESI $[M+H]^+$ | Starting Material |
|---|---|---|---|---|
| Intermediate B2 | tert-butyl 4-[4-[(5-bromo-1-methyl-imidazole-2-carbonyl)amino]-2-methyl-benzoyl]piperazine-1-carboxylate | 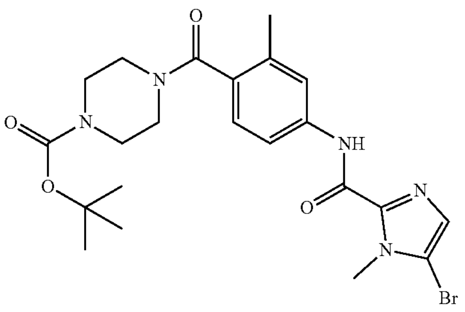 [SMILES: Cc1cc(NC(=O)c2ncc(Br)n2C)ccc1C(=O)N1CCN(C(=O)OC(C)(C)C)CC1] | 506.1 | Intermediate A2 |

| Ex# | Name | Structure | MS ESI $[M + H]^+$ | Starting Material |
|---|---|---|---|---|
| Intermediate D2 | tert-butyl 4-[4-[4-[(5-bromo-1-methyl-imidazole-2-carbonyl)amino]-2-chloro-benzoyl]piperazine-1-carbonyl]piperidine-1-carboxylate | 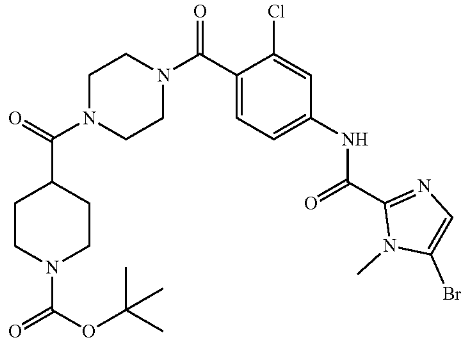 [SMILES: Cn1c(Br)cnc1C(=O)Nc1ccc(C(=O)N2CCN(C(=O)C3CCN(C(=O)OC(C)(C)C)CC3)CC2)c(Cl)c1] | 638.9 | Intermediate C1 and 1-tert-butoxycarbonyl-piperidine-4-carboxylic acid |
| Intermediate D3 | tert-butyl (2S,4R)-2-[4-[4-[(5-bromo-1-methyl-imidazole-2-carbonyl)amino]-2-chloro-benzoyl]piperazine-1-carbonyl]-4-hydroxy-pyrrolidine-1-carboxylate | 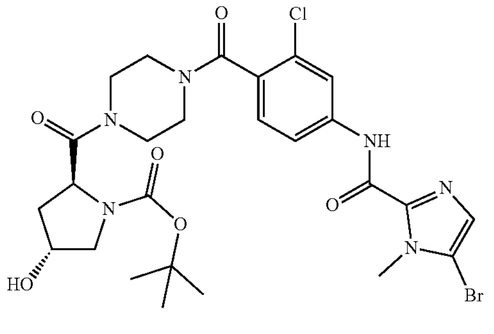 [SMILES: Cn1c(Br)cnc1C(=O)Nc1ccc(C(=O)N2CCN(C(=O)[C@@H]3C[C@@H](O)CN3C(=O)OC(C)(C)C)CC2)c(Cl)c1] | 639.2 | Intermediate C1 and (2S,4R)-1-(tert-butoxycarbonyl)-4-hydroxypyrrolidine-2-carboxylic acid |
| Intermediate D4 | tert-butyl (1S,5R)-6-[4-[4-[(5-bromo-1-methyl-imidazole-2-carbonyl)amino]-2-chloro-benzoyl]piperazine-1-carbonyl]-3-azabicyclo[3.1.0]hexane-3-carboxylate | 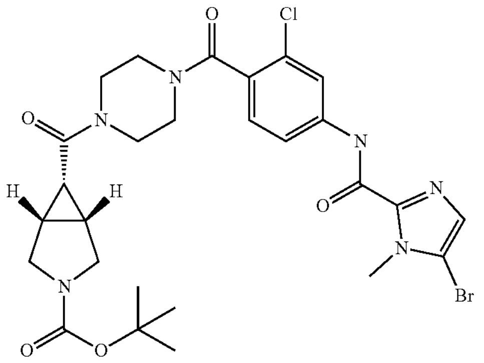 [SMILES: Cn1c(Br)cnc1C(=O)Nc1ccc(C(=O)N2CCN(C(=O)[C@@H]3[C@@H]4CN(C(=O)OC(C)(C)C)C[C@@H]43)CC2)c(Cl)c1] | 635.1 | Intermediate C1 and (1R,5S,6S)-3-(tert-butoxycarbonyl)-3-azabicyclo[3.1.0]hexane-6-carboxylic acid |

Intermediate E1 tert-butyl 5-fluoro-4-(4,4,5,5-tetramethyl-1,3,2-dioxaborolan-2-yl)indole-1-carboxylate At room temperature, a mixture of 5-fluoro-4-(4,4,5,5-tetramethyl-1,3,2-dioxaborolan-2-yl)-1H-indole (240 mg, 919 μmol), tert-butoxycarbonyl tert-butyl carbonate (301 mg, 1.38 mmol), DMAP (112 mg, 919 μmol) and $Et_3N$ (279 mg, 2.76 mmol) in DCM (10 ml) was stirred for 16 h. Then the mixture was washed with 1N HCl, $NaHCO_3$ aqueous solution and NaCl aqueous solution. Then the organic layer was dried over anhydrous $Na_2SO_4$ and concentrated in vacuum to afford tert-butyl 5-fluoro-4-(4,4,5,5-tetramethyl-1,3,2-dioxaborolan-2-yl)indole-1-carboxylate (300 mg).

The following Intermediates were prepared in analogy of Intermediate E1:

| Ex# | Name | Structure | MS ESI $[M + H]^+$ | Starting Material |
|---|---|---|---|---|
| Intermediate E2 | tert-butyl 6-fluoro-3-methyl-5-(4,4,5,5-tetramethyl-1,3,2-dioxaborolan-2-yl)indazole-1-carboxylate | 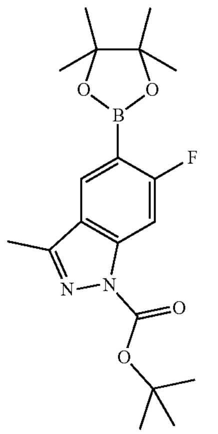 [SMILES: Cc1nn(C(=O)OC(C)(C)C)c2cc(F)c(B3OC(C)(C)C(C)(C)O3)cc12] | 377.1 | 6-fluoro-3-methyl-5-(4,4,5,5-tetramethyl-1,3,2-dioxaborolan-2-yl)-1H-indazole and tert-butoxycarbonyl tert-butyl carbonate |
| Intermediate E3 | tert-butyl 5-(4,4,5,5-tetramethyl-1,3,2-dioxaborolan-2-yl)-3-(trifluoromethyl)indazole-1-carboxylate | 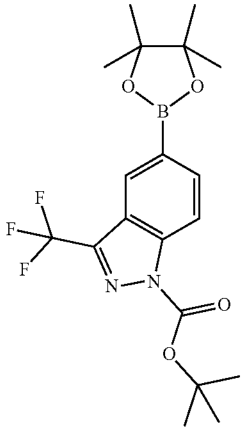 [SMILES: CC(C)(C)OC(=O)n1nc(C(F)(F)F)c2cc(B3OC(C)(C)C(C)(C)O3)ccc21] | 413.1 | 5-(4,4,5,5-tetramethyl-1,3,2-dioxaborolan-2-yl)-3-(trifluoromethyl)-1H-indazole and tert-butoxycarbonyl tert-butyl carbonate |

Intermediate E4 tert-butyl 7-methoxy-4-(4,4,5,5-tetramethyl-1,3,2-dioxaborolan-2-yl)indole-1-carboxylate

Step 1: tert-butyl 4-bromo-7-methoxy-indole-1-carboxylate

At room temperature, a mixture of 4-bromo-7-methoxy-1H-indole (1 g, 4.42 mmol), tert-butoxycarbonyl tert-butyl carbonate (1.16 g, 5.31 mmol), DMAP (54 mg, 442 μmol) and $Et_3N$ (895 mg, 1.23 ml, 8.85 mmol) in DCM (10 ml) was stirred for 16 h. Then the mixture was washed with water, dried over anhydrous $Na_2SO_4$ and concentrated in vacuum to afford the crude product. The residue was purified by flash column to afford tert-butyl 4-bromo-7-methoxy-indole-1-carboxylate (1.2 g) as a yellow oil. MS $[M+H]^+$: 325.4.

Step 2: tert-butyl 7-methoxy-4-(4,4,5,5-tetramethyl-1,3,2-dioxaborolan-2-yl)indole-1-carboxylate Under $N_2$ protection, a mixture of 4,4,5,5-tetramethyl-2-(4,4,5,5-tetramethyl-1,3,2-dioxaborolan-2-yl)-1,3,2-dioxaborolane (405 mg, 1.59 mmol), tert-butyl 4-bromo-7-methoxy-indole-1-carboxylate (400 mg, 1.23 mmol), potassium acetate (361 mg, 3.68 mmol) and 1,1-bis(diphenylphosphino)ferrocene-palladium(II)dichloride dichloromethane complex (100 mg, 123 μmol) in 1,4-Dioxane (20 ml) was stirred at 70° C. for 4 h. Then the mixture was concentrated and PE was added. The black mixture was filtered. The filtration was concentrated in vacuum to afford the crude tert-butyl 7-methoxy-4-(4,4,5,5-tetramethyl-1,3,2-dioxaborolan-2-yl)indole-1-carboxylate. MS $[M+H]^+$: 374.0.

Intermediate E5 tert-butyl 5-chloro-4-(4,4,5,5-tetramethyl-1,3,2-dioxaborolan-2-yl)indole-1-carboxylate

Step 1: tert-butyl 5-amino-4-bromo-indole-1-carboxylate

To a solution of tert-butyl 5-amino-1H-indole-1-carboxylate (2 g, 8.61 mmol) in Acetonitrile (30 mL) was added NBS (1.53 g, 8.61 mmol), the reaction was stirred for 18 h at room temperature. The reaction mixture was concentrated in vacuum. The residue was purified by column chromatography to give tert-butyl 5-amino-4-bromo-1H-indole-1-carboxylate (2.2 g). MS $[M+H]^+$: 311.0.

Step 2: tert-butyl 4-bromo-5-chloro-indole-1-carboxylate

To a solution of tert-butyl nitrite (298 mg, 2.89 mmol) and copper(II) chloride dihydrate (493 mg, 2.89 mmol) in MeCN (10 mL) was added the solution of tert-butyl 5-amino-4-bromo-1H-indole-1-carboxylate (600 mg, 1.93 mmol) in MeCN (5 mL) at 0° C. The reaction was slowly warmed to 80° C. and stirred for 2 h. The reaction mixture was cooled to room temperature and filtered. The filtrate was concentrated in vacuum and the residue was purified by column chromatgraphy to give tert-butyl 4-bromo-5-chloro-1H-indole-1-carboxylate (368 mg, 1.11 mmol). MS $[M+H]^+$: 330.0.

Step 3: tert-butyl 5-chloro-4-(4,4,5,5-tetramethyl-1,3,2-dioxaborolan-2-yl)indole-1-carboxylate To a solution of tert-butyl 4-bromo-5-chloro-1H-indole-1-carboxylate (300 mg, 907 μmol) in Dioxane (10 mL) was added 4,4,4',4',5,5,5',5'-octamethyl-2,2'-bi(1,3,2-dioxaborolane) (253 mg, 998 μmol), potassium acetate (178 mg, 1.81 mmol) and 1,1-bis(diphenylphosphino)ferrocene-palladium(II)dichloride dichloromethane complex (74.1 mg, 90.7 μmol), the reaction was stirred for 12 h at 80° C. under atmosphere of argon. The reaction mixture was cooled to room temperature and filtered. The filtrate was concentrated in vacuum. The residue was purified by column chromatography to give tert-butyl 5-chloro-4-(4,4,5,5-tetramethyl-1,3,2-dioxaborolan-2-yl)-1H-indole-1-carboxylate (232 mg). MS $[M+H]^+$: 378.2.

Intermediate E6

1-methyl-4-(4,4,5,5-tetramethyl-1,3,2-dioxaborolan-2-yl)indole

Step 1: 4-bromo-1-methyl-indole

To a solution of 4-bromo-1H-indole (1 g, 5.1 mmol) in DMF (15 mL) was added sodium hydride (408 mg, 10.2 mmol) in portions at 0° C., the reaction was stirred for 30 min, then methyl iodide (1.45 g, 638 μl, 10.2 mmol) was added. The reaction mixture was stirred for 3 h at room temperature. The reaction was quenched with aqueous ammonia chloride and extracted in EtOAC. The organic layer was dried over anhydrous $Na_2SO_4$ and concentrated in vacuum. The residue was purified by column chromatography to give 4-bromo-1-methyl-indole (1 g). MS $[M+H]^+$: 210.0.

Step 2: 1-methyl-4-(4,4,5,5-tetramethyl-1,3,2-dioxaborolan-2-yl)indole

To a solution of 4-bromo-1-methyl-1H-indole (1000 mg, 4.76 mmol) in Dioxane (10 mL) was added 4,4,4',4',5,5,5',5'-octamethyl-2,2'-bi(1,3,2-dioxaborolane) (1.33 g, 5.24 mmol), potassium acetate (934 mg, 9.52 mmol) and 1,1-bis(diphenylphosphino)ferrocene-palladium(II)dichloride dichloromethane complex (389 mg, 476 μmol), the reaction was stirred for 12 h at 80° C. under atmosphere of argon. The reaction mixture was cooled to room temperature and filtered. The filtrate was concentrated in vacuum. The residue was purified by column chromatography to give 1-methyl-4-(4,4,5,5-tetramethyl-1,3,2-dioxaborolan-2-yl)-1H-indole (1 g). MS $[M+H]^+$: 258.2.

Intermediate F1

2,3,6-trifluoro-5-(4,4,5,5-tetramethyl-1,3,2-dioxaborolan-2-yl)pyridine

To a 25 mL microwave tube was added 4,4,5,5-tetramethyl-2-(4,4,5,5-tetramethyl-1,3,2-dioxaborolan-2-yl)-1,3,2-dioxaborolane (667 mg, 2.63 mmol), 3-chloro-2,5,6-trifluoro-pyridine (400 mg, 2.39 mmol), tris(dibenzylideneacetone)dipalladium (219 mg, 239 μmol), 2-dicyclohexylphosphino-2',4',6'-triisopropylbiphenyl (228 mg, 478 μmol) and potassium acetate (703 mg, 7.16 mmol) in 1,4-dioxane (15 mL). The vial was capped and heated at 100° C. for 3 h under $N_2$ protection. The reaction mixture was cooled to room temperature and concentrated. The residue was directly used to the next step without further purification.

Intermediate F2

N,N-dimethyl-5-(4,4,5,5-tetramethyl-1,3,2-dioxaborolan-2-yl)-6-(trifluoromethyl)pyridin-2-amine Step 1: 5-chloro-N,N-dimethyl-6-(trifluoromethyl)pyridin-2-amine To a 25 mL microwave vial was added 3,6-dichloro-2-(trifluoromethyl)pyridine (500 mg, 2.31 mmol) and dimethylamine (in methanol) (4.63 mL, 9.26 mmol) in MeOH (10 mL). The vial was capped and heated in the microwave at 100° C. for 3 h. The crude reaction mixture was concentrated in vacuum. The crude material was purified by flash chromatography. To afford 5-chloro-N,N-dimethyl-6-(trifluoromethyl)pyridin-2-amine (369 mg). MS $[M+H]^+$: 225.0.

Step 2: N,N-dimethyl-5-(4,4,5,5-tetramethyl-1,3,2-dioxaborolan-2-yl)-6-(trifluoromethyl)pyridin-2-amine To a 5 mL microwave vial was added 4,4,5,5-tetramethyl-2-(4,4,5,5-tetramethyl-1,3,2-dioxaborolan-2-yl)-1,3,2-dioxaborolane (452 mg, 1.78 mmol), 5-chloro-N,N-dimethyl-6-(trifluoromethyl)pyridin-2-amine (200 mg, 890 μmol), Chloro[(di(1-adamantyl)-N-butylphosphine)-2-(2-aminobiphenyl)]palladium(II) (59.5 mg, 89 μmol) and potassium acetate (262 mg, 2.67 mmol) in DMSO (5 mL). The vial was capped and heated at 110° C. for 3 h under $N_2$. The reaction mixture was poured into 50 mL $H_2O$ and extracted with EtOAc (3×25 mL). The organic layers were combined, washed with sat NaCl (1×50 mL), the organic layers were dried over $Na_2SO_4$ and concentrated in vacuum. The crude material was purified by flash chromatography. To afford N,N-dimethyl-5-(4,4,5,5-tetramethyl-1,3,2-dioxaborolan-2-yl)-6-(trifluoromethyl)pyridin-2-amine (89 mg, 282 μmol, 31.6% yield). MS $[M+H]^+$: 316.6.

Intermediate F3

N,N-dimethyl-5-(4,4,5,5-tetramethyl-1,3,2-dioxaborolan-2-yl)-4-(trifluoromethyl)pyrimidin-2-amine Step 1: NN-dimethyl-4-(trifluoromethyl)pyrimidin-2-amine To a solution of 2-chloro-4-(trifluoromethyl)pyrimidine (1 g, 5.48 mmol) in MeOH (5 mL) was added dimethylamine (in methanol) (13.7 mL, 27.4 mmol), the reaction was stirred for 2 h at room temperature. The reaction mixture was washed with brine and extracted in DCM. The organic layer was dried over anhydrous $Na_2SO_4$ and concentrated in vacuum to give N,N-dimethyl-4-(trifluoromethyl)pyrimidin-2-amine (0.96 g). MS $[M+H]^+$: 192.1.

Step 2: 5-bromo-N,N-dimethyl-4-(trifluoromethyl) pyrimidin-2-amine

To a solution of N,N-dimethyl-4-(trifluoromethyl)pyrimidin-2-amine (1 g, 5.23 mmol) in AcOH (10 mL) was added potassium acetate (1.54 g, 15.7 mmol) and bromine (836 mg, 270 μL, 5.23 mmol), the reaction was stirred for 20 h at 80° C. The reaction mixture was cooled to room temperature and washed with brine, extracted with EtOAc. The organic layer was dried over anhydrous $Na_2SO_4$ and concentrated in vacuum to give 5-bromo-N,N-dimethyl-4-(trifluoromethyl) pyrimidin-2-amine (1.03 g). MS $[M+H]^+$: 270.0.

Step 3: N,N-dimethyl-5-(4,4,5,5-tetramethyl-1,3,2-dioxaborolan-2-yl)-4 (trifluoromethyl)pyrimidin-2-amine To a solution of 5-bromo-N,N-dimethyl-4-(trifluoromethyl)pyrimidin-2-amine (600 mg, 2.22 mmol) in Dioxane (10 mL) was added 4,4,4',4',5,5,5',5'-octamethyl-2,2'-bi(1,3,2-dioxaborolane) (621 mg, 2.44 mmol), potassium acetate (436 mg, 4.44 mmol) and 1,1-bis(diphenylphosphino)ferrocene-palladium(II)dichloride dichloromethane complex (181 mg, 222 μmol), the reaction was stirred for 12 h at 80° C. under atmosphere of argon. The reaction mixture was cooled to room temperature and filtered. The filtrate was concentrated in vacuum. The residue was purified by column chromatography to give N,N-dimethyl-5-(4,4,5,5-tetramethyl-1,3,2-dioxaborolan-2-yl)-4-(trifluoromethyl)pyrimidin-2-amine (430 mg). MS $[M+H]^+$: 318.2.

Intermediate F4

2-methoxy-5-(4,4,5,5-tetramethyl-1,3,2-dioxaborolan-2-yl)-4-(trifluoromethyl)pyrimidine Step 1: 2-methoxy-4-(trifluoromethyl)pyrimidine To a solution of 2-chloro-4-(trifluoromethyl)pyrimidine (1.5 g, 8.22 mmol) in anhydrous MeOH (3 mL) was added sodium methoxide (3.29 mL, 16.4 mmol), the reaction was stirred for 2 h at room temperature. The reaction mixture was washed with brine and extracted in DCM. The organic layer was dried over anhydrous $Na_2SO_4$ and concentrated in vacuum to give 2-methoxy-4-(trifluoromethyl)pyrimidine (1.4 g). MS $[M+H]^+$: 179.0.

Step 2: 5-bromo-2-methoxy-4-(trifluoromethyl)pyrimidine

To a solution of 2-methoxy-4-(trifluoromethyl)pyrimidine (1.5 g, 8.42 mmol) in AcOH (40 mL) was added potassium acetate (2.48 g, 25.3 mmol) and bromine (1.35 g, 434 μL, 8.42 mmol), the reaction was stirred for 2 h at 80° C. The reaction mixture was cooled to room temperature and washed with brine, extracted in EtOAc. The organic layer was dried over anhydrous $Na_2SO_4$ and concentrated in vacuum. The residue was purified by column chromatography to give 5-bromo-2-methoxy-4-(trifluoromethyl)pyrimidine (1 g). MS $[M+H]^+$: 257.0.

Step 3: 2-methoxy-5-(4,4,5,5-tetramethyl-1,3,2-dioxaborolan-2-yl)-4 (trifluoromethyl)pyrimidine To a solution of 5-bromo-2-methoxy-4-(trifluoromethyl) pyrimidine (300 mg, 1.17 mmol) in Dioxane (10 mL) was added 4,4,4',4',5,5,5',5'-octamethyl-2,2'-bi(1,3,2-dioxaborolane) (326 mg, 1.28 mmol), potassium acetate (229 mg, 2.33 mmol) and 1,1-bis(diphenylphosphino)ferrocene-palladium (II)dichloride dichloromethane complex (95.3 mg, 117 μmol), the reaction was stirred for 12 h at 80° C. under atmosphere of argon. The reaction mixture was cooled to room temperature and filtered. The filtrate was concentrated in vacuum. The residue was purified by column chromatography to give 2-methoxy-5-(4,4,5,5-tetramethyl-1,3,2-dioxaborolan-2-yl)-4-(trifluoromethyl)pyrimidine (256 mg). MS $[M+H]^+$: 305.1.

Intermediate F5

4-chloro-2-methoxy-5-(4,4,5,5-tetramethyl-1,3,2-dioxaborolan-2-yl)pyridine

To a solution of 5-bromo-4-chloro-2-methoxypyridine (1100 mg, 5.0 mmol) in DMSO (10 mL) and was added bis(pinacolato)diboron (1270 mg, 5.0 mmol), Pd(dppf)$Cl_2$ (413 mg, 0.5 mmol) and potassium acetate (980 mg, 10 mmol) and then the resultant mixture was degassed for 5 min with nitrogen and then stirred for 4.0 h at 80° C.

After cooling to room temperature, the mixture was poured into water (100 mL) and the aqueous solution was extracted with EtOAc (100 mL×2). The organic layers were combined and washed with water and brine, dried over anhydrous sodium sulfate and concentrated under reduced pressure to give a red oil which was purified by Flash chromatography to provide 4-chloro-2-methoxy-5-(4,4,5,5-tetramethyl-1,3,2-dioxaborolan-2-yl)pyridine as an off-white solid (400 mg). MS $[M+H]^+$: 270.2

The following Intermediates were prepared in analogy of Intermediate F5:

| Ex# | Name | Structure | MS ESI $[M+H]^+$ | Starting Material |
|---|---|---|---|---|
| Intermediate F6 | 2-(difluoromethyl)-6-methoxy-3-(4,4,5,5-tetramethyl-1,3,2-dioxaborolan-2-yl)pyridine | 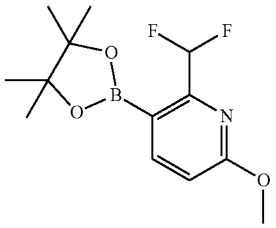 | 286.0 | 3-bromo-2-(difluoromethyl)-6-methoxypyridine and bis(pinacolato)diboron |

-continued

| Ex# | Name | Structure | MS ESI [M + H]$^+$ | Starting Material |
|---|---|---|---|---|
| Intermediate F7 | 6-methoxy-3-(4,4,5,5-tetramethyl-1,3,2-dioxaborolan-2-yl)-2-(trifluoromethyl)pyridine | 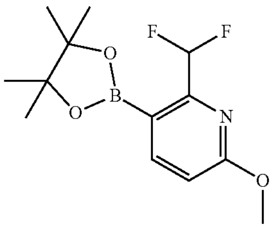 | 304.0 | 3-bromo-6-methoxy-2-(trifluoromethyl)pyridine and bis(pinacolato)diboron |

Intermediate O1 tert-butyl 2-chloro-4-[[5-[6-(dimethylamino)-2,5-difluoro-3-pyridyl]-1-methyl-imidazole-2-carbonyl]amino]benzoate

Step 1: tert-butyl 2-chloro-4-[[1-methyl-5-(2,5,6-trifluoro-3-pyridyl)imidazole-2-carbonyl]amino]benzoate Under $N_2$ protection, a mixture of tert-butyl 4-[(5-bromo-1-methyl-imidazole-2-carbonyl)amino]-2-chloro-benzoate (2.4 g, 5.79 mmol), 2,3,6-trifluoro-5-(4,4,5,5-tetramethyl-1,3,2-dioxaborolan-2-yl)pyridine (1.5 g, 5.79 mmol), $Na_2CO_3$ (1.84 g, 17.37 mmol) and 1,1'-bis(di-tert-butylphosphino)ferrocene palladium dichloride (377.41 mg, 0.579 mmol) in 25 mL microwave tube was heated at 100° C. for 2 h. Then the mixture was filtered and concentrated. The residue was purified by flash column to afford tert-butyl 2-chloro-4-[[1-methyl-5-(2,5,6-trifluoro-3-pyridyl)imidazole-2-carbonyl]amino]benzoate (2.1 g) as a yellow solid. MS [M+H]$^+$: 467.2.

Step 2: tert-butyl 2-chloro-4-[[5-[6-(dimethylamino)-2,5-difluoro-3-pyridyl]-1-methyl-imidazole-2-carbonyl]amino]benzoate tert-butyl 2-chloro-4-[[1-methyl-5-(2,5,6-trifluoro-3-pyridyl)imidazole-2-carbonyl]amino]benzoate (2.1 g, 4.5 mmol) was dissolved in MeOH (40 mL) at room temperature. Then 2 M dimethylamine in methanol (20.02 g, 44.98 mmol) was added. The yellow solution was stirred at room temperature for 1 h. Then the mixture was filtered and dried in vacuum to afford tert-butyl 2-chloro-4-[[5-[6-(dimethylamino)-2,5-difluoro-3-pyridyl]-1-methyl-imidazole-2-carbonyl]amino]benzoate (1.3 g) as a yellow solid. MS [M+H]$^+$: 492.4.

The following Intermediates were prepared in analogy of Intermediate O1:

| Ex# | Name | Structure | MS ESI [M + H]$^+$ | Starting Material |
|---|---|---|---|---|
| Intermediate G2 | tert-butyl 4-[2-chloro-4-[[5-[6-(dimethylamino)-2,5-difluoro-3-pyridyl]-1-methyl-imidazole-2-carbonyl]amino]benzoyl]piperazine-1-carboxylate | 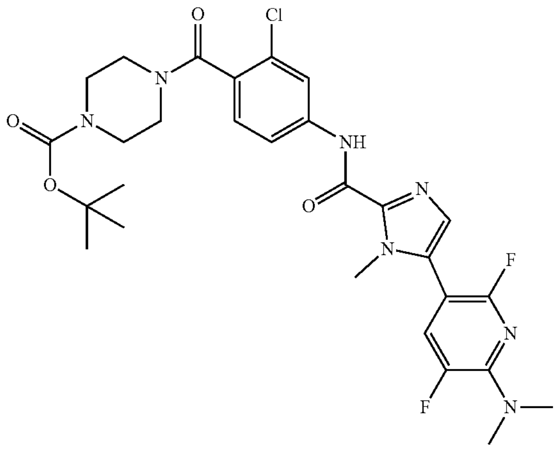 [SMILES: CN(C)c1nc(F)c(-c2cnc(C(=O)Nc3ccc(C(=O)N4CCN(C(=O)OC(C)(C)C)CC4)c(Cl)c3)n2C)cc1F] | 604.3 | Intermediate B1 and Intermediate F1 |

-continued

| Ex# | Name | Structure | MS ESI $[M + H]^+$ | Starting Material |
|---|---|---|---|---|
| Intermediate G3 | tert-butyl 4-[4-[[5-[6-(dimethylamino)-2,5-difluoro-3-pyridyl]-1-methyl-imidazole-2-carbonyl]amino]-2-methyl-benzoyl]piperazine-1-carboxylate | 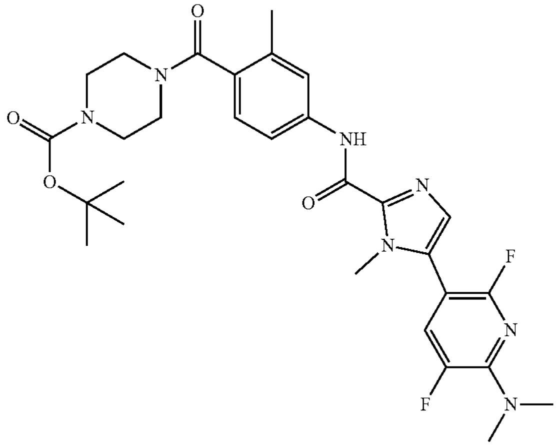 [SMILES: Cc1cc(NC(=O)c2ncc(-c3cc(F)c(N(C)C)nc3F)n2C)ccc1C(=O)N1CCN(C(=O)OC(C)(C)C)CC1] | 584.5 | Intermediate B2 and Intermediate F1 |

Intermediate H1

2-chloro-4-[[5-[6-(dimethylamino)-2,5-difluoro-3-pyridyl]-1-methyl-imidazole-2-carbonyl]amino]benzoic acid

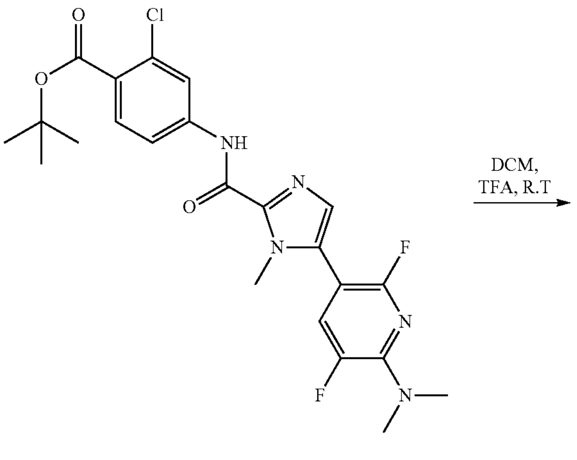

Intermediate G1

-continued

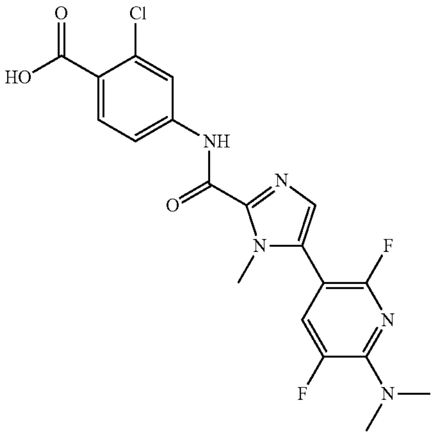

Intermediate H1 tert-butyl 2-chloro-4-[[5-[6-(dimethylamino)-2,5-difluoro-3-pyridyl]-1-methyl-imidazole-2-carbonyl]amino]benzoate (1.3 g, 2.64 mmol) was dissolved in dichloromethane (20 mL) and TFA (10 mL) at room temperature. Then the solution was stirred for 1 h. The mixture was concentrated in vacuum to afford 2-chloro-4-[[5-[6-(dimethylamino)-2,5-difluoro-3-pyridyl]-1-methyl-imidazole-2-carbonyl]amino]benzoic acid (1 g) as a yellow solid. MS $[M+H]^+$: 436.2.

Intermediate I1

N-[3-chloro-4-(piperazine-1-carbonyl)phenyl]-5-[6-(dimethylamino)-2,5-difluoro-3-pyridyl]-1-methyl-imidazole-2-carboxamide tert-butyl 4-[2-chloro-4-[[5-[6-(dimethylamino)-2,5-difluoro-3-pyridyl]-1-methyl-imidazole-2-carbonyl]amino]benzoyl]piperazine-1-carboxylate (600 mg, 0.993 mmol) was dissolved in dichloromethane (9 mL) and TFA (5 mL) at room temperature. Then the solution was stirred for 1 h.

Then the mixture was concentrated in vacuum and the residue was dissolved in DCM. The solution was basified by $NH_3 \cdot H_2O$. The water layer was extracted with DCM. The combined organic layers were dried over anhydrous $Na_2SO_4$ and concentrated in vacuum to afford N-[3-chloro-4-(piperazine-1-carbonyl)phenyl]-5-[6-(dimethylamino)-2,5-difluoro-3-pyridyl]-1-methyl-imidazole-2-carboxamide (450 mg). MS $[M+H]^+$: 504.1.

The following Intermediates were prepared in analogy of Intermediate I1:

| Ex# | Name | Structure | MS ESI $[M + H]^+$ | Starting Material |
|---|---|---|---|---|
| Intermediate I2 | 5-[6-(dimethylamino)-2,5-difluoro-3-pyridyl]-1-methyl-N-[3-methyl-4-(piperazine-1-carbonyl)phenyl]imidazole-2-carboxamide | 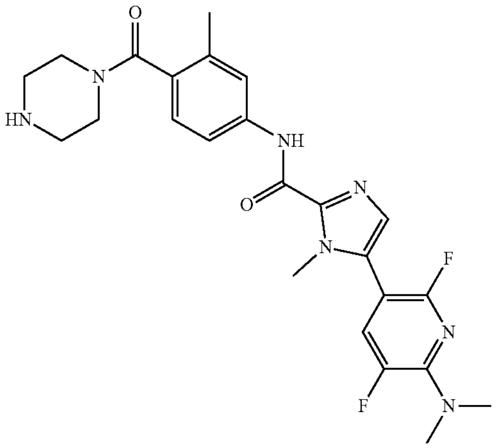 [SMILES: Cc1cc(NC(=O)c2ncc(-c3cc(F)c(N(C)C)nc3F)n2C)ccc1C(=O)N1CCNCC1] | 484.4 | Intermediate G3 |

Intermediate J1

N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide A mixture of N-[3-chloro-4-(piperazine-1-carbonyl)phenyl]-5-[6-(dimethylamino)-2,5-difluoro-3-pyridyl]-1-methyl-imidazole-2-carboxamide (400 mg, 0.794 mmol), 2-(dimethylamino)acetic acid (122.78 mg, 1.19 mmol), HATU (603.63 mg, 1.59 mmol) and DIPEA (307.77 mg, 2.38 mmol) in DMF (5 mL) was stirred at room temperature for 3 h. Then the mixture was poured into water. The water layer was extracted with DCM. The organic layer was concentrated to afford the crude product N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide. MS $[M+H]^+$: 589.3.

The following intermediates were prepared in analogy of Intermediate J1:

| Ex# | Name | Structure | MS ESI [M + H]+ | Starting Material |
|---|---|---|---|---|
| Inter-mediate J2 | N-[4-[4-[2-(di-methylamino)ace-tyl]piperazine-1-carbonyl]-3-methyl-phenyl]-5-[6-(dimethylamino)-2,5-difluoro-3-pyridyl]-1-methyl-imidazole-2-carboxamide | 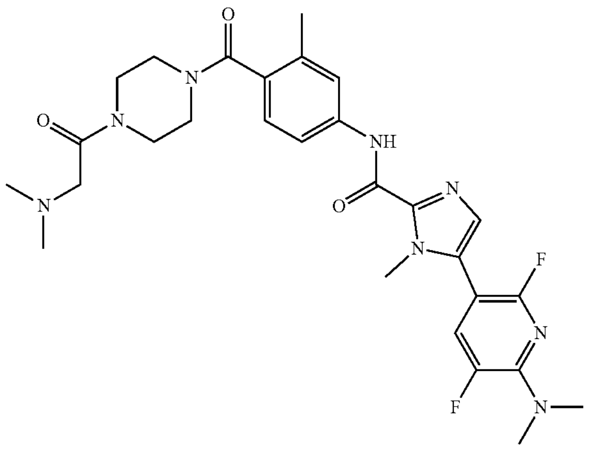 | 569.6 | Intermediate I2 and 2-(dimethylamino) acetic acid |
| Inter-mediate J3 | tert-butyl 4-[4-[2-chloro-4-[[5-[6-(dimethylamino)-2,5-difluoro-3-pyridyl]-1-methyl-imidazole-2-car-bonyl]amino]ben-zoyl]piperazine-1-carbonyl]-4-hydroxy-piperidine-1-carboxylate | 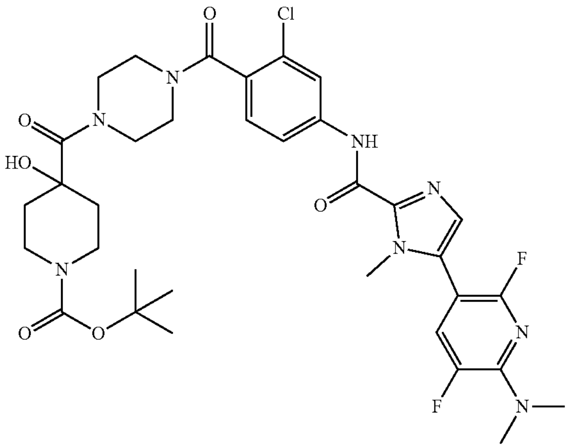 [SMILES: CN(C)c1nc(F)c(-c2cnc(C(=O)Nc3ccc(C(=O)N4CCN(C(=O)C5(O)CCN(C(=O)OC(C)(C)C)CC5)CC4)c(Cl)c3)n2C)cc1F] | 730.1 | Intermediate I1 and 1-tert-butoxycarbonyl-4-hydroxy-piperidine-4-carboxylic acid |
| Inter-mediate J4 | tert-butyl (3S)-3-[2-[4-[2-chloro-4-[[5-[6-(dimethylamino)-2,5-difluoro-3-pyridyl]-1-methyl-imidazole-2-car-bonyl]amino]ben-zoyl]piperazin-1-yl]-2-oxo-ethyl]pyrrolidine-1-carboxyalte | 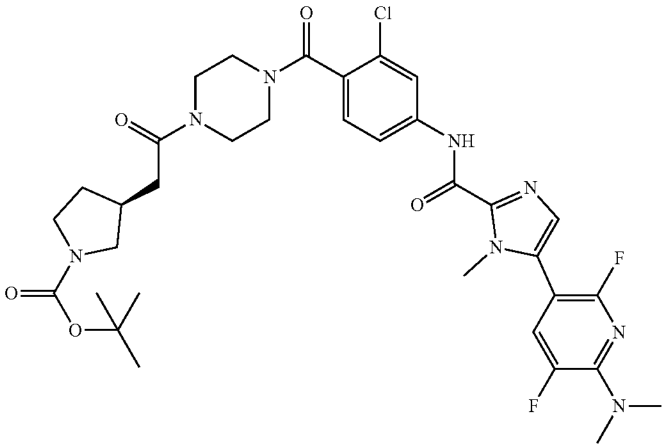 [SMILES: CN(C)c1nc(F)c(-c2cnc(C(=O)Nc3ccc(C(=O)N4CCN(C(=O)C[C@@H]5CCN(C(=O)OC(C)(C)C)C5)CC4)c(Cl)c3)n2C)cc1F] | 715.2 | Intermediate I1 and 2-[(3S)-1-tert-butoxycarbonyl-pyrrolidin-3-yl]acetic acid |

-continued

| Ex# | Name | Structure | MS ESI [M + H]+ | Starting Material |
|---|---|---|---|---|
| Intermediate J5 | tert-butyl 4-[2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]-4-hydroxy-piperidine-1-carboxylate | 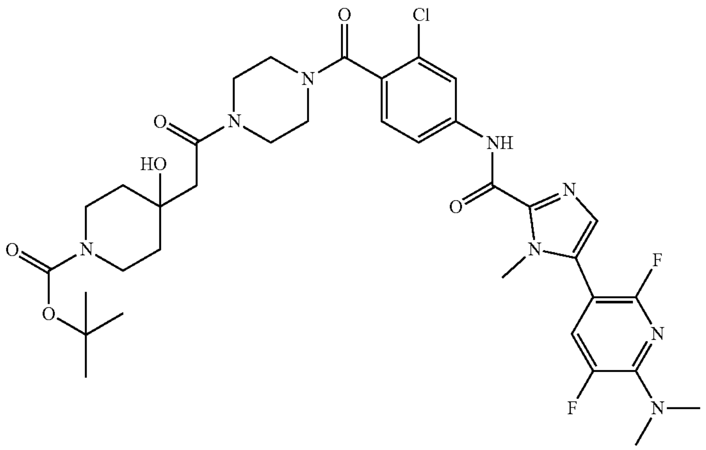 [SMILES: CN(C)c1nc(F)c(-c2cnc(C(=O)Nc3ccc(C(=O)N4CCN(C(=O)CC5(O)CCN(C(=O)OC(C)(C)C)CC5)CC4)c(Cl)c3)n2C)cc1F] | 745.0 | Intermediate I1 and 2-(1-tert-butoxycarbonyl-4-hydroxy-4-piperidyl)acetic acid |
| Intermediate J6 | tert-butyl 3-[4-[2-chloro-4-[[5-[6-(dimethylamino)-2,5-difluoro-3-pyridyl]-1-methyl-imidazole-2-carbonyl]amino]benzoyl]piperazine-1-carbonyl]pyrrolidine-1-carboxylate | 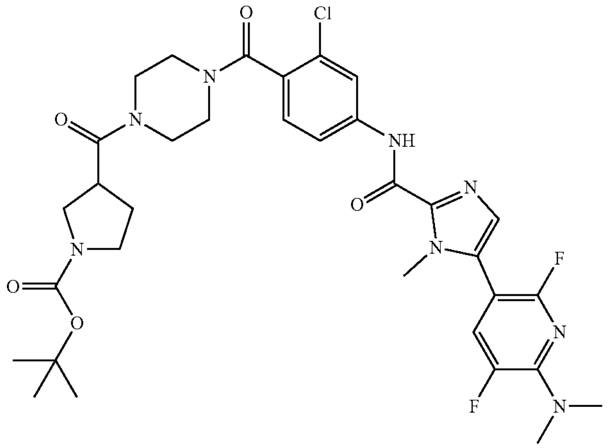 [SMILES: CN(C)c1nc(F)c(-c2cnc(C(=O)Nc3ccc(C(=O)N4CCN(C(=O)C5CCN(C(=O)OC(C)(C)C)C5)CC4)c(Cl)c3)n2C)cc1F] | 701.6 | Intermediate I1 and 1-tert-butoxycarbonyl-pyrrolidine-3-carboxylic acid |
| Intermediate J7 | tert-butyl (2S,4R)-2-[4-[2-chloro-4-[[5-[6-(dimethylamino)-2,5-difluoro-3-pyridyl]-1-methyl-imidazole-2-carbonyl]amino]benzoyl]piperazine-1-carbonyl]-4-hydroxy-pyrrolidine-1-carboxylate | 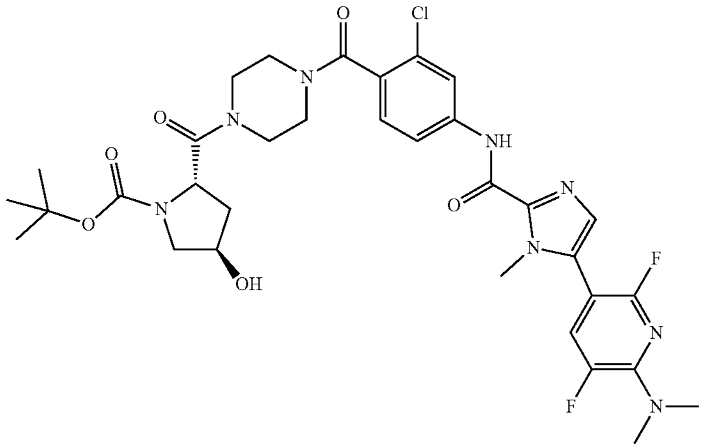 [SMILES: CN(C)c1nc(F)c(-c2cnc(C(=O)Nc3ccc(C(=O)N4CCN(C(=O)[C@@H]5C[C@@H](O)CN5C(=O)OC(C)(C)C)CC4)c(Cl)c3)n2C)cc1F] | 717.5 | Intermediate I1 and (2S,4R)-1-tert-butoxycarbonyl-4-hydroxy-proline |

-continued

| Ex# | Name | Structure | MS ESI [M + H]+ | Starting Material |
|---|---|---|---|---|
| Intermediate J8 | tert-butyl 4-[2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]piperidine-1-carboxylate | 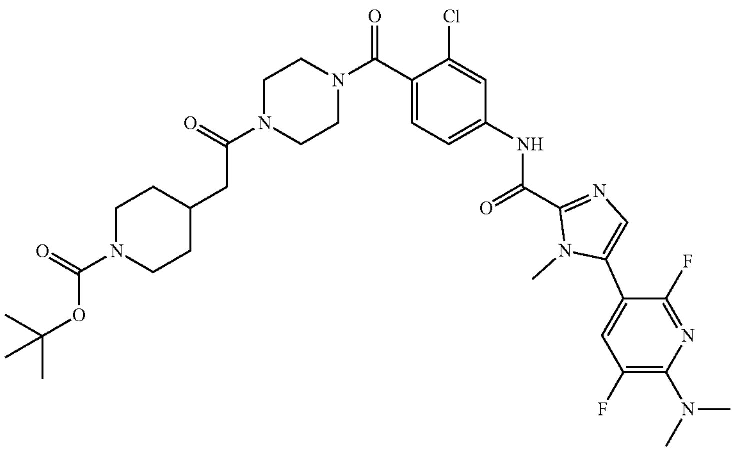 [SMILES: CN(C)c1nc(F)c(-c2cnc(C(=O)Nc3ccc(C(=O)N4CCN(C(=O)CC5CCN(C(=O)OC(C)(C)C)CC5)CC4)c(Cl)c3)n2C)cc1F] | 729.6 | Intermediate I1 and 2-(1-tert-butoxycarbonyl-4-piperidyl)acetic acid |
| Intermediate J9 | tert-butyl N-[[3-[4-[2-chloro-4-[[5-[6-(dimethylamino)-2,5-difluoro-3-pyridyl]-1-methyl-imidazole-2-carbonyl]amino]benzoyl]piperazine-1-carbonyl]cyclobutyl]methyl]carbamate | 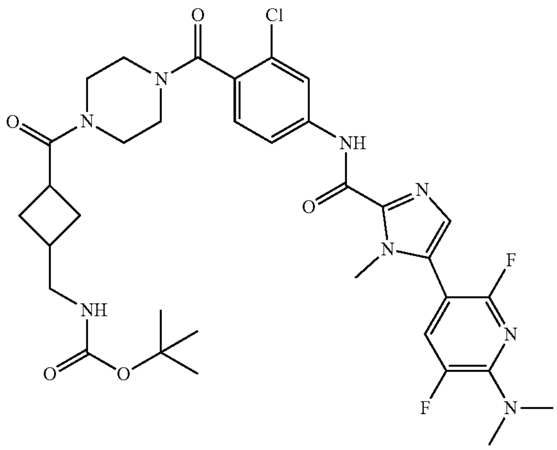 [SMILES: CN(C)c1nc(F)c(-c2cnc(C(=O)Nc3ccc(C(=O)N4CCN(C(=O)C5CC(CNC(=O)OC(C)(C)C)C5)CC4)c(Cl)c3)n2C)cc1F] | 715.2 | Intermediate I1 and 3-[(tert-butoxycarbonylamino)methyl]cyclobutanecarboxylic acid |
| Intermediate J10 | tert-butyl N-[2-[3-[4-[[2-chloro-4-[[5-[6-(dimethylamino)-2,5-difluoro-3-pyridyl]-1-methyl-imidazole-2-carbonyl]amino]benzoyl]amino]-1-piperidyl]-3-oxo-propoxy]ethyl]carbamate | 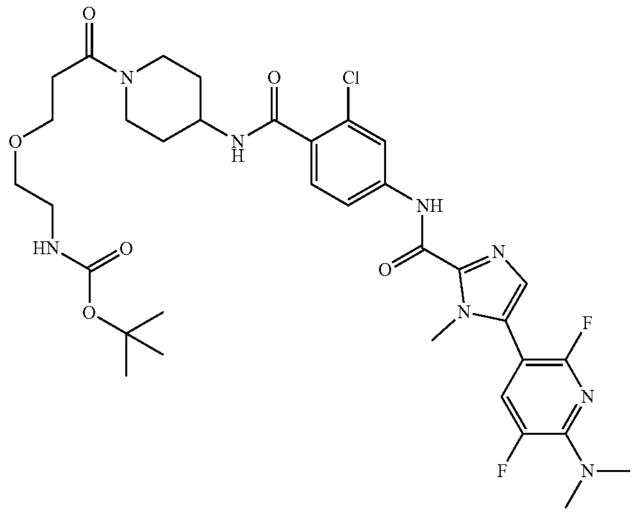 [SMILES: CN(C)c1nc(F)c(-c2cnc(C(=O)Nc3ccc(C(=O)NC4CCN(C(=O)CCOCCNC(=O)OC(C)(C)C)CC4)c(Cl)c3)n2C)cc1F] | 733.2 | Intermediate L1 and 3-[2-(tert-butoxycarbonylamino)ethoxy]propionic acid |

-continued

| Ex# | Name | Structure | MS ESI [M + H]$^+$ | Starting Material |
|---|---|---|---|---|
| Intermediate J11 | N-[3-chloro-4-[[3-[[2-(dimethylamino)acetyl]amino]cyclobutyl]carbamoyl]phenyl]-5-[6-(dimethylamino)-2,5-difluoro-3-pyridyl]-1-methyl-imidazole-2-carboxamide | 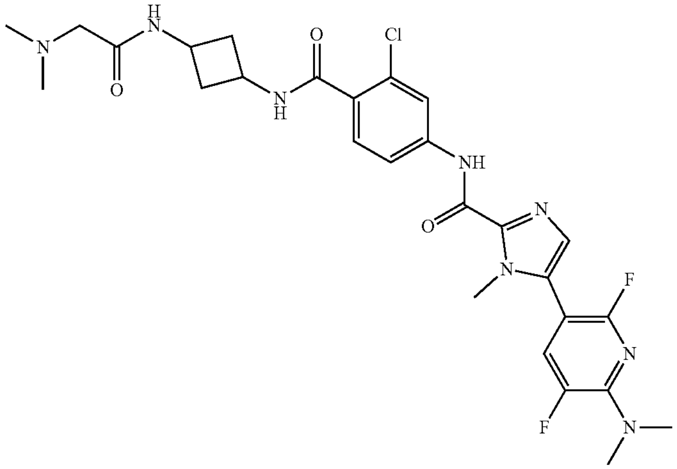 | 589.2 | Intermediate L2 and 2-(dimethylamino) acetic acid |
| Intermediate J12 | N-[3-chloro-4-[4-[[2-(dimethylamino)acetyl]amino]piperidine-1-carbonyl]phenyl]-5-[6-(dimethylamino)-2,5-difluoro-3-pyridyl]-1-methyl-imidazole-2-carboxamide | 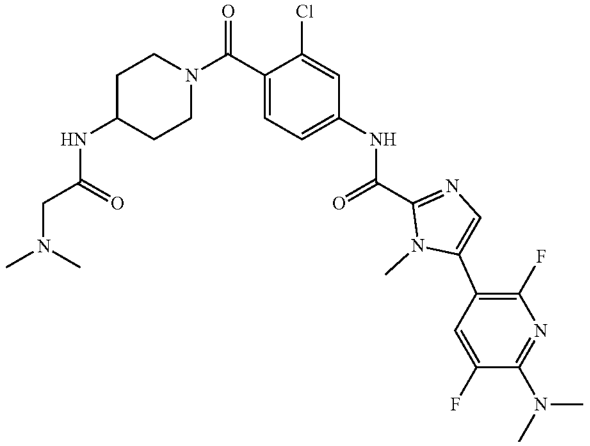 | 603.2 | Intermediate L3 and 2-(dimethylamino) acetic acid |
| Intermediate J13 | tert-butyl (2S,4R)-2-[4-[[2-chloro-4-[[5-[6-(dimethylamino)-2,5-difluoro-3-pyridyl]-1-methyl-imidazole-2-carbonyl]amino]benzoyl]amino]piperidine-1-carbonyl]-4-hydroxy-pyrrolidine-1-carboxylate | 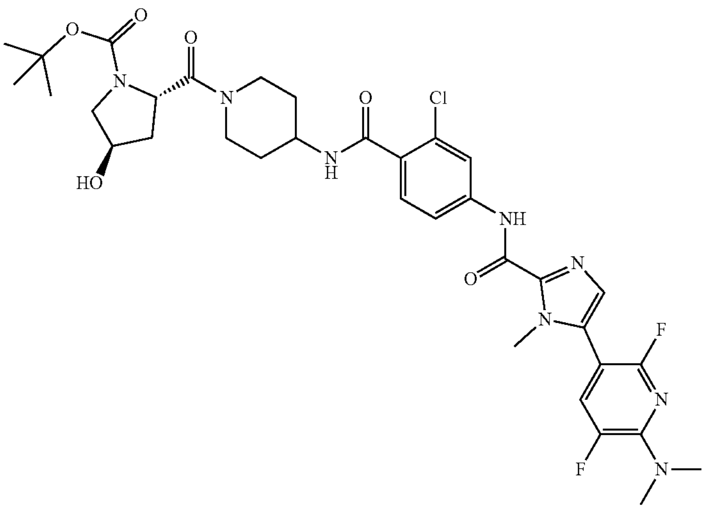 [SMILES: CN(C)c1nc(F)c(-c2cnc(C(=O)Nc3ccc(C(=O)NC4CCN(C(=O)[C@@H]5C[C@@H](O)CN5C(=O)OC(C)(C)C)CC4)c(Cl)c3)n2C)cc1F] | 731.2 | Intermediate L1 and (2S,4R)-1-tert-butoxycarbonyl-4-hydroxy-proline |

-continued

| Ex# | Name | Structure | MS ESI [M + H]+ | Starting Material |
|---|---|---|---|---|
| Intermediate J14 | tert-butyl 3-[[1-[2-chloro-4-[[5-[6-(dimethylamino)-2,5-difluoro-3-pyridyl]-1-methyl-imidazole-2-carbonyl]amino]benzoyl]piperidine-4-carbonyl]amino]pyrrolidine-1-carboxylate | 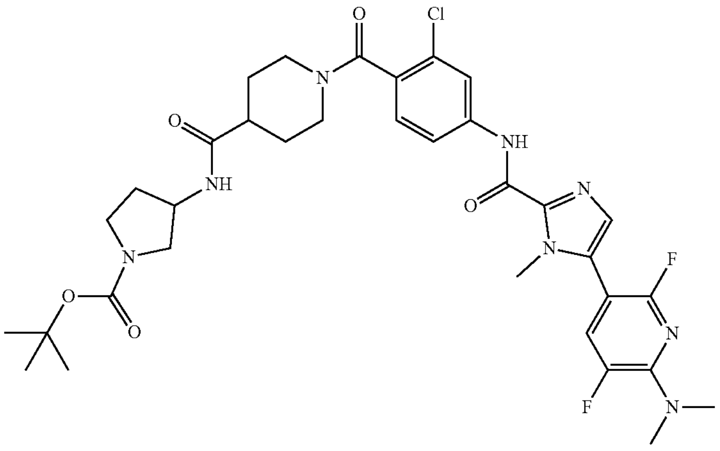 [SMILES: CN(C)c1nc(F)c(-c2cnc(C(=O)Nc3ccc(C(=O)N4CCC(C(=O)NC5CCN(C(=O)OC(C)(C)C)C5)CC4)c(Cl)c3)n2C)cc1F] | 715.2 | Intermediate L4 and 3-aminopyrrolidine-1-carboxylic acid tert-butyl ester |

N-[4-(6-aminohexylcarbamoyl)-3-chloro-phenyl]-5-[6-(dimethylamino)-2,5-difluoro-3-pyridyl]-1-methyl-imidazole-2-carboxamide Step 1: tert-butyl N-[6-[[2-chloro-4-[[5-[6-(dimethylamino)-2,5-difluoro-3-pyridyl]-1-methyl-imidazole-2-carbonyl]amino]benzoyl]amino]hexyl]carbamate A mixture of 2-chloro-4-[[5-[6-(dimethylamino)-2,5-difluoro-3-pyridyl]-1-methyl-imidazole-2-carbonyl]amino] benzoic acid (400 mg, 0.918 mmol), tert-butyl N-(6-aminohexyl)carbamate (297.82 mg, 1.38 mmol), HATU (697.98 mg, 1.84 mmol) and DIPEA (355.88 mg, 2.75 mmol) in DMF (6 mL) was stirred at room temperature for 3 h. Then the mixture was poured into water. The water layer was extracted with DCM. The organic layer was dried over anhydrous $Na_2SO_4$ and concentrated in vacuum to afford the crude product tert-butyl N-[6-[[2-chloro-4-[[5-[6-(dimethylamino)-2,5-difluoro-3-pyridyl]-1-methyl-imidazole-2-carbonyl]amino]benzoyl]amino]hexyl]carbamate. MS $[M+H]^+$: 634.2.

Step 2: N-[4-(6-aminohexylcarbamoyl)-3-chloro-phenyl]-5-[6-(dimethylamino)-2,5-difluoro-3-pyridyl]-1-methyl-imidazole-2-carboxamide tert-butyl N-[6-[[2-chloro-4-[[5-[6-(dimethylamino)-2,5-difluoro-3-pyridyl]-1-methyl-imidazole-2-carbonyl]amino] benzoyl]amino]hexyl]carbamate (500 mg, 0.788 mmol) was dissolved in dichloromethane (10 mL) and TFA (5 mL) at room temperature. Then the solution was stirred for 1 h. The mixture was concentrated and water was added. The mixture was basified by DIPEA. The water layer was extracted with DCM. The combined organic layers were washed with water, dried over anhydrous $Na_2SO_4$ and concentrated in vacuum to afford the crude product N-[4-(6-aminohexylcarbamoyl)-3-chloro-phenyl]-5-[6-(dimethylamino)-2,5-difluoro-3-pyridyl]-1-methyl-imidazole-2-carboxamide. MS $[M+H]^+$: 534.3.

Intermediate L1

N-[3-chloro-4-(4-piperidylcarbamoyl)phenyl]-5-[6-(dimethylamino)-2,5-difluoro-3-pyridyl]-1-methyl-imidazole-2-carboxamide Step 1: tert-butyl 4-[[2-chloro-4-[[5-[6-(dimethylamino)-2,5-difluoro-3-pyridyl]-1-methyl-imidazole-2-carbonyl]amino]benzoyl]amino]piperidine-1-carboxylate 2-chloro-4-[[5-[6-(dimethylamino)-2,5-difluoro-3-pyridyl]-1-methyl-imidazole-2-carbonyl]amino]benzoic acid (Intermediate H1, 240 mg, 0.551 mmol), 1-methylimidazole (158.24 mg, 153.63 uL, 1.93 mmol), 4-aminopiperidine-1-carboxylic acid tert-butyl ester (132.35 mg, 0.661 mmol) were dissolved in acetonitrile (6 mL) and chloro-n,n,n',n'-tetramethylformamidinium hexafluorophosphate (185.42 mg, 0.661 mmol) was added in one portion. The mixture was stirred at room temperature for 1 h. The solvent was removed in vacuum. The residue was purified by flash chromatography to afford the crude product tert-butyl 4-[[2-chloro-4-[[5-[6-(dimethylamino)-2,5-difluoro-3-pyridyl]-1-methyl-imidazole-2-carbonyl]amino]benzoyl]amino]piperidine-1-carboxylate. MS $[M+H]^+$: 618.4.

Step 2: N-[3-chloro-4-(4-piperidylcarbamoyl)phenyl]-5-[6-(dimethylamino)-2,5-difluoro-3-pyridyl]-1-methyl-imidazole-2-carboxamide tert-butyl 4-[[2-chloro-4-[[5-[6-(dimethylamino)-2,5-difluoro-3-pyridyl]-1-methyl-imidazole-2-carbonyl]amino] benzoyl]amino]piperidine-1-carboxylate (320 mg, 0.518 mmol) was stirred in dichoromethane (4 mL) and 1 mL TFA at room temperature for 2 h. The solvent was removed in vacuo to give the crude product which was used in the next step without purification. MS $[M+H]^+$: 518.1.

The following intermediates were prepared in analogy of Intermediate L1:

| Ex# | Name | Structure | MS ESI $[M + H]^+$ | Starting Material |
|---|---|---|---|---|
| Intermediate L2 | N-[4-[(3-aminocyclobutyl) carbamoyl]-3-chloro-phenyl]-5-[6-(dimethylamino)-2,5-difluoro-3-pyridyl]-1-methyl-imidazole-2-carboxamide | 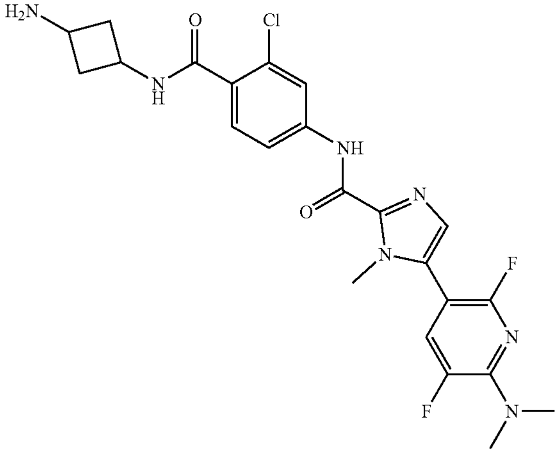 [SMILES: CN(C)c1nc(F)c(-c2cnc(C(=O)Nc3ccc(C(=O)NC4CC(N)C4)c(Cl)c3)n2C)cc1F] | 504.1 | Intermediate H1 and N-(3-aminocyclobutyl) carbamic acid tert-butyl ester |
| Intermediate L3 | N-[4-(4-aminopiperidine-1-carbonyl)-3-chloro-phenyl]-5-[6-(dimethylamino)-2,5-difluoro-3-pyridyl]-1-methyl-imidazole-2-carboxamide | 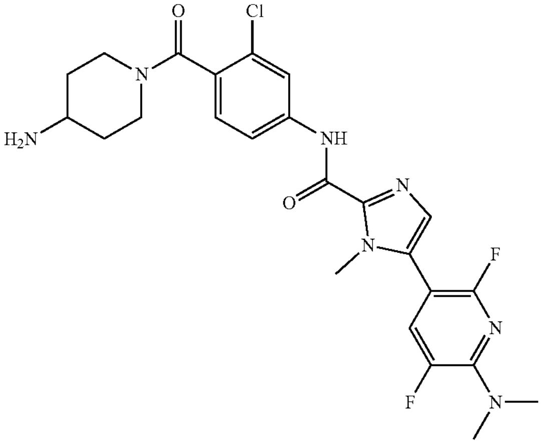 [SMILES: CN(C)c1nc(F)c(-c2cnc(C(=O)Nc3ccc(C(=O)N4CCC(N)CC4)c(Cl)c3)n2C)cc1F] | 518.1 | Intermediate H1 and N-(4-piperidyl)carbamic acid tert-butyl ester |

Intermediate L4

1-[2-chloro-4-[[5-[6-(dimethylamino)-2,5-difluoro-3-pyridyl]-1-methyl-imidazole-2-carbonyl]amino] benzoyl]piperidine-4-carboxylic Acid Step 1: methyl 1-[2-chloro-4-[[5-[6-(dimethylamino)-2,5-difluoro-3-pyridyl]-1-methyl-imidazole-2-carbonyl]amino]benzoyl]piperidine-4-carboxylate To a solution of 2-chloro-4-[[5-[6-(dimethylamino)-2,5-difluoro-3-pyridyl]-1-methyl-imidazole-2-carbonyl]amino] benzoic acid (300 mg, 0.688 mmol) in N,N-dimethylformamide (3 mL) was added methyl isonipecotate (98.56 mg, 92.98 uL, 0.688 mmol), o-(7-aza-1 h-benzotriazol-1-yl)-n,n,n',n'-tetramethyluronium hexafluorophosphate (392.61 mg, 1.03 mmol) and TEA (139.32 mg, 1.376 mmol), the reaction was stirred for 30 min at room temperature. The reaction mixture was poured into water and filtered. The filter cake was dried in vacuum to give methyl 1-[2-chloro-4-[[5-[6-(dimethylamino)-2,5-difluoro-3-pyridyl]-1-methyl-imidazole-2-carbonyl]amino]benzoyl]piperidine-4-carboxylate (320 mg). MS $[M+H]^+$: 561.2.

Step 2: 1-[2-chloro-4-[[5-[6-(dimethylamino)-2,5-difluoro-3-pyridyl]-1-methyl-imidazole-2-carbonyl] amino]benzoyl]piperidine-4-carboxylic Acid To a solution of 1-[2-chloro-4-[[5-[6-(dimethylamino)-2,5-difluoro-3-pyridyl]-1-methyl-imidazole-2-carbonyl] amino]benzoyl]isonipecotic acid methyl ester (250 mg, 0.446 mmol) in the mixture solvent of methanol (5 mL) and water (1 mL), the reaction was stirred for 2 h at room temperature. The reaction mixture was acidified with acetic acid. The mixture was poured into water and filtered. The filter cake was dried in vacuum to give 1-[2-chloro-4-[[5-[6-(dimethylamino)-2,5-difluoro-3-pyridyl]-1-methyl-imidazole-2-carbonyl]amino]benzoyl]piperidine-4-carboxylic acid (230 mg). MS $[M+H]^+$: 547.2

Intermediate M1

N-[4-[[1-[3-(2-aminoethoxy)propanoyl]-4-piperidyl] carbamoyl]-3-chloro-phenyl]-5-[6-(dimethylamino)-2,5-difluoro-3-pyridyl]-1-methyl-imidazole-2-carboxamide tert-butyl N-[2-[3-[4-[[2-chloro-4-[[5-[6-(dimethylamino)-2,5-difluoro-3-pyridyl]-1-methyl-imidazole-2-carbonyl]amino]benzoyl]amino]-1-piperidyl]-3-oxo-propoxy] ethyl]carbamate (200 mg) was dissolved in 4M HCl/1,4-dioxane (5 mL) solution and stirred at room temperature for 2 h. The solvent was removed in vacuum to afford the crude product which was purified by preparative HPLC. MS $[M+H]^+$: 633.2.

The following intermediates were prepared in analogy of Intermediate M1:

| Ex# | Name | Structure | MS ESI $[M + H]^+$ | Starting Material |
|---|---|---|---|---|
| Intermediate M2 | N-[3-chloro-4-[[1-[(2S,4R)-4-hydroxypyrrolidine-2-carbonyl]-4-piperidyl]carbamoyl] phenyl]-5-[6-(dimethylamino)-2,5-difluoro-3-pyridyl]-1-methyl-imidazole-2-carboxamide | 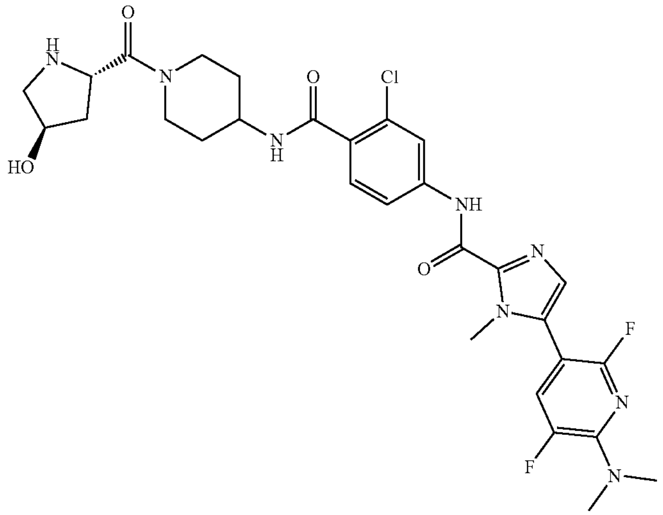 [SMILES: CN(C)c1nc(F)c(-c2cnc(C(=O)Nc3ccc(C(=O)NC4CCN(C(=O)[C@@H]5C[C@@H](O)CN5)CC4)c(Cl)c3)n2C)cc1F] | 631.3 | Intermediate J13 and HCl |
| Intermediate M3 | 1-[2-chloro-4-[[5-[6-(dimethylamino)-2,5-difluoro-3-pyridyl]-1-methyl-imidazole-2-carbonyl]amino] benzoyl]-N-pyrrolidin-3-yl-piperidine-4-carboxamide | 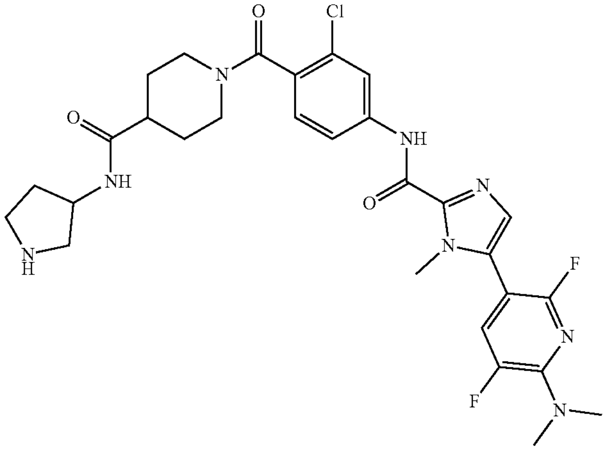 [SMILES: CN(C)c1nc(F)c(-c2cnc(C(=O)Nc3ccc(C(=O)N4CCC(C(=O)NC5CCNC5)CC4)c(Cl)c3)n2C)cc1F] | 615.4 | J14 and HCl |
| Intermediate M4 | N-[3-chloro-4-[4-(pyrrolidine-3-carbonyl)piperazine-1-carbonyl]phenyl]-5-[6-(dimethylamino)-2,5-difluoro-3-pyridyl]-1-methyl-imidazole-2-carboxamide | 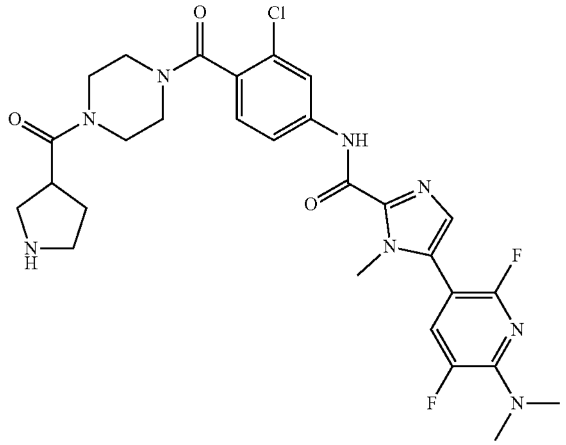 [SMILES: CN(C)c1nc(F)c(-c2cnc(C(=O)Nc3ccc(C(=O)N4CCN(C(=O)C5CCNC5)CC4)c(Cl)c3)n2C)cc1F] | 601.2 | Intermediate J6 and HCl |

-continued

| Ex# | Name | Structure | MS ESI [M + H]+ | Starting Material |
|---|---|---|---|---|
| Intermediate M5 | N-[3-chloro-4-[4-[(2S,4R)-4-hydroxypyrrolidine-2-carbonyl]piperazine-1-carbonyl]phenyl]-5-[6-(dimethylamino)-2,5-difluoro-3-pyridyl]-1-methyl-imidazole-2-carboxamide | 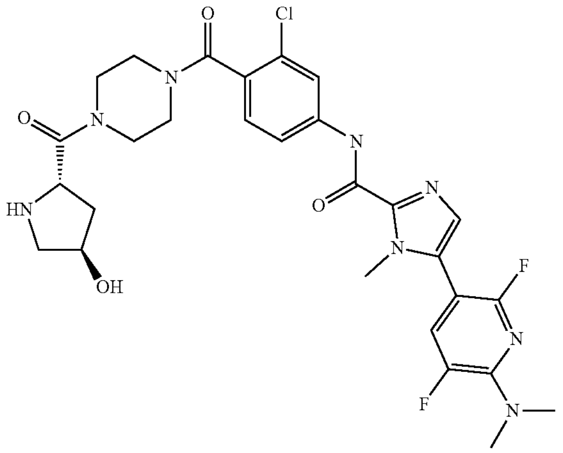 [SMILES: CN(C)c1nc(F)c(-c2cnc(C(=O)Nc3ccc(C(=O)N4CCN(C(=O)[C@@H]5C[C@@H](O)CN5)CC4)c(Cl)c3)n2C)cc1F] | 617.4 | Intermediate J7 and HCl |
| Intermediate M6 | N-[3-chloro-4-[4-[2-(4-piperidyl)acetyl]piperazine-1-carbonyl]phenyl]-5-[6-(dimethylamino)-2,5-difluoro-3-pyridyl]-1-methyl-imidazole-2-carboxamide | 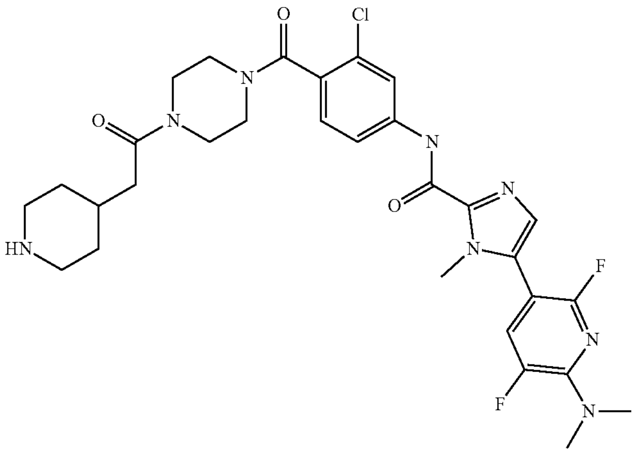 [SMILES: CN(C)c1nc(F)c(-c2cnc(C(=O)Nc3ccc(C(=O)N4CCN(C(=O)CC5CCNCC5)CC4)c(Cl)c3)n2C)cc1F] | 629.4 | Intermediate J8 and HCl |

Example A1

N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide; formic Acid

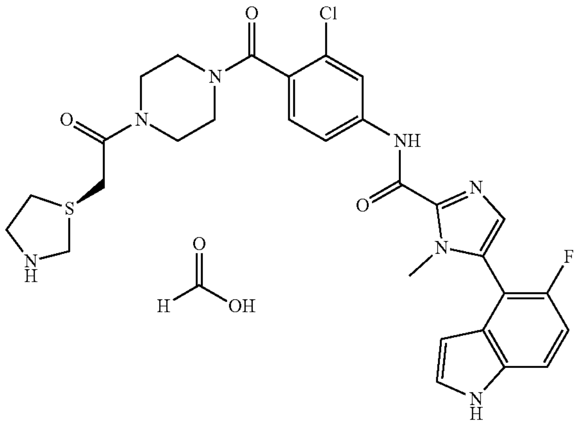

Step 1: tert-butyl 4-[2-[[4-[4-[2-[(3S)-1-tert-butoxycarbonylpyrrolidin-3-yl]acetyl]piperazine-1-carbonyl]-3-chloro-phenyl]carbamoyl]-3-methyl-imidazol-4-yl]-5-fluoro-indole-1-carboxylate A mixture of tert-butyl (3S)-3-[2-[4-[4-[(5-bromo-1-methyl-imidazole-2-carbonyl)amino]-2-chloro-benzoyl]piperazin-1-yl]-2-oxo-ethyl]pyrrolidine-1-carboxylate (400 mg, 627 μmol), tert-butyl 5-fluoro-4-(4,4,5,5-tetramethyl-1,3,2-dioxaborolan-2-yl)indole-1-carboxylate (272 mg, 752 μmol), $Na_2CO_3$ (199 mg, 1.88 mmol) and 1,1'-bis(di-tert-butylphosphino)ferrocene palladium dichloride (40.86 mg, 0.063 mmol) in 1,4-dioxane (10 mL) and water (1 mL) was heated at 110° C. for 50 min in a 25 mL microwave tube under $N_2$ protection. Then the mixture was filtered and the filtration was concentrated. The residue was dissolved in DCM. The organic layer was washed with water, dried over anhydrous $Na_2SO_4$ and concentrated in vacuum. The residue was purified by flash column chromatography to afford tert-butyl 4-[2-[[4-[4-[2-[(3S)-1-tert-butoxycarbonylpyrrolidin-3-yl]acetyl]piperazine-1-carbonyl]-3-chloro-phenyl]carbamoyl]-3-methyl-imidazol-4-yl]-5-fluoro-indole-1-carboxylate.

Step 2: N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide; formic acid A solution of tert-butyl 4-[2-[[4-[4-[2-[(3S)-1-tert-butoxycarbonylpyrrolidin-3-yl]acetyl]piperazine-1-carbonyl]-3-chloro-phenyl]carbamoyl]-3-methyl-imidazol-4-yl]-5-fluoro-indole-1-carboxylate (400 mg, 0.505 mmol) in DCM (10 mL) and TFA (6 mL) was stirred at room temperature for 30 min. Then the solution was concentrated and basified by $NH_3 \cdot H_2O$. The water layer was extracted with DCM. The combined organic layers were dried over anhydrous $Na_2SO_4$ and concentrated in vacuum to afford the crude product. The residue was purified by Prep-HPLC to afford N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide; formic acid (31 mg). MS $[M+H]^+$: 592.3.

The following Intermediates were prepared in analogy of Example A1:

| Ex# | Name | Structure | MS ESI $[M + H]^+$ | Starting Material |
|---|---|---|---|---|
| Example A2 | N-[3-chloro-4-[4-[2-[(3S)-pyrrolidin-3-yl]acetyl]piperazine-1-carbonyl]phenyl]-5-(6-fluoro-3-methyl-1H-indazol-5-yl)-1-methyl-imidazole-2-carboxamide; 2,2,2-trifluoroacetic acid | 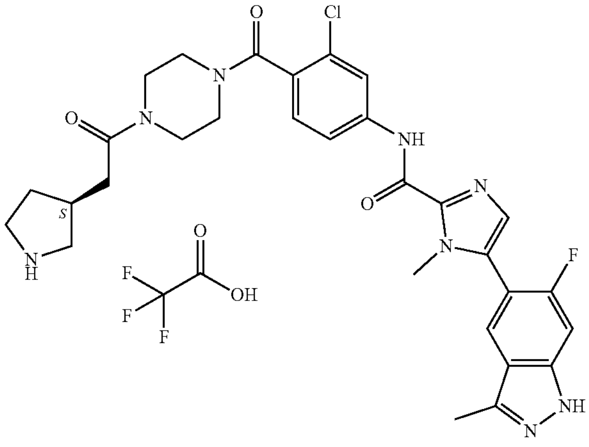 | 607.1 | Intermediate D1 and Intermediate E2 |

-continued

| Ex# | Name | Structure | MS ESI [M + H]+ | Starting Material |
|---|---|---|---|---|
| Example A3 | N-[3-chloro-4-[4-[2-[(3S)-pyrrolidin-3-yl]acetyl]piperazine-1-carbonyl]phenyl]-1-methyl-5-[3-(trifluoromethyl)-1H-indazol-5-yl]imidazole-2-carboxamide; formic acid | 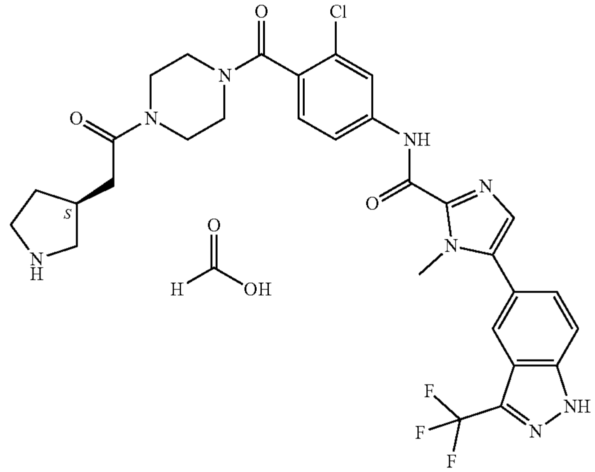 | 643.2 | Intermediate D1 and Intermediate E3 |
| Example A4 | N-[3-chloro-4-[4-[2-[(3S)-pyrrolidin-3-yl]acetyl]piperazine-1-carbonyl]phenyl]-5-(7-methoxy-1H-indol-4-yl)-1-methyl-imidazole-2-carboxamide; formic acid | 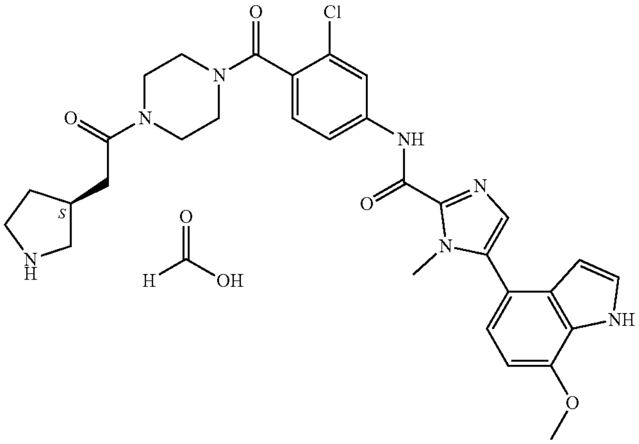 | 604.2 | Intermediate D1 and Intermediate E4 |
| Example A5 | N-[3-chloro-4-[4-(piperidine-4-carbonyl)piperazine-1-carbonyl]phenyl]-5-(2,6-dichloro-3-pyridyl)-1-methyl-imidazole-2-carboxamide; formic acid | 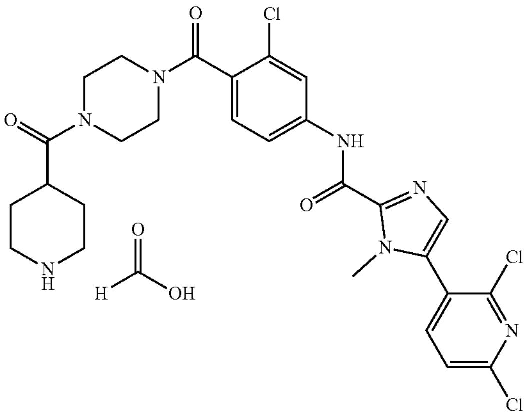 | 604.0 | Intermediate D2 and (2,6-dichloropyridin-3-yl)boronic acid |

-continued

| Ex# | Name | Structure | MS ESI [M + H]+ | Starting Material |
|---|---|---|---|---|
| Example A6 | N-[3-chloro-4-[4-(piperidine-4-carbonyl)piperazine-1-carbonyl]phenyl]-5-[6-(dimethylamino)-2-(trifluoromethyl)-3-pyridyl]-1-methyl-imidazole-2-carboxamide; formic acid | 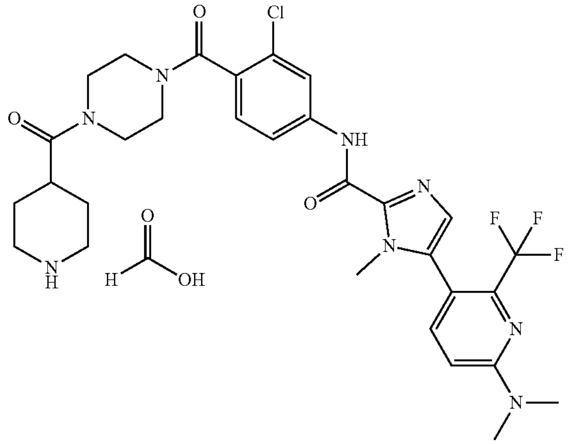 | 647.2 | Intermediate D2 and Intermediate F2 |
| Example A7 | N-[3-chloro-4-[4-(piperidine-4-carbonyl)piperazine-1-carbonyl]phenyl]-5-(2,6-dimethoxy-3-pyridyl)-1-methyl-imidazole-2-carboxamide; formic acid | 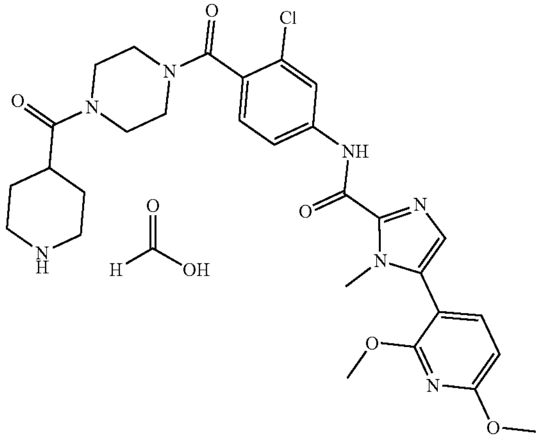 | 596.2 | Intermediate D2 and 2,6-dimethoxy-3-(4,4,5,5-tetramethyl-1,3,2-dioxaborolan-2-yl)pyridine |
| Example A8 | 5-(5-chloro-2-methoxy-4-pyridyl)-N-[3-chloro-4-[4-(piperidine-4-carbonyl)piperazine-1-carbonyl]phenyl]-1-methyl-imidazole-2-carboxamide; formic acid | 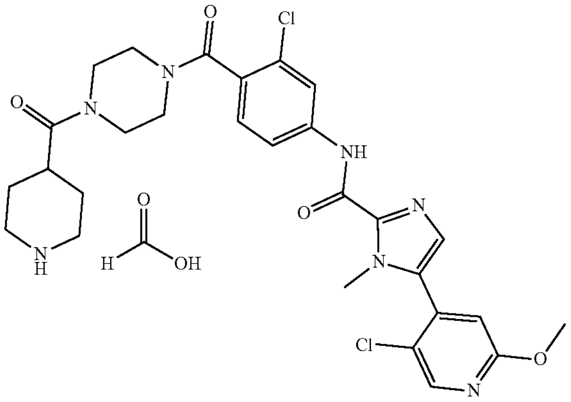 | 600.2 | Intermediate D2 and 5-chloro-2-methoxy-4-(4,4,5,5-tetramethyl-1,3,2-dioxaborolan-2-yl)pyridine |

-continued

| Ex# | Name | Structure | MS ESI [M + H]+ | Starting Material |
|---|---|---|---|---|
| Example A9 | N-[3-chloro-4-[4-[2-[(3S)-pyrrolidin-3-yl]acetyl]piperazine-1-carbonyl]phenyl]-5-[2-(dimethylamino)-4-(trifluoromethyl)pyrimidin-5-yl]-1-methyl-imidazole-2-carboxamide; formic acid | 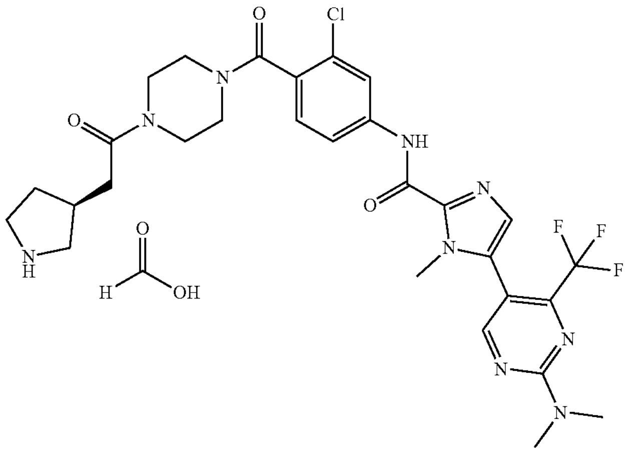 | 648.1 | Intermediate D1 and Intermediate F3 |
| Example A10 | N-[3-chloro-4-[4-(piperidine-4-carbonyl)piperazine-1-carbonyl]phenyl]-5-[2-methoxy-4-(trifluoromethyl)pyrimidin-5-yl]-1-methyl-imidazole-2-carboxamide; formic acid | 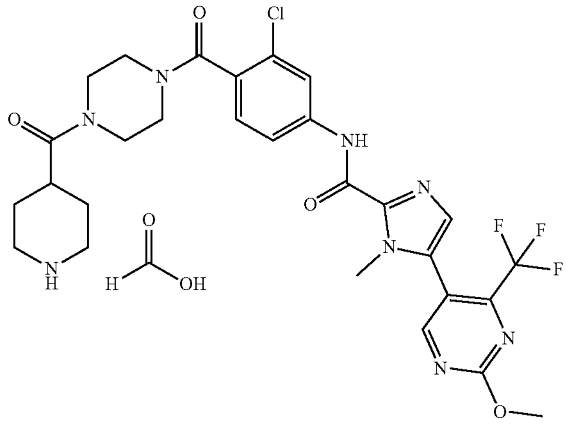 | 635.2 | Intermediate D2 and Intermediate F4 |
| Example A11 | 5-(5-chloro-1H-indol-4-yl)-N-[3-chloro-4-[4-[2-[(3S)-pyrrolidin-3-yl]acetyl]piperazine-1-carbonyl]phenyl]-1-methyl-imidazole-2-carboxamide; formic acid | 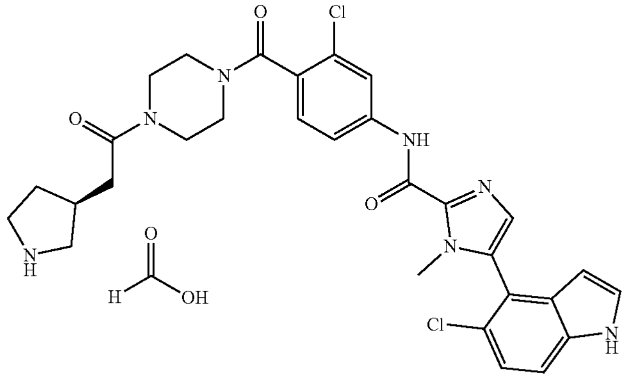 [SMILES: Cn1c(-c2c(Cl)ccc3[nH]ccc23)cnc1C(=O)Nc1ccc(C(=O)N2CCN(C(=O)C[C@@H]3CCNC3)CC2)c(Cl)c1 ; O=CO] | 608.0 | Intermediate D1 and Intermediate E5 |

-continued

| Ex# | Name | Structure | MS ESI [M + H]+ | Starting Material |
|---|---|---|---|---|
| Example A12 | N-[3-chloro-4-[4-(piperidine-4-carbonyl)piperazine-1-carbonyl]phenyl]-5-(1H-indol-4-yl)-1-methyl-imidazole-2-carboxamide; formic acid | 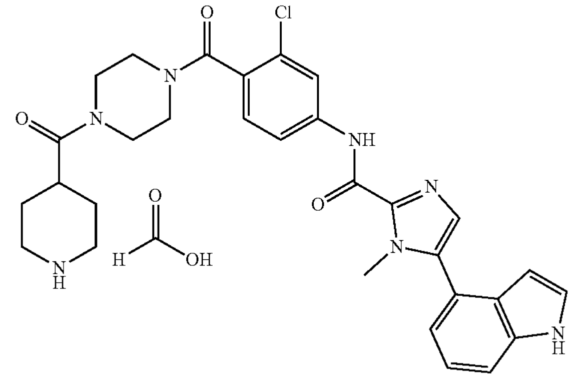 | 574.0 | Intermediate D2 and tert-butyl 4-(4,4,5,5-tetramethyl-1,3,2-dioxaborolan-2-yl)-1H-indole-1-carboxylate |
| Example A13 | N-[3-chloro-4-[4-(piperidine-4-carbonyl)piperazine-1-carbonyl]phenyl]-1-methyl-5-(1-methylindol-4-yl)imidazole-2-carboxamide; formic acid | 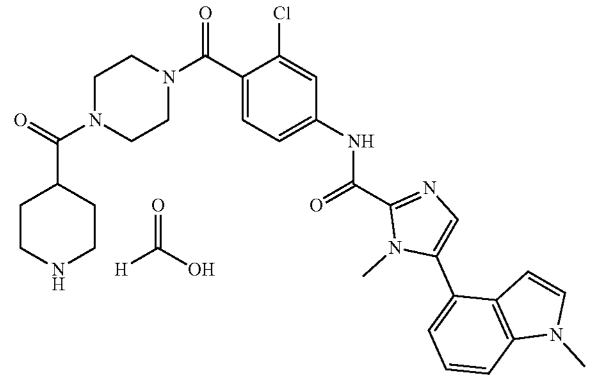 | 588.0 | Intermediate D2 and Intermediate E6 |
| Example A14 | N-[3-chloro-4-[4-[2-[(3S)-pyrrolidin-3-yl]acetyl]piperazine-1-carbonyl]phenyl]-5-[6-methoxy-2-(trifluoromethyl)-3-pyridyl]-1-methyl-imidazole-2-carboxamide; formic acid | 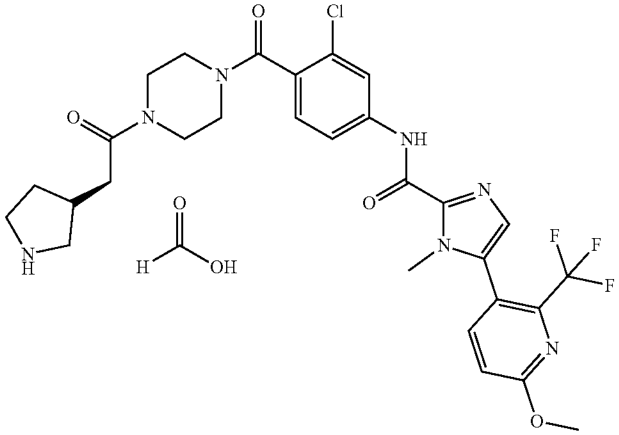 | 634.1 | Intermediate D1 and Intermediate F7 |

-continued

| Ex# | Name | Structure | MS ESI [M + H]+ | Starting Material |
|---|---|---|---|---|
| Example A15 | 5-(4-chloro-6-methoxy-3-pyridyl)-N-[3-chloro-4-[4-(piperidine-4-carbonyl)piperazine-1-carbonyl]phenyl]-1-methyl-imidazole-2-carboxamide; 2,2,2-trifluoroacetic acid | 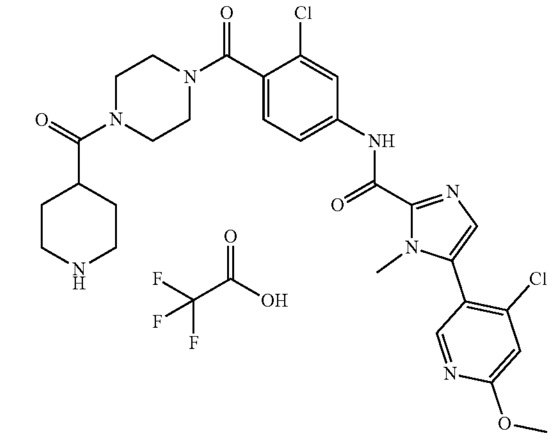 | 600.2 | Intermediate D2 and Intermediate F5 |
| Example A16 | N-[3-chloro-4-[4-(piperidine-4-carbonyl)piperazine-1-carbonyl]phenyl]-5-[6-methoxy-2-(trifluoromethyl)-3-pyridyl]-1-methyl-imidazole-2-carboxamide; formic acid | 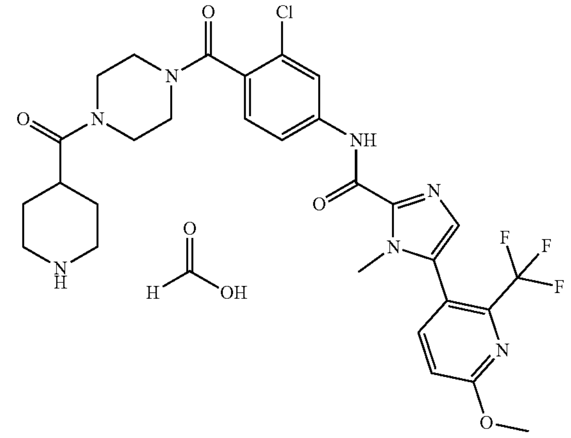 [SMILES: COc1ccc(-c2cnc(C(=O)Nc3ccc(C(=O)N4CCN(C(=O)C5CCNCC5)CC4)c(Cl)c3)n2C)c(C(F)(F)F)n1 ; O=CO] | 634.3 | Intermediate D2 and Intermediate F7 |
| Example A17 | N-[3-chloro-4-[4-[(2S,4R)-4-hydroxypyrrolidine-2-carbonyl]piperazine-1-carbonyl]phenyl]-5-[6-methoxy-2-(trifluoromethyl)-3-pyridyl]-1-methyl-imidazole-2-carboxamide; formic acid | 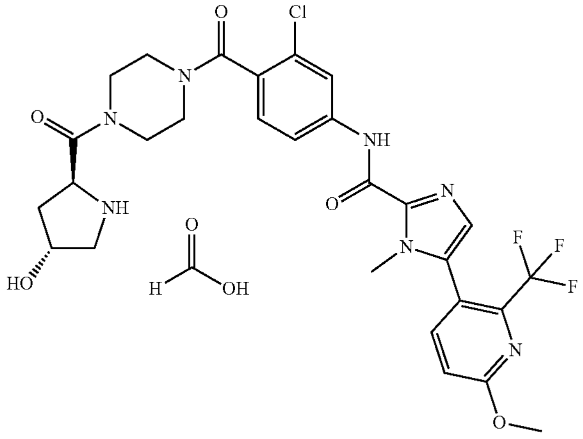 [SMILES: COc1ccc(-c2cnc(C(=O)Nc3ccc(C(=O)N4CCN(C(=O)[C@@H]5C[C@@H](O)CN5)CC4)c(Cl)c3)n2C)c(C(F)(F)F)n1 ; O=CO] | 636.1 | Intermediate D3 and Intermediate F7 |

-continued

| Ex# | Name | Structure | MS ESI [M + H]+ | Starting Material |
|---|---|---|---|---|
| Example A18 | N-[4-[4-[(1R,5S)-3-azabicyclo[3.1.0]hexane-6-carbonyl]piperazine-1-carbonyl]-3-chloro-phenyl]-5-[6-methoxy-2-(trifluoromethyl)-3-pyridyl]-1-methyl-imidazole-2-carboxamide; formic acid | 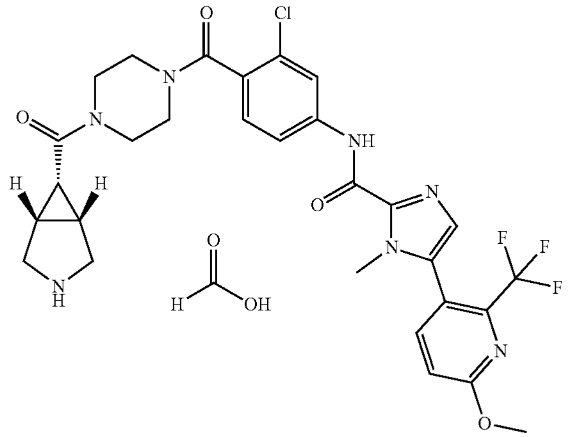 [SMILES: COc1ccc(-c2cnc(C(=O)Nc3ccc(C(=O)N4CCN(C(=O)[C@@H]5[C@@H]6CNC[C@@H]65)CC4)c(Cl)c3)n2C)c(C(F)(F)F)n1 ; O=CO] | 632.1 | Intermediate D4 and Intermediate F7 |
| Example A19 | N-[3-chloro-4-[4-(piperidine-4-carbonyl)piperazine-1-carbonyl]phenyl]-5-[2-(difluoromethyl)-6-methoxy-3-pyridyl]-1-methyl-imidazole-2-carboxamide; 2,2,2-trifluoroacetic acid | 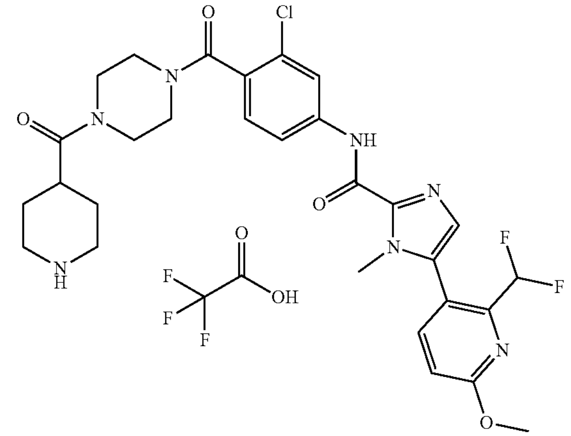 [SMILES: COc1ccc(-c2cnc(C(=O)Nc3ccc(C(=O)N4CCN(C(=O)C5CCNCC5)CC4)c(Cl)c3)n2C)c(C(F)F)n1 ; O=C(O)C(F)(F)F] | 616.3 | Intermediate D2 and Intermediate F6 |
| Example A20 | N-[3-chloro-4-[4-(piperidine-4-carbonyl)piperazine-1-carbonyl]phenyl]-5-(2,3-dihydro-1,4-benzodioxin-6-yl)-1-methyl-imidazole-2-carboxamide | 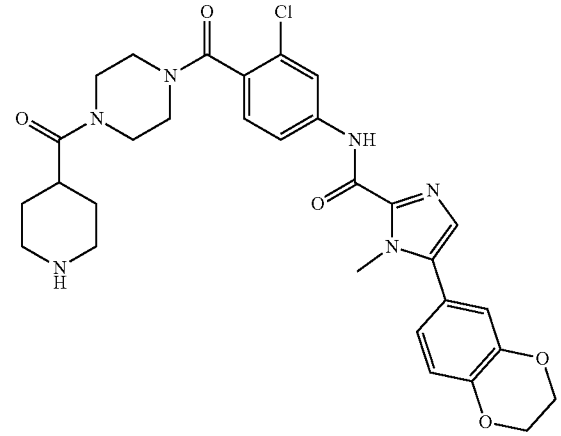 [SMILES: Cn1c(-c2ccc3c(c2)OCCO3)cnc1C(=O)Nc1ccc(C(=O)N2CCN(C(=O)C3CCNCC3)CC2)c(Cl)c1] | 592.2 | Intermediate D2 and 2,3-dihydro-1,4-benzodioxin-6-ylboronic acid |

Example B1

N-[4-(6-aminohexylcarbamoyl)-3-chloro-phenyl]-5-[6-(dimethylamino)-2,5-difluoro-3-pyridyl]-1-methyl-imidazole-2-carboxamide; Formic Acid

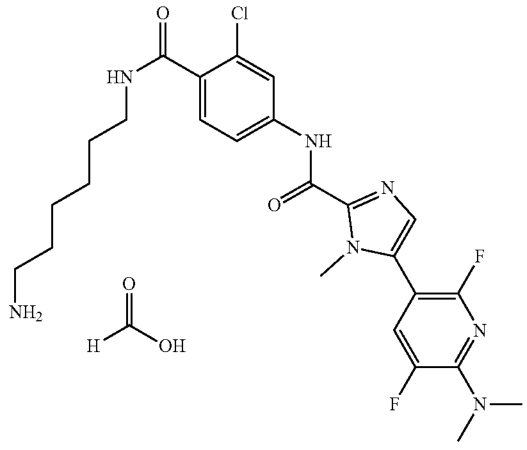 [SMILES: CN(C)c1nc(F)c(-c2cnc(C(=O)Nc3ccc(C(=O)NCCCCCCN)c(Cl)c3)n2C)cc1F ; O=CO]

Step 1: tert-butyl N-[6-[[2-chloro-4-[[5-[6-(dimethylamino)-2,5-difluoro-3-pyridyl]-1-methyl-imidazole-2-carbonyl]amino]benzoyl]amino]hexyl]carbamate A mixture of 2-chloro-4-[[5-[6-(dimethylamino)-2,5-difluoro-3-pyridyl]-1-methyl-imidazole-2-carbonyl]amino] benzoic acid (400 mg, 0.918 mmol), tert-butyl N-(6-aminohexyl)carbamate (297.82 mg, 1.38 mmol), HATU (697.98 mg, 1.84 mmol) and DIPEA (355.88 mg, 2.75 mmol) in DMF (6 mL) was stirred at room temperature for 3 h. Then the mixture was poured into water. The water layer was extracted with DCM. The organic layer was dried over anhydrous $Na_2SO_4$ and concentrated in vacuum to afford the crude product tert-butyl N-[6-[[2-chloro-4-[[5-[6-(dimethylamino)-2,5-difluoro-3-pyridyl]-1-methyl-imidazole-2-carbonyl]amino]benzoyl]amino]hexyl]carbamate. MS $[M+H]^+$: 634.2.

Step 2: N-[4-(6-aminohexylcarbamoyl)-3-chloro-phenyl]-5-[6-(dimethylamino)-2,5-difluoro-3-pyridyl]-1-methyl-imidazole-2-carboxamide; Formic Acid tert-butyl N-[6-[[2-chloro-4-[[5-[6-(dimethylamino)-2,5-difluoro-3-pyridyl]-1-methyl-imidazole-2-carbonyl]amino] benzoyl]amino]hexyl]carbamate (500 mg, 0.788 mmol) was dissolved in dichloromethane (10 mL) and TFA (5 mL) at room temperature. Then the solution was stirred for 1 h. The mixture was concentrated and water was added. The mixture was basified by DIPEA. The water layer was extracted with DCM. The combined organic layers were washed with water, dried over anhydrous $Na_2SO_4$ and concentrated in vacuum to afford the crude product. The residue was purified by Prep-HPLC to afford N-[4-(6-aminohexylcarbamoyl)-3-chloro-phenyl]-5-[6-(dimethylamino)-2,5-difluoro-3-pyridyl]-1-methyl-imidazole-2-carboxamide; formic acid. MS $[M+H]^+$: 534.3.

Example $C_1$

N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide; formic acid

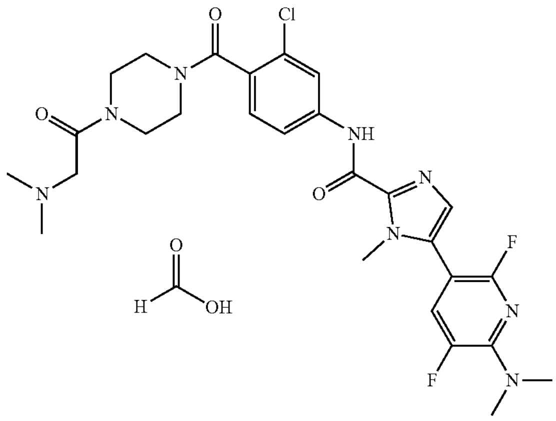

A mixture of N-[3-chloro-4-(piperazine-1-carbonyl)phenyl]-5-[6-(dimethylamino)-2,5-difluoro-3-pyridyl]-1-methyl-imidazole-2-carboxamide (400 mg, 0.794 mmol), 2-(dimethylamino)acetic acid (122.78 mg, 1.19 mmol), HATU (603.63 mg, 1.59 mmol) and DIPEA (307.77 mg, 2.38 mmol) in DMF (5 mL) was stirred at room temperature for 3 h. Then the mixture was poured into water. The water layer was extracted with DCM. The organic layer was concentrated and the residue was purified by Prep-HPLC to afford N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide; formic acid. MS $[M+H]^+$: 589.3.

The following intermediates were prepared in analogy of Example C1:

| Ex# | Name | Structure | MS ESI [M + H]+ | Starting Material |
|---|---|---|---|---|
| Example C2 | N-[4-[4-[2-(dimethylamino) acetyl]piperazine-1-carbonyl]-3-methyl-phenyl]-5-[6-(dimethylamino)-2,5-difluoro-3-pyridyl]-1-methyl-imidazole-2-carboxamide; formic acid | 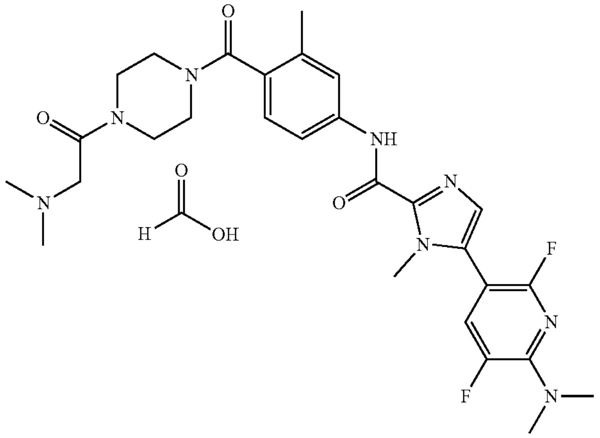 | 569.6 | Intermediate I2 and 2-(dimethyl-amino) acetic acid |
| Example C3 | N-[3-chloro-4-[[3-[[2-(dimethylamino) acetyl]amino] cyclobutyl] carbamoyl] phenyl]-5-[6-(dimethylamino)-2,5-difluoro-3-pyridyl]-1-methyl-imidazole-2-carboxamide; formic acid | 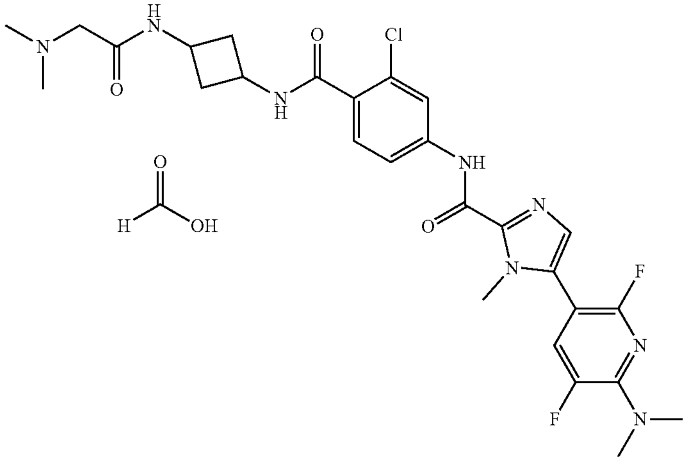 | 589.2 | Intermediate L2 and 2-(dimethyl-amino) acetic acid |
| Example C4 | N-[3-chloro-4-[4-[[2-(dimethylamino) acetyl]amino] piperidine-1-carbonyl] phenyl]-5-[6-(dimethylamino)-2,5-difluoro-3-pyridyl]-1-methyl-imidazole-2-carboxamide; formic acid | 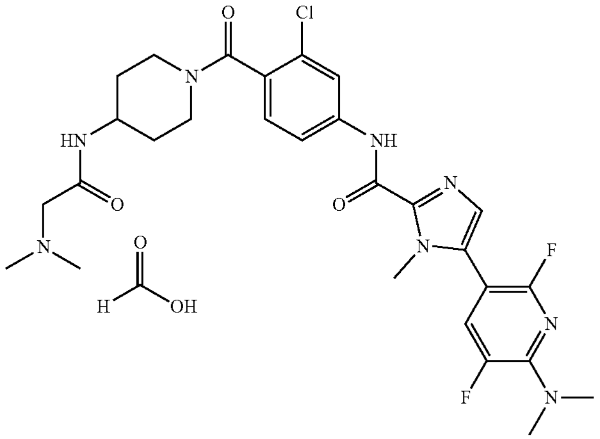 | 603.2 | Intermediate L3 and 2-(dimethyl-amino) acetic acid |

Example D1

[2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]-trimethyl-ammonium; formate

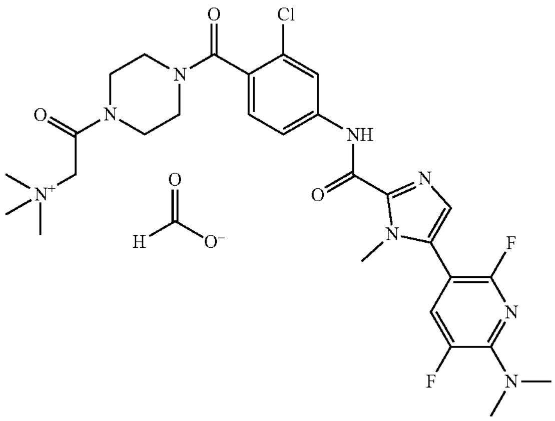

At room temperature, a mixture of N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide (200 mg, 0.340 mmol), iodomethane (481.94 mg, 3.4 mmo) and DIPEA (438.82 mg, 3.4 mmol) in acetonitrile (5 mL) was stirred for 3 h. Then the mixture was concentrated and the residue was purified by Prep-HPLC to afford [2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]-trimethyl-ammonium; formate. MS [M+H]$^+$: 603.3.

The following intermediates were prepared in analogy of Example D1:

| Ex# | Name | Structure | MS ESI [M]$^+$ | Starting Material |
|---|---|---|---|---|
| Example D2 | [2-[4-[4-[[5-[6-(dimethylamino)-2,5-difluoro-3-pyridyl]-1-methyl-imidazole-2-carbonyl]amino]-2-methyl-benzoyl]piperazin-1-yl]-2-oxo-ethyl]-trimethyl-ammonium; formate | 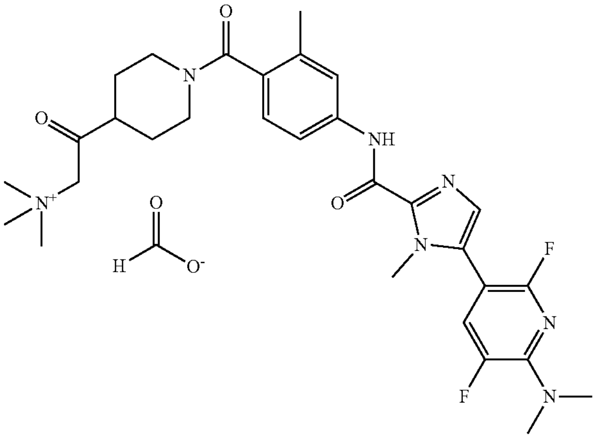 | 583.6 | Intermediate J2 and iodomethane |
| Example D3 | 6-[[2-chloro-4-[[5-[6-(dimethylamino)-2,5-difluoro-3-pyridyl]-1-methyl-imidazole-2-carbonyl]amino]benzoyl]amino]hexyl-trimethyl-ammonium; formate | 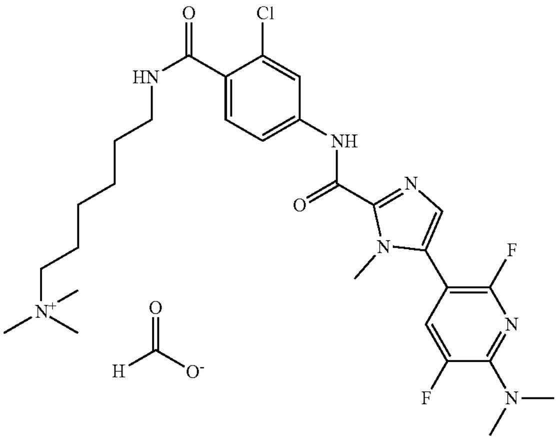 | 577.2 | Intermediate K1 and iodomethane |

-continued

| Ex# | Name | Structure | MS ESI $[M]^+$ | Starting Material |
|---|---|---|---|---|
| Example D4 | N-[3-chloro-4-[4-(1,1-dimethylpiperidin-1-ium-4-carbonyl)piperazine-1-carbonyl]phenyl]-5-[6-(dimethylamino)-2,5-difluoro-3-pyridyl]-1-methyl-imidazole-2-carboxamide; formate | 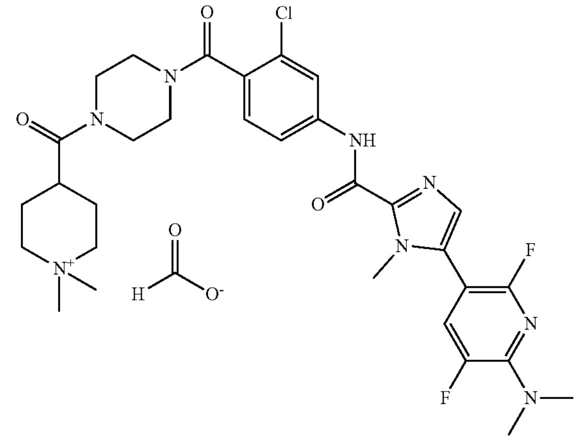 | 644.1 | Example E2 and iodomethane |
| Example D5 | N-[3-chloro-4-[4-(1,1-dimethylpyrrolidin-1-ium-3-carbonyl)piperazine-1-carbonyl]phenyl]-5-[6-(dimethylamino)-2,5-difluoro-3-pyridyl]-1-methyl-imidazole-2-carboxamide; formate | 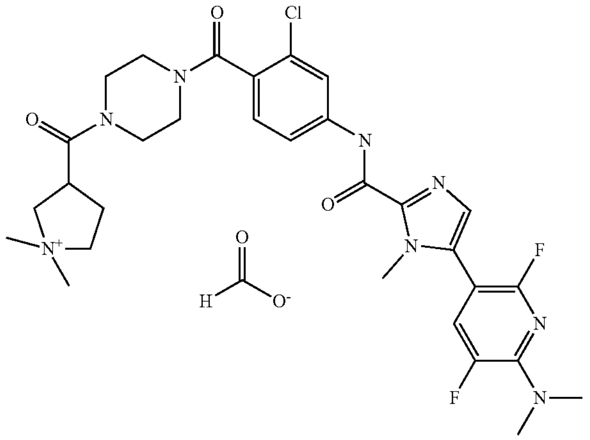 | 629.2 | Intermediate N4 and iodomethane |
| Example D6 | N-[3-chloro-4-[4-[(2S,4R)-4-hydroxy-1,1-dimethyl-pyrrolidin-1-ium-2-carbonyl]piperazine-1-carbonyl]phenyl]-5-[6-(dimethylamino)-2,5-difluoro-3-pyridyl]-1-methyl-imidazole-2-carboxamide; formate | 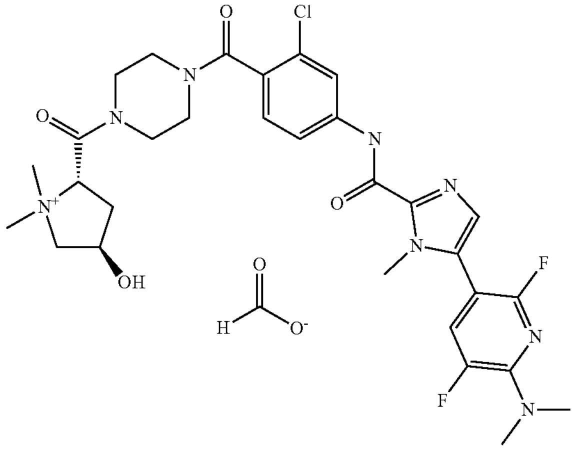 | 645.2 | Intermediate N5 and iodomethane |

-continued

| Ex# | Name | Structure | MS ESI [M]+ | Starting Material |
| --- | --- | --- | --- | --- |
| Example D7 | N-[3-chloro-4-[4-[2-(1,1-dimethylpiperidin-1-ium-4-yl)acetyl]piperazine-1-carbonyl]phenyl]-5-[6-(dimethylamino)-2,5-difluoro-3-pyridyl]-1-methyl-imidazole-2-carboxamide; formate | 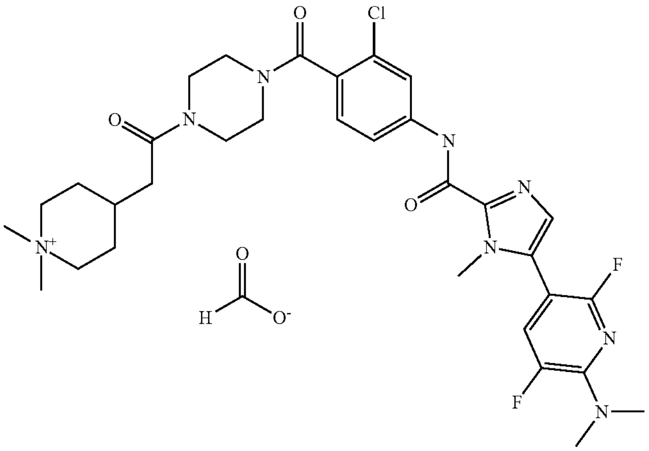 | 657.2 | Intermediate N6 and iodomethane |
| Example D8 | [2-[[3-[[2-chloro-4-[[5-[6-(dimethylamino)-2,5-difluoro-3-pyridyl]-1-methyl-imidazole-2-carbonyl]amino] benzoyl]amino] cyclobutyl]amino]-2-oxo-ethyl]-trimethyl-ammonium; formate | 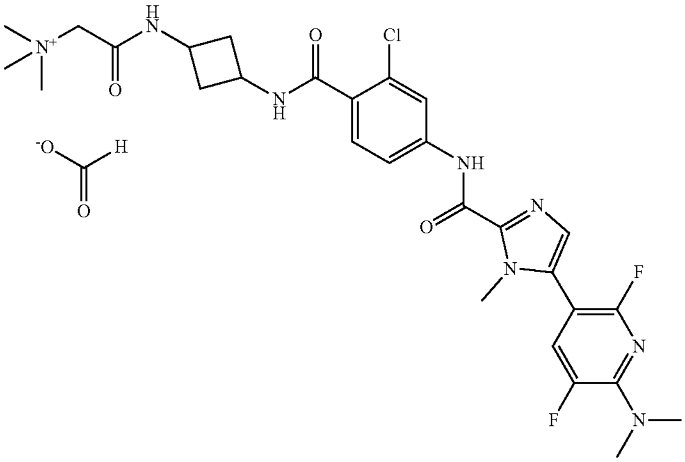 | 603.2 | Example G1 and iodomethane |
| Example D9 | [2-[[1-[2-chloro-4-[[5-[6-(dimethylamino)-2,5-difluoro-3-pyridyl]-1-methyl-imidazole-2-carbonyl]amino] benzoyl]-4-piperidyl]amino]-2-oxo-ethyl]-trimethyl-ammonium; formate | 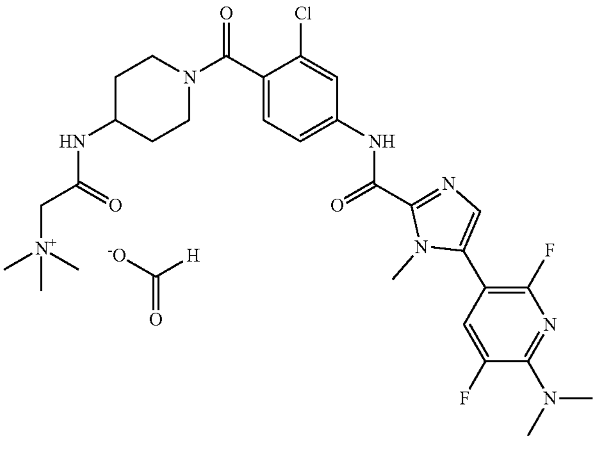 | 617.2 | Example G2 and iodomethane |

-continued

| Ex# | Name | Structure | MS ESI $[M]^+$ | Starting Material |
|---|---|---|---|---|
| Example D10 | 2-[3-[4-[[2-chloro-4-[[5-[6-(dimethylamino)-2,5-difluoro-3-pyridyl]-1-methyl-imidazole-2-carbonyl]amino]benzoyl]amino]-1-piperidyl]-3-oxo-propoxy]ethyl-trimethyl-ammonium; formate | 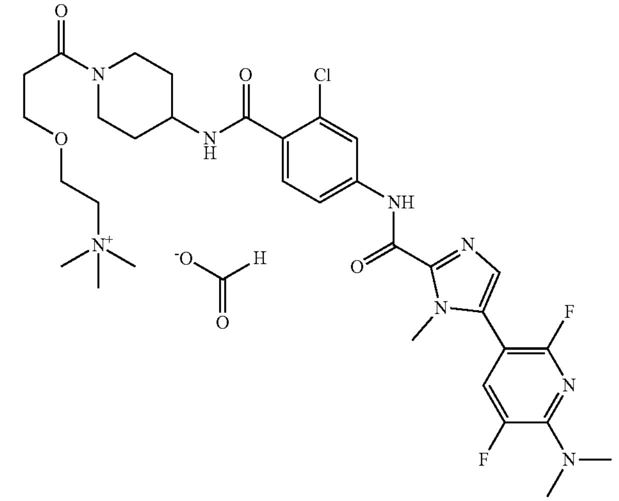 | 675.2 | Intermediate N1 and iodomethane |
| Example D11 | [3-[4-[2-chloro-4-[[5-[6-(dimethylamino)-2,5-difluoro-3-pyridyl]-1-methyl-imidazole-2-carbonyl]amino]benzoyl]piperazine-1-carbonyl]cyclobutyl]methyl-trimethyl-ammonium; 2,2,2-trifluoroacetate | 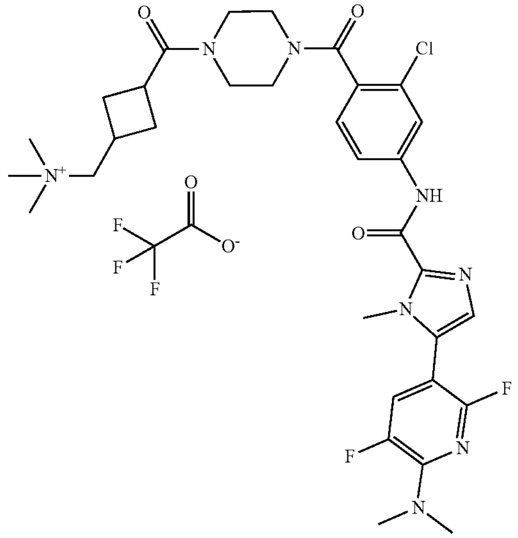 [SMILES: CN(C)c1nc(F)c(-c2cnc(C(=O)Nc3ccc(C(=O)N4CCN(C(=O)C5CC(C[N+](C)(C)C)C5)CC4)c(Cl)c3)n2C)cc1F ; O=C([O-])C(F)(F)F] | 657.3 | Example F7 and iodomethane |
| Example D12 | N-[3-chloro-4-[[1-[(2S,4R)-4-hydroxy-1,1-dimethyl-pyrrolidin-1-ium-2-carbonyl]-4-piperidyl]carbamoyl]phenyl]-5-[6-(dimethylamino)-2,5-difluoro-3-pyridyl]-1-methyl-imidazole-2-carboxamide; formate | 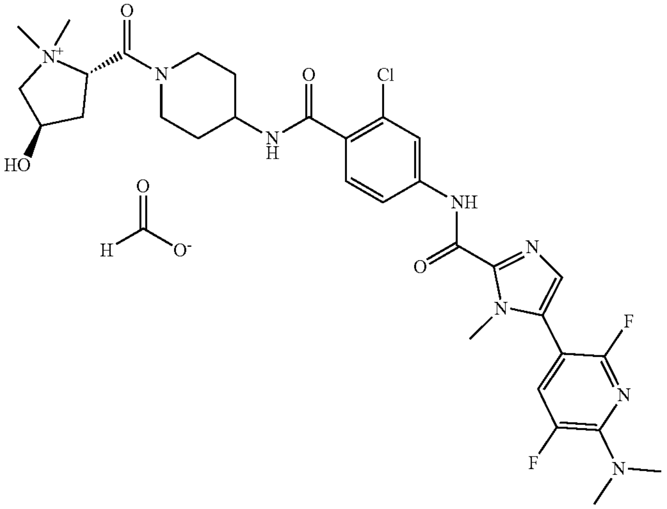 | 659.4 | Intermediate N2 and iodomethane |

-continued

| Ex# | Name | Structure | MS ESI $[M]^+$ | Starting Material |
|---|---|---|---|---|
| Example D13 | 1-[2-chloro-4-[[5-[6-(dimethylamino)-2,5-difluoro-3-pyridyl]-1-methyl-imidazole-2-carbonyl]amino]benzoyl]-N-(1,1-dimethylpyrrolidin-1-ium-3-yl)piperidine-4-carboxamide; formate | 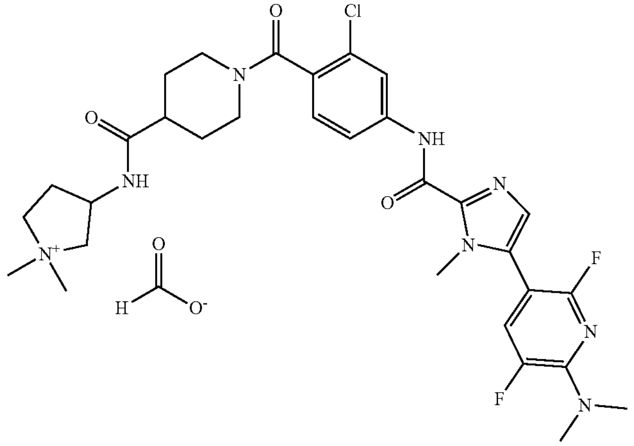 | 643.4 | Intermediate N3 and iodomethane |

Example E1

N-[3-chloro-4-[4-(piperidine-4-carbonyl)piperazine-1-carbonyl]phenyl]-5-[2,5-difluoro-6-(methylamino)-3-pyridyl]-1-methyl-imidazole-2-carboxamide; Formic Acid

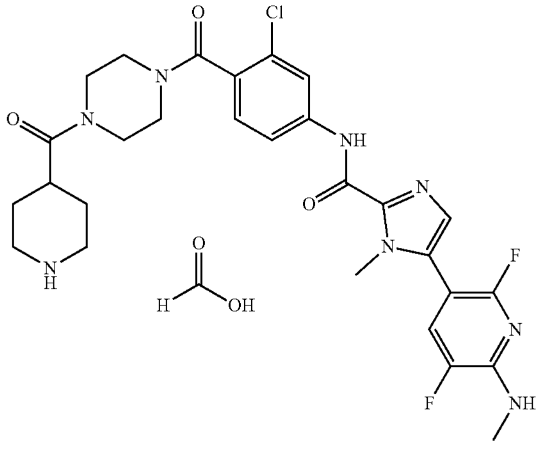 [SMILES: CNc1nc(F)c(-c2cnc(C(=O)Nc3ccc(C(=O)N4CCN(C(=O)C5CCNCC5)CC4)c(Cl)c3)n2C)cc1F ; O=CO]

Step 1: tert-butyl 4-[4-[2-chloro-4-[[1-methyl-5-(2,5,6-trifluoro-3-pyridyl)imidazole-2-carbonyl]amino]benzoyl]piperazine-1-carbonyl]piperidine-1-carboxylate To a 25 mL microwave vial was added tert-butyl 4-[4-[4-[(5-bromo-1-methyl-imidazole-2-carbonyl)amino]-2-chloro-benzoyl]piperazine-1-carbonyl]piperidine-1-carboxylate (500 mg, 784 μmol), 2,3,6-trifluoro-5-(4,4,5,5-tetramethyl-1,3,2-dioxaborolan-2-yl)pyridine (223 mg, 861 μmol), $Na_2CO_3$ (249 mg, 2.35 mmol) and 1,1'-bis(di-tert-butylphosphino)ferrocene palladium dichloride (46.7 mg, 78.4 μmol) in Dioxane (10 mL)/Water (1 mL). The vial was capped and heated in the microwave at 100° C. for 2 h under $N_2$. The crude reaction mixture was concentrated in vacuum. The crude material was purified by flash. To afford tert-butyl 4-[4-[2-chloro-4-[[1-methyl-5-(2,5,6-trifluoro-3-pyridyl)imidazole-2-carbonyl]amino]benzoyl]piperazine-1-carbonyl]piperidine-1-carboxylate (275 mg). MS $[M\text{-boc}]^+$: 590.2.

Step 2: tert-butyl 4-[4-[2-chloro-4-[[5-[2,5-difluoro-6-(methylamino)-3-pyridyl]-1-methyl-imidazole-2-carbonyl]amino]benzoyl]piperazine-1-carbonyl]piperidine-1-carboxylate In a 100 mL round-bottomed flask, tert-butyl 4-[4-[2-chloro-4-[[1-methyl-5-(2,5,6-trifluoro-3-pyridyl)imidazole-2-carbonyl]amino]benzoyl]piperazine-1-carbonyl]piperidine-1-carboxylate (91 mg, 132 μmol) was combined with MeOH (5 mL) to give a light brown solution. Methanamine (659 μl, 1.32 mmol) was added. The reaction was stirred at room temperature for 1 h. The crude reaction mixture was concentrated in vacuum. the reaction was directly used to the next step, to afford tert-butyl 4-[4-[2-chloro-4-[[5-[2,5-difluoro-6-(methylamino)-3-pyridyl]-1-methyl-imidazole-2-carbonyl]amino]benzoyl]piperazine-1-carbonyl]piperidine-1-carboxylate (92.5 mg). MS $[M+H]^+$: 701.6.

Step 3: N-[3-chloro-4-[4-(piperidine-4-carbonyl)piperazine-1-carbonyl]phenyl]-5-[2,5-difluoro-6-(methylamino)-3-pyridyl]-1-methyl-imidazole-2-carboxamide; Formic Acid In a 100 mL round-bottomed flask, tert-butyl 4-[4-[2-chloro-4-[[5-[2,5-difluoro-6-(methylamino)-3-pyridyl]-1-methyl-imidazole-2-carbonyl]amino]benzoyl]piperazine-1-carbonyl]piperidine-1-carboxylate (92.45 mg, 132 mol) was combined with THF (4 mL) to give a light brown solution. HCl (in water) (1.1 ml, 13.2 mmol) was added. The reaction was stirred at room temperature for 30 min. The crude reaction mixture was concentrated in vacuum. The crude material was purified by preparative HPLC. to afford N-[3-chloro-4-[4-(piperidine-4-carbonyl)piperazine-1-carbonyl]phenyl]-5-[2,5-difluoro-6-(methylamino)-3-pyridyl]-1-methyl-imidazole-2-carboxamide; formic acid (19 mg). MS $[M+H]^+$: 601.3.

The following intermediates were prepared in analogy of Example E1:

| Ex# | Name | Structure | MS ESI [M + H]+ | Starting Material |
|---|---|---|---|---|
| Example E2 | N-[3-chloro-4-[4-(piperidine-4-carbonyl)piperazine-1-carbonyl]phenyl]-5-[6-(dimethylamino)-2,5-difluoro-3-pyridyl]-1-methyl-imidazole-2-carboxamide; formic acid | 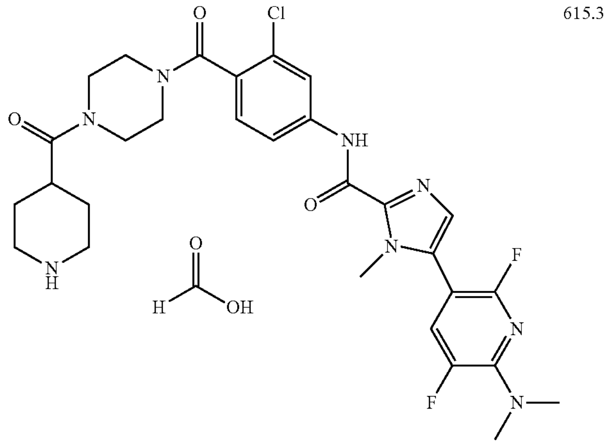 | 615.3 | Intermediate D2; Intermediate F1 and N-methylmethanamine |
| Example E3 | N-[3-chloro-4-[4-(piperidine-4-carbonyl)piperazine-1-carbonyl]phenyl]-5-[6-(dimethylamino)-2-fluoro-3-pyridyl]-1-methyl-imidazole-2-carboxamide; formic acid | 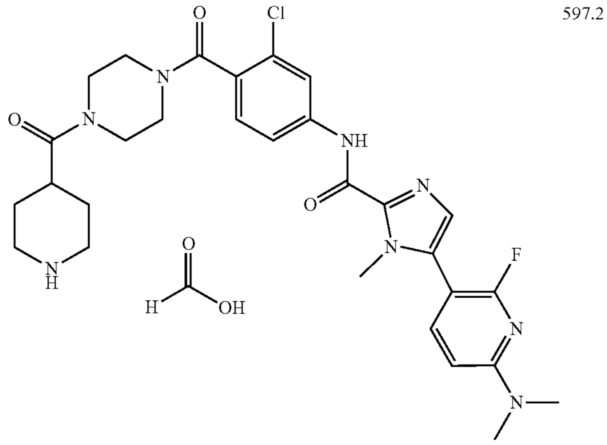 | 597.2 | Intermediate D2; (2,6-difluoro-3-pyridyl)boronic acid and N-methylmethanamine |

-continued

| Ex# | Name | Structure | MS ESI $[M + H]^+$ | Starting Material |
|---|---|---|---|---|
| Example E4 | N-[3-chloro-4-[4-(piperidine-4-carbonyl)piperazine-1-carbonyl]phenyl]-5-[6-(dimethylamino)-2-methyl-3-pyridyl]-1-methyl-imidazole-2-carboxamide; formic acid | 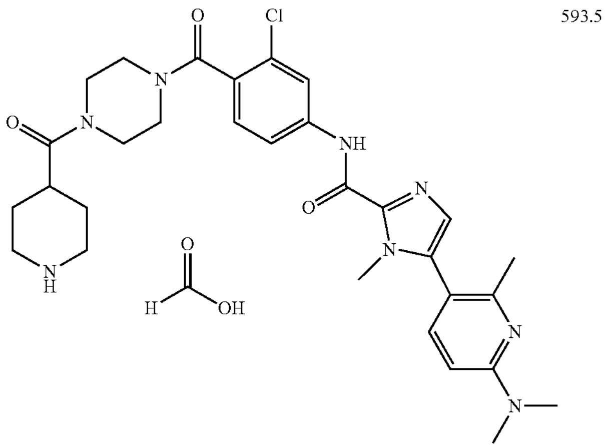 | 593.5 | Intermediate D2; (6-fluoro-2-methyl-3-pyridyl)boronic acid and N-methylmethanamine |
| Example E5 | 5-[2-chloro-6-(dimethylamino)-3-pyridyl]-N-[3-chloro-4-[4-(piperidine-4-carbonyl)piperazine-1-carbonyl]phenyl]-1-methyl-imidazole-2-carboxamide; formic acid | 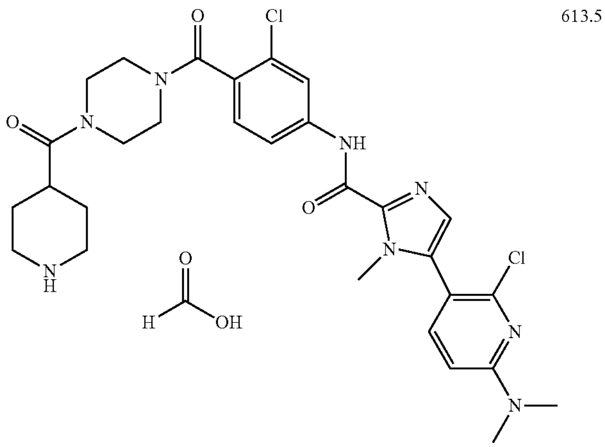 | 613.5 | Intermediate D2; (2,6-dichloro-3-pyridyl)boronic acid and N-methylmethanamine |

Example F1

N-[3-chloro-4-[4-(4-hydroxypiperidine-4-carbonyl) piperazine-1-carbonyl]phenyl]-5-[6-(dimethyl-amino)-2,5-difluoro-3-pyridyl]-1-methyl-imidazole-2-carboxamide; Formic Acid

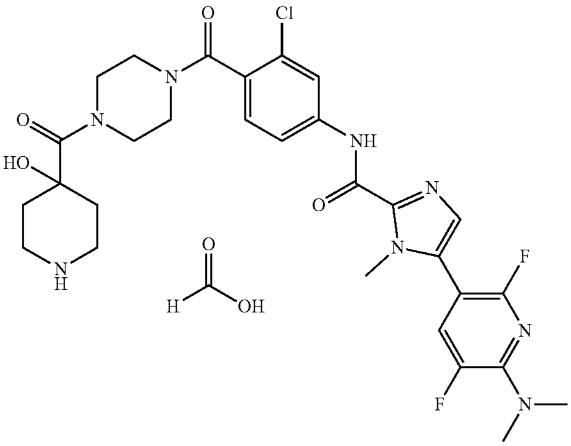 [SMILES: CN(C)c1nc(F)c(-c2cnc(C(=O)Nc3ccc(C(=O)N4CCN(C(=O)C5(O)CCNCC5)CC4)c(Cl)c3)n2C)cc1F ; O=CO]

In a 100 mL round-bottomed flask, tert-butyl 4-[4-[2-chloro-4-[[5-[6-(dimethylamino)-2,5-difluoro-3-pyridyl]-1-methyl-imidazole-2-carbonyl]amino]benzoyl]piperazine-1-carbonyl]-4-hydroxy-piperidine-1-carboxylate (110 mg, 150 μmol) was combined with THF (3 mL) to give a light brown solution. HCl (in water) (1.25 ml, 15 mmol) was added. The reaction was stirred at room temperature for 1 h. The crude reaction mixture was concentrated in vacuum. The crude material was purified by preparative HPLC. to afford N-[3-chloro-4-[4-(4-hydroxypiperidine-4-carbonyl)piperazine-1-carbonyl]phenyl]-5-[6-(dimethylamino)-2,5-difluoro-3-pyridyl]-1-methyl-imidazole-2-carboxamide; formic acid (25 mg). MS $[M+H]^+$: 631.1.

The following intermediates were prepared in analogy of Example F1:

| Ex# | Name | Structure | MS ESI $[M + H]^+$ | Starting Material |
|---|---|---|---|---|
| Example F2 | N-[3-chloro-4-[4-[2-[(3S)-pyrrolidin-3-yl]acetyl]piperazine-1-carbonyl]phenyl]-5-[6-(dimethylamino)-2,5-difluoro-3-pyridyl]-1-methyl-imidazole-2-carboxamide; formic acid | 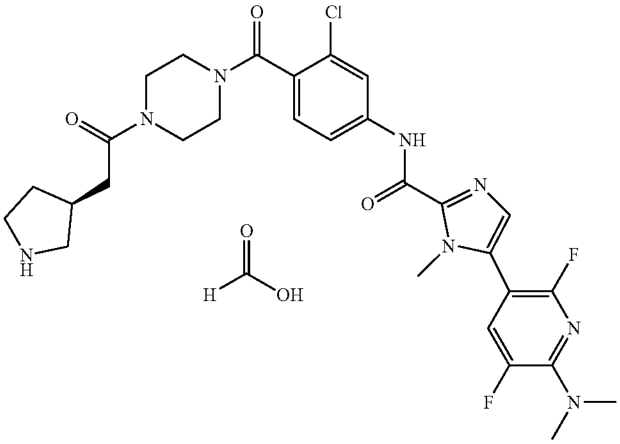 [SMILES: CN(C)c1nc(F)c(-c2cnc(C(=O)Nc3ccc(C(=O)N4CCN(C(=O)C[C@@H]5CCNC5)CC4)c(Cl)c3)n2C)cc1F ; O=CO] | 614.9 | Intermediate J4 and HCl |
| Example F3 | N-[3-chloro-4-[4-[2-(4-hydroxy-4-piperidyl)acetyl] piperazine-1-carbonyl]phenyl]-5-[6-(dimethylamino)-2,5-difluoro-3-pyridyl]-1-methyl-imidazole-2-carboxamide; formic acid | 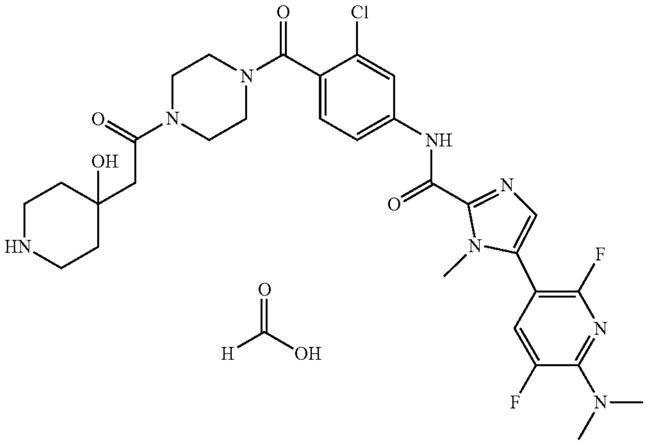 [SMILES: CN(C)c1nc(F)c(-c2cnc(C(=O)Nc3ccc(C(=O)N4CCN(C(=O)CC5(O)CCNCC5)CC4)c(Cl)c3)n2C)cc1F ; O=CO] | 645.1 | Intermediate J5 and HCl |

-continued

| Ex# | Name | Structure | MS ESI [M + H]+ | Starting Material |
|---|---|---|---|---|
| Example F4 | N-[3-chloro-4-[4-(pyrrolidine-3-carbonyl)piperazine-1-carbonyl]phenyl]-5-[6-(dimethylamino)-2,5-difluoro-3-pyridyl]-1-methyl-imidazole-2-carboxamide; formic acid | 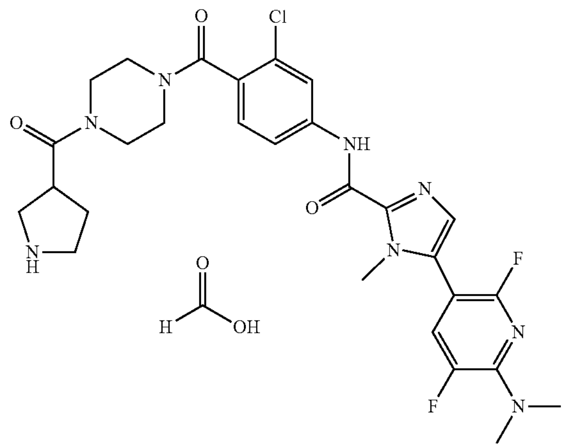 [SMILES: CN(C)c1nc(F)c(-c2cnc(C(=O)Nc3ccc(C(=O)N4CCN(C(=O)C5CCNC5)CC4)c(Cl)c3)n2C)cc1F ; O=CO] | 601.2 | Intermediate J6 and HCl |
| Example F5 | N-[3-chloro-4-[4-[(2S,4R)-4-hydroxypyrrolidine-2-carbonyl]piperazine-1-carbonyl]phenyl]-5-[6-(dimethylamino)-2,5-difluoro-3-pyridyl]-1-methyl-imidazole-2-carboxamide; formic acid | 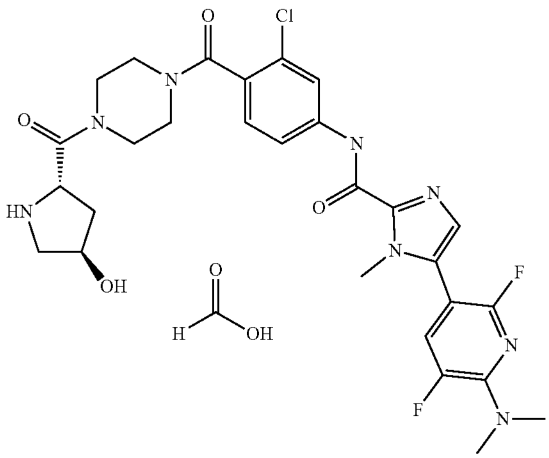 [SMILES: CN(C)c1nc(F)c(-c2cnc(C(=O)Nc3ccc(C(=O)N4CCN(C(=O)[C@@H]5C[C@@H](O)CN5)CC4)c(Cl)c3)n2C)cc1F ; O=CO] | 617.4 | Intermediate J7 and HCl |
| Example F6 | N-[3-chloro-4-[4-[2-(4-piperidyl)acetyl]piperazine-1-carbonyl]phenyl]-5-[6-(dimethylamino)-2,5-difluoro-3-pyridyl]-1-methyl-imidazole-2-carboxamide; formic acid | 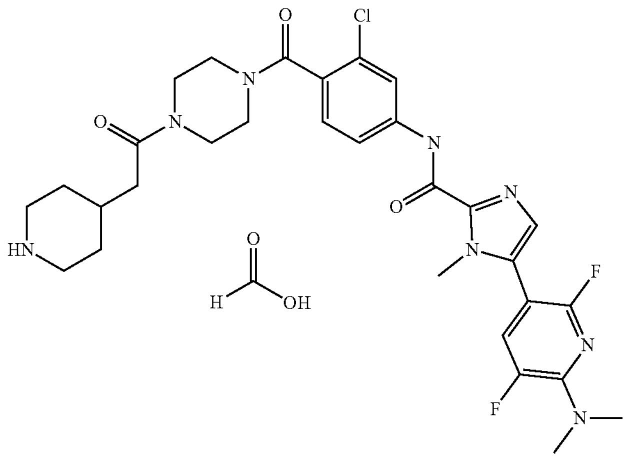 [SMILES: CN(C)c1nc(F)c(-c2cnc(C(=O)Nc3ccc(C(=O)N4CCN(C(=O)CC5CCNCC5)CC4)c(Cl)c3)n2C)cc1F ; O=CO] | 629.4 | Intermediate J8 and HCl |

-continued

| Ex# | Name | Structure | MS ESI [M + H]+ | Starting Material |
|---|---|---|---|---|
| Example F7 | N-[4-[4-[3-(aminomethyl)cyclo-butanecarbonyl]piperazine-1-carbonyl]-3-chloro-phenyl]-5-[6-(dimethylamino)-2,5-difluoro-3-pyridyl]-1-methyl-imidazole-2-carboxamide; formic acid | 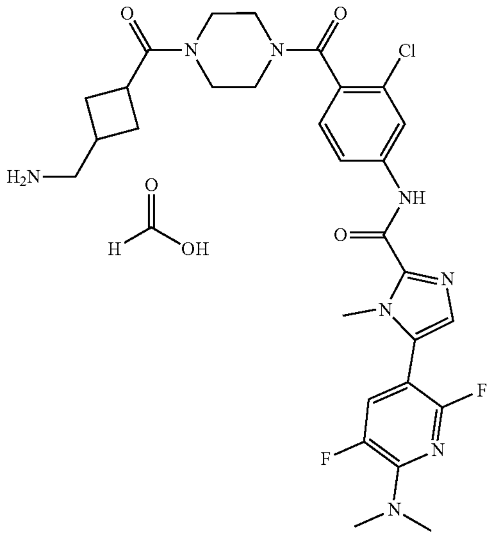 | 615.4 | Intermediate J9 and HCl |
| Example F8 | N-[4-[[1-[3-(2-aminoethoxy)propanoyl]-4-piperidyl]carbamoyl]-3-chloro-phenyl]-5-[6-(dimethylamino)-2,5-difluoro-3-pyridyl]-1-methyl-imidazole-2-carboxamide; formic acid | 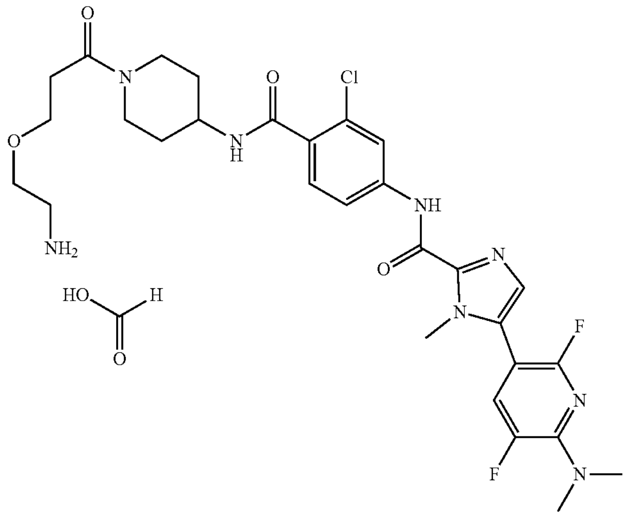 | 633.2 | Intermediate J10 and HCl |
| Example F9 | N-[3-chloro-4-[[1-[(2S,4R)-4-hydroxypyrrolidine-2-carbonyl]-4-piperidyl]carbamoyl]phenyl]-5-[6-(dimethylamino)-2,5-difluoro-3-pyridyl]-1-methyl-imidazole-2-carboxamide; formic acid | 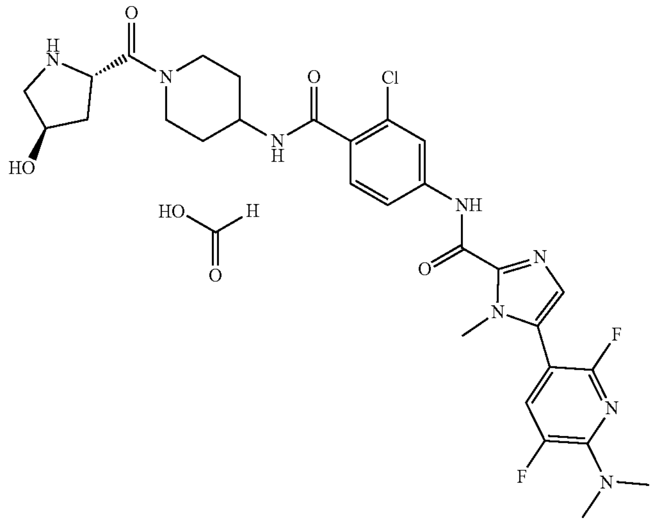 [SMILES: CN(C)c1nc(F)c(-c2cnc(C(=O)Nc3ccc(C(=O)NC4CCN(C(=O)[C@@H]5C[C@@H](O)CN5)CC4)c(Cl)c3)n2C)cc1F ; O=CO] | 631.3 | Intermediate J13 and HCl |

-continued

| Ex# | Name | Structure | MS ESI [M + H]+ | Starting Material |
| --- | --- | --- | --- | --- |
| Example F10 | 1-[2-chloro-4-[[5-[6-(dimethylamino)-2,5-difluoro-3-pyridyl]-1-methyl-imidazole-2-carbonyl]amino]benzoyl]-N-pyrrolidin-3-yl-piperidine-4-carboxamide; formic acid | 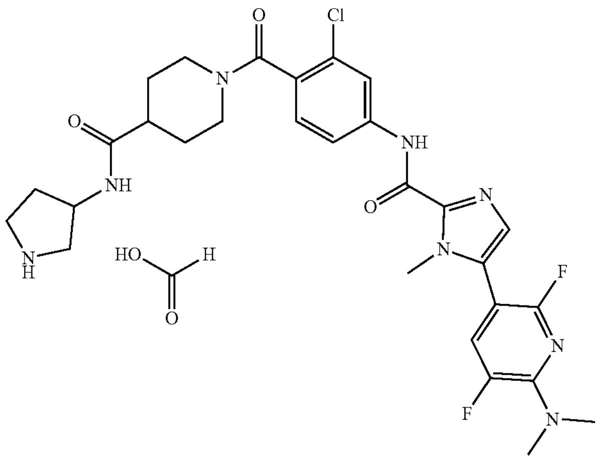 [SMILES: CN(C)c1nc(F)c(-c2cnc(C(=O)Nc3ccc(C(=O)N4CCC(C(=O)NC5CCNC5)CC4)c(Cl)c3)n2C)cc1F ; O=CO] | 615.4 | Intermediate J14 and HCl |

Assay Procedures

Antimicrobial Susceptibility Testing:

90% Growth Inhibitory Concentration (IC90) Determination

The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC17961.

Stock compounds in DMSO were serially twofold diluted (e.g. range from 50 to 0.097 μM final concentration) in 384 wells microtiter plates and inoculated with 49 μl the bacterial suspension in Iso-Sensitest medium to have a final cell concentration of ~$5\times10^5$ CFU/ml in a final volume/well of 50 μl/well. Microtiter plates were incubated at 35±2° C.

Bacterial cell growth was determined with the measurement of optical density at λ=600 nm each 20 minutes over a time course of 16 h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present invention obtained against the strain *Acinetobacter baumannii* ATCC17961.

Particular compounds of the present invention exhibit an IC90 (*Acinetobacter baumannii* ATCC17961)≤25 μmol/l.

More particular compounds of the present invention exhibit an IC90 (*Acinetobacter baumannii* ATCC17961)≤5 μmol/l.

Most particular compounds of the present invention exhibit an IC90 (*Acinetobacter baumannii* ATCC17961)≤1 μmol/l.

TABLE 1

| Ex. | ATCC 17961 IC90 [μM] |
| --- | --- |
| A1 | 0.23 |
| A2 | 0.46 |
| A3 | 0.23 |
| A4 | / |
| A5 | 0.72 |

TABLE 1-continued

| Ex. | ATCC 17961 IC90 [μM] |
| --- | --- |
| A6 | 0.31 |
| A7 | 0.46 |
| A8 | 0.57 |
| A9 | 0.58 |
| A10 | 1.4 |
| A11 | 0.29 |
| A12 | 0.49 |
| A13 | 1.1 |
| A14 | 0.23 |
| A15 | 0.66 |
| A16 | 0.28 |
| A17 | 0.36 |
| A18 | 0.26 |
| A19 | 0.91 |
| A20 | 0.52 |
| B1 | 1.7 |
| C1 | 0.53 |
| C2 | 2.5 |
| C3 | / |
| C4 | / |
| D1 | 0.65 |
| D2 | 1.5 |
| D3 | 4.2 |
| D4 | 0.6 |
| D5 | 0.59 |
| D6 | / |
| D7 | 0.76 |
| D8 | 2.7 |
| D9 | 1.6 |
| D10 | 5.6 |
| D11 | 1.5 |
| D12 | 2.8 |
| D13 | 0.73 |
| E1 | 1.2 |
| E2 | 0.19 |
| E3 | 0.47 |
| E4 | 1.4 |
| E5 | 0.47 |
| F1 | 0.27 |
| F2 | 0.23 |
| F3 | 0.43 |
| F4 | 0.74 |
| F5 | / |
| F6 | 0.66 |
| F7 | 0.39 |
| F8 | / |

TABLE 1-continued

| Ex. | ATCC 17961 IC90 [μM] |
|---|---|
| F9 | 1.9 |
| F10 | 0.64 |

Example 1

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 2

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 3

A compound of formula (I) can be used in a manner known per se as the active ingredient for the production of an infusion solution of the following composition:

| | |
|---|---|
| Active ingredient | 100 mg |
| Lactic acid 90% | 100 mg |
| NaOH q.s. or HCl q.s. for adjustment to pH 4.0 | |
| Sodium chloride q.s. or glucose q.s. for adjustment of the osmolality to 290 mOsm/kg | |
| Water for injection (WFI) | ad 100 ml |

Example 4

A compound of formula (I) can be used in a manner known per se as the active ingredient for the production of an infusion solution of the following composition:

-continued

| | |
|---|---|
| Active ingredient | 100 mg |
| Hydroxypropyl-beta-cyclodextrin | 10 g |
| NaOH q.s. or HCl q.s. for adjustment to pH 7.4 | |
| Sodium chloride q.s. or glucose q.s. for adjustment of the osmolality to 290 mOsm/kg | |
| Water for injection (WFI) | ad 100 ml |

The invention claimed is:

1. A compound of formula (I):

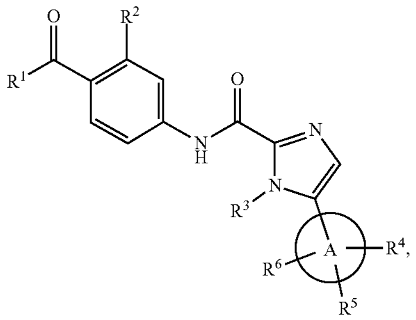

(I)

or a pharmaceutically acceptable salt thereof, wherein:

$R^1$ is selected from:

(i) a group

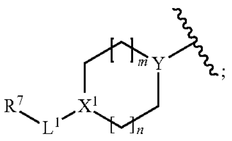

(ii) a group

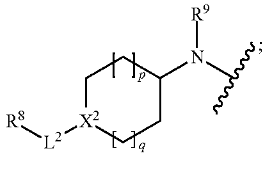

and (iii) a group

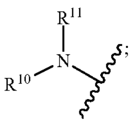

$R^2$ is selected from hydrogen, halogen, cyano, $C_1$-$C_6$-alkyl, $C_1$-$C_6$-alkoxy, halo-$C_1$-$C_6$-alkyl, and halo-$C_1$-$C_6$-alkoxy;

$R^3$ is selected from $C_1$-$C_6$-alkyl and halo-$C_1$-$C_6$-alkyl;

$R^4$, $R^5$, and $R^6$ are each independently selected from hydrogen, halogen, cyano, hydroxy, $C_1$-$C_6$-alkyl, $C_1$-$C_6$-alkoxy, halo-$C_1$-$C_6$-alkyl, halo-$C_1$-$C_6$-alkoxy, amino, $C_1$-$C_6$-alkyl-NH—, and $(C_1$-$C_6$-alkyl$)_2$N—;

$R^7$ is selected from hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, $(C_1$-$C_6$-alkyl$)_3N^+$—$C_1$-$C_6$-alkyl-, amino-$C_1$-$C_6$-alkoxy-$C_1$-$C_6$-alkyl, $C_1$-$C_6$-alkyl-NH—$C_1$-$C_6$-alkoxy-$C_1$-$C_6$-alkyl-, $(C_1$-$C_6$-alkyl$)_2$N—$C_1$-$C_6$-alkoxy-$C_1$-$C_6$-alkyl-, $(C_1$-$C_6$-alkyl$)_3N^+$—$C_1$-$C_6$-alkoxy-$C_1$-$C_6$-alkyl, and a group

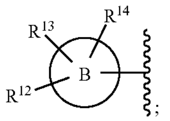

$R^8$ is selected from hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, $(C_1$-$C_6$-alkyl$)_3N^+$—$C_1$-$C_6$-alkyl-, amino-$C_1$-$C_6$-alkoxy-$C_1$-$C_6$-alkyl, $C_1$-$C_6$-alkyl-NH—$C_1$-$C_6$-alkoxy-$C_1$-$C_6$-alkyl-, $(C_1$-$C_6$-alkyl$)_2$N—$C_1$-$C_6$-alkoxy-$C_1$-$C_6$-alkyl-, $(C_1$-$C_6$-alkyl$)_3N^+$—$C_1$-$C_6$-alkoxy-$C_1$-$C_6$-alkyl, and a group

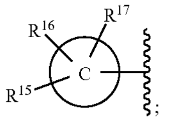

$R^9$ and $R^{11}$ are each independently selected from hydrogen and $C_1$-$C_6$-alkyl;

$R^{10}$ is selected from hydrogen, $C_1$-$C_6$-alkyl, hydroxy-$C_1$-$C_6$-alkyl, amino-$C_1$-$C_6$-alkyl-, $C_1$-$C_6$-alkyl-NH—$C_1$-$C_6$-alkyl-, $(C_1$-$C_6$-alkyl$)_2$N—$C_1$-$C_6$-alkyl-, and $(C_1$-$C_6$-alkyl$)_3N^+$—$C_1$-$C_6$-alkyl-;

$R^{12}$, $R^{13}$, $R^{14}$, $R^{15}$, $R^{16}$, and $R^{17}$ are each independently selected from hydrogen, halogen, cyano, hydroxy, amino, $C_1$-$C_6$-alkyl, $C_1$-$C_6$-alkoxy, halo-$C_1$-$C_6$-alkyl, halo-$C_1$-$C_6$-alkoxy, hydroxy-$C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl$)_2$N—$C_1$-$C_6$-alkyl-, and $(C_1$-$C_6$-alkyl$)_3N^+$—$C_1$-$C_6$-alkyl-;

A is a 5- to 14-membered heteroaryl;

B and C are are each independently selected from 3- to 14-membered heterocycloalkyl, and $C_3$-$C_{10}$-cycloalkyl;

$X^1$, $X^2$, and Y are each independently selected from N and CH;

m, n, p, and q are each independently 0 or 1; and $L^1$ and $L^2$ are each independently selected from carbonyl, —C(O)—$C_1$-$C_6$-alkyl-, —$C_1$-$C_6$-alkyl-C(O)—, —NH—C(O)—, and—C(O)—NH—;

provided that A is not pyrazole.

2. The compound of formula (I) according to claim 1, or a pharmaceutically acceptable salt thereof, wherein:

$R^1$ is selected from:

(i) a group

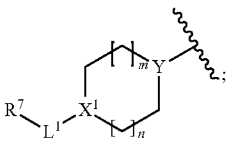

(ii) a group

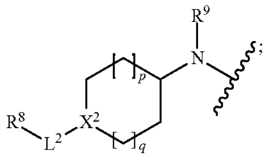

and (iii) a group

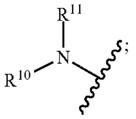

$R^7$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, and a group

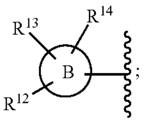

$R^8$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, $(C_1$-$C_6$-alkyl$)_3N^+$—$C_1$-$C_6$-alkoxy-$C_1$-$C_6$-alkyl, and a group

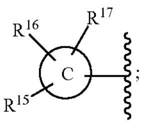

$R^9$ and $R^{11}$ are both hydrogen;

$R^{10}$ is selected from amino-$C_1$-$C_6$-alkyl and $(C_1$-$C_6$-alkyl$)_3$ $N^+$—$C_1$-$C_6$-alkyl-;

$R^{12}$ is selected from hydrogen, hydroxy, amino-$C_1$-$C_6$-alkyl, and $(C_1$-$C_6$-alkyl$)_3N^+$—$C_1$-$C_6$-alkyl-;

$R^{13}$, $R^{14}$, $R^{16}$, and $R^{17}$ are each independently selected from hydrogen and $C_1$-$C_6$-alkyl;

$R^{15}$ is hydroxy;

B is selected from 3- to 14-membered heterocycloalkyl and $C_3$-$C_{10}$-cycloalkyl;

C is 3- to 14-membered heterocycloalkyl;

$L^1$ is selected from carbonyl, —$C_1$-$C_6$-alkyl-C(O)—, —NH—C(O)—, and—C(O)—NH—;

$L^2$ is selected from carbonyl and—C(O)—NH—;

$X^1$ and $X^2$ are each independently selected from N and CH;

Y is N;

m and n are both 1; and p and q are both 0;

or p and q are both 1.

3. The compound of formula (I) according to claim 2, or a pharmaceutically acceptable salt thereof, wherein:

$R^1$ is a group

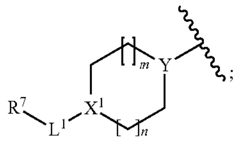

$R^7$ is a group

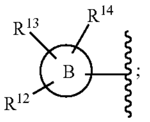

$R^{12}$ is hydrogen or hydroxy;
$R^{13}$ and $R^{14}$ are both hydrogen;
B is a 3- to 14-membered heterocycloalkyl;
$L^1$ is carbonyl or —$C_1$-$C_6$-alkyl-C(O)—;
$X^1$ and Y are both N; and
m and n are both 1.

4. The compound of formula (I) according to claim 3, or a pharmaceutically acceptable salt thereof, wherein:
$R^1$ is a group

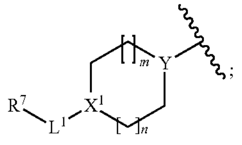

$R^7$ is a group

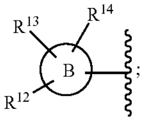

$R^{12}$ is hydrogen or hydroxy;
$R^{13}$ and $R^{14}$ are both hydrogen;
B is piperidine or pyrrolidine;
$L^1$ is carbonyl or —$CH_2$—C(O)—;
$X^1$ and Y are both N; and
m and n are both 1.

5. The compound of formula (I) according to claim 1, or a pharmaceutically acceptable salt thereof, wherein $R^2$ is halogen or $C_1$-$C_6$-alkyl.

6. The compound of formula (I) according to claim 5, or a pharmaceutically acceptable salt thereof, wherein $R^2$ is halogen.

7. The compound of formula (I) according to claim 6, or a pharmaceutically acceptable salt thereof, wherein $R^2$ is chloro.

8. The compound of formula (I) according to claim 1, or a pharmaceutically acceptable salt thereof, wherein $R^3$ is $C_1$-$C_6$-alkyl.

9. The compound of formula (I) according to claim 8, or a pharmaceutically acceptable salt thereof, wherein $R^3$ is methyl.

10. The compound of formula (I) according to claim 1, or a pharmaceutically acceptable salt thereof, wherein:
$R^4$ is selected from hydrogen, halogen, $C_1$-$C_6$-alkyl, $C_1$-$C_6$-alkoxy, $C_1$-$C_6$-alkyl-NH—, ($C_1$-$C_6$-alkyl)$_2$N—, and halo-$C_1$-$C_6$-alkyl;
$R^5$ is selected from hydrogen, $C_1$-$C_6$-alkyl, $C_1$-$C_6$-alkoxy, halogen, and ($C_1$-$C_6$-alkyl)$_2$N—; and
$R^6$ is hydrogen or halogen.

11. The compound of formula (I) according to claim 10, or a pharmaceutically acceptable salt thereof, wherein:
$R^4$ is selected from halogen, ($C_1$-$C_6$-alkyl)$_2$N—, and halo-$C_1$-$C_6$-alkyl;
$R^5$ is selected from hydrogen, halogen, and $C_1$-$C_6$-alkoxy; and
$R^6$ is hydrogen or halogen.

12. The compound of formula (I) according to claim 11, or a pharmaceutically acceptable salt thereof, wherein:
$R^4$ is selected from fluoro, (methyl)$_2$N—, and $CF_3$;
$R^5$ is selected from hydrogen, fluoro, and methoxy; and
$R^6$ is hydrogen or fluoro.

13. The compound of formula (I) according to claim 1, or a pharmaceutically acceptable salt thereof, wherein A is a 6- to 14-membered heteroaryl.

14. The compound of formula (I) according to claim 13, or a pharmaceutically acceptable salt thereof, wherein A is a 6- to 9-membered heteroaryl.

15. The compound of formula (I) according to claim 11, or a pharmaceutically acceptable salt thereof, wherein A is selected from pyridyl, indolyl, indazolyl, pyrimidinyl, and 2,3-dihydro-1,4-benzodioxinyl.

16. The compound of formula (I) according to claim 12, or a pharmaceutically acceptable salt thereof, wherein A is selected from pyridyl, indolyl, and indazolyl.

17. The compound of formula (I) according to claim 1, or a pharmaceutically acceptable salt thereof, wherein:
$R^4$ is selected from hydrogen, halogen, $C_1$-$C_6$-alkyl, $C_1$-$C_6$-alkoxy, $C_1$-$C_6$-alkyl-NH—, ($C_1$-$C_6$-alkyl)$_2$N—, and halo-$C_1$-$C_6$-alkyl;
$R^5$ is hydrogen, $C_1$-$C_6$-alkyl, $C_1$-$C_6$-alkoxy, halogen, ($C_1$-$C_6$-alkyl)$_2$N—; and
$R^6$ is hydrogen, halogen.

18. The compound of formula (I) according to claim 1, or a pharmaceutically acceptable salt thereof, wherein:
$R^1$ is selected from:
(i) a group

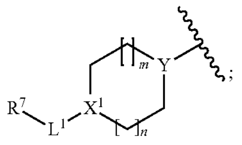

(ii) a group

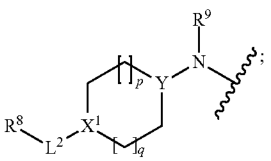

and (iii) a group

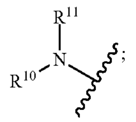

$R^2$ is halogen or $C_1$-$C_6$-alkyl;

$R^3$ is $C_1$-$C_6$-alkyl;

$R^4$ is selected from hydrogen, halogen, $C_1$-$C_6$-alkyl, $C_1$-$C_6$-alkoxy, $C_1$-$C_6$-alkyl-NH—, $(C_1$-$C_6$-alkyl$)_2$N—, and halo-$C_1$-$C_6$-alkyl;

$R^5$ is selected from hydrogen, $C_1$-$C_6$-alkyl, $C_1$-$C_6$-alkoxy, halogen, and $(C_1$-$C_6$-alkyl$)_2$N—;

$R^6$ is hydrogen or halogen $R^7$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, and a group

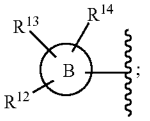

$R^8$ is selected from $(C_1$-$C_6$-alkyl$)_2$N—$C_1$-$C_6$-alkyl-, $(C_1$-$C_6$-alkyl$)_3N^+$—$C_1$-$C_6$-alkyl-, $(C_1$-$C_6$-alkyl$)_3N^+$—$C_1$-$C_6$-alkoxy-$C_1$-$C_6$-alkyl, and a group

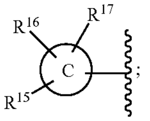

$R^9$ and $R^{11}$ are both hydrogen;

$R^{10}$ is selected from amino-$C_1$-$C_6$-alkyl and $(C_1$-$C_6$-alkyl$)_3$ $N^+$—$C_1$-$C_6$-alkyl-;

$R^{12}$ is selected from hydrogen, hydroxy, amino-$C_1$-$C_6$-alkyl, and $(C_1$-$C_6$-alkyl$)_3N^+$—$C_1$-$C_6$-alkyl-;

$R^{13}$, $R^{14}$, $R^{16}$, and $R^{17}$ are each independently selected from hydrogen and $C_1$-$C_6$-alkyl;

$R^{15}$ is hydroxy;

A is a 6- to 9-membered heteroaryl;

B is selected from 3- to 14-membered heterocycloalkyl and $C_3$-$C_{10}$-cycloalkyl;

C is 3- to 14-membered heterocycloalkyl;

$L^1$ is selected from carbonyl, —$C_1$-$C_6$-alkyl-C(O)—, —NH—C(O)—, and—C(O)—NH—;

$L^2$ is selected from carbonyl and—C(O)—NH—;

$X^1$ and $X^2$ are each independently selected from N and CH;

Y is N;

m and n are both 1; and p and q are both 0;

or p and q are both 1.

19. The compound of formula (I) according to claim 18, or a pharmaceutically acceptable salt thereof, wherein:

$R^1$ is a group

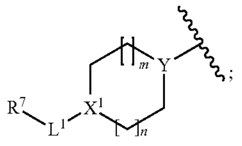

$R^2$ is halogen;

$R^3$ is $C_1$-$C_6$-alkyl;

$R^4$ is selected from halogen, $(C_1$-$C_6$-alkyl$)_2$N—, and halo-$C_1$-$C_6$-alkyl;

$R^5$ is selected from hydrogen, halogen, and $C_1$-$C_6$-alkoxy;

$R^6$ is hydrogen or halogen;

$R^7$ is a group

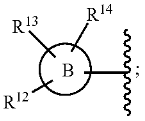

$R^{12}$ is hydrogen or hydroxy;

$R^{13}$ and $R^{14}$ are both hydrogen;

A is a 6- to 9-membered heteroaryl;

B is a 3- to 14-membered heterocycloalkyl;

$L^1$ is carbonyl or —$C_1$-$C_6$-alkyl-C(O)—;

$X^1$ and Y are both N; and m and n are both 1.

20. The compound of formula (I) according to claim 19, or a pharmaceutically acceptable salt thereof, wherein:

$R^1$ is a group

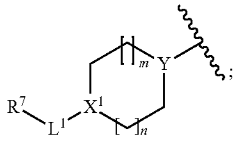

$R^2$ is chloro;

$R^3$ is methyl;

$R^4$ is selected from fluoro, $(methyl)_2$N—, and $CF_3$;

$R^5$ is selected from hydrogen, fluoro, and methoxy;

$R^6$ is hydrogen or fluoro;

$R^7$ is a group

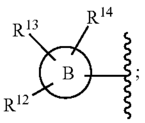

$R^{12}$ is hydrogen or hydroxy;

$R^{13}$ and $R^{14}$ are both hydrogen;

A is selected from pyridyl, indolyl, and indazolyl;

B is piperidine or pyrrolidine;

$L^1$ is carbonyl or —$CH_2$—C(O)—;

$X^1$ and Y are both N; and m and n are both 1.

21. The compound of formula (I) according to claim 1, or a pharmaceutically acceptable salt thereof, wherein said compound of formula (I) is selected from the group consisting of:

N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide;

N-[3-chloro-4-[4-[2-[(3S)-pyrrolidin-3-yl]acetyl]piperazine-1-carbonyl]phenyl]-5-(6-fluoro-3-methyl-1H-indazol-5-yl)-1-methyl-imidazole-2-carboxamide;

N-[3-chloro-4-[4-[2-[(3S)-pyrrolidin-3-yl]acetyl]piperazine-1-carbonyl]phenyl]-1-methyl-5-[3-(trifluoromethyl)-1H-indazol-5-yl]imidazole-2-carboxamide;

N-[3-chloro-4-[4-[2-[(3S)-pyrrolidin-3-yl]acetyl]piperazine-1-carbonyl]phenyl]-5-(7-methoxy-1H-indol-4-yl)-1-methyl-imidazole-2-carboxamide;

N-[3-chloro-4-[4-(piperidine-4-carbonyl) piperazine-1-carbonyl]phenyl]-5-(2,6-dichloro-3-pyridyl)-1-methyl-imidazole-2-carboxamide;

N-[3-chloro-4-[4-(piperidine-4-carbonyl) piperazine-1-carbonyl]phenyl]-5-[6-(dimethylamino)-2-(trifluoromethyl)-3-pyridyl]-1-methyl-imidazole-2-carboxamide;

N-[3-chloro-4-[4-(piperidine-4-carbonyl) piperazine-1-carbonyl]phenyl]-5-(2,6-dimethoxy-3-pyridyl)-1-methyl-imidazole-2-carboxamide;

5-(5-chloro-2-methoxy-4-pyridyl)-N-[3-chloro-4-[4-(piperidine-4-carbonyl) piperazine-1-carbonyl]phenyl]-1-methyl-imidazole-2-carboxamide;

N-[3-chloro-4-[4-[2-[(3S)-pyrrolidin-3-yl]acetyl]piperazine-1-carbonyl]phenyl]-5-[2-(dimethylamino)-4-(trifluoromethyl)pyrimidin-5-yl]-1-methyl-imidazole-2-carboxamide;

N-[3-chloro-4-[4-(piperidine-4-carbonyl) piperazine-1-carbonyl]phenyl]-5-[2-methoxy-4-(trifluoromethyl)pyrimidin-5-yl]-1-methyl-imidazole-2-carboxamide;

5-(5-chloro-1H-indol-4-yl)-N-[3-chloro-4-[4-[2-[(3S)-pyrrolidin-3-yl]acetyl]piperazine-1-carbonyl]phenyl]-1-methyl-imidazole-2-carboxamide;

N-[3-chloro-4-[4-(piperidine-4-carbonyl) piperazine-1-carbonyl]phenyl]-5-(1H-indol-4-yl)-1-methyl-imidazole-2-carboxamide;

N-[3-chloro-4-[4-(piperidine-4-carbonyl) piperazine-1-carbonyl]phenyl]-1-methyl-5-(1-methylindol-4-yl) imidazole-2-carboxamide;

N-[3-chloro-4-[4-[2-[(3S)-pyrrolidin-3-yl]acetyl]piperazine-1-carbonyl]phenyl]-5-[6-methoxy-2-(trifluoromethyl)-3-pyridyl]-1-methyl-imidazole-2-carboxamide;

5-(4-chloro-6-methoxy-3-pyridyl)-N-[3-chloro-4-[4-(piperidine-4-carbonyl) piperazine-1-carbonyl]phenyl]-1-methyl-imidazole-2-carboxamide;

N-[3-chloro-4-[4-(piperidine-4-carbonyl) piperazine-1-carbonyl]phenyl]-5-[6-methoxy-2-(trifluoromethyl)-3-pyridyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[6-methoxy-2-(trifluoromethyl)-3-pyridyl]-1-methyl-imidazole-2-carboxamide;

N-[4-[4-[(1R,5S)-3-azabicyclo[3.1.0]hexane-6-carbonyl] piperazine-1-carbonyl]-3-chloro-phenyl]-5-[6-methoxy-2-(trifluoromethyl)-3-pyridyl]-1-methyl-imidazole-2-carboxamide;

N-[3-chloro-4-[4-(piperidine-4-carbonyl) piperazine-1-carbonyl]phenyl]-5-[2-(difluoromethyl)-6-methoxy-3-pyridyl]-1-methyl-imidazole-2-carboxamide;

N-[3-chloro-4-[4-(piperidine-4-carbonyl) piperazine-1-carbonyl]phenyl]-5-(2,3-dihydro-1,4-benzodioxin-6-yl)-1-methyl-imidazole-2-carboxamide;

N-[4-(6-aminohexylcarbamoyl)-3-chloro-phenyl]-5-[6-(dimethylamino)-2,5-difluoro-3-pyridyl]-1-methyl-imidazole-2-carboxamide;

N-[3-chloro-4-[4-[2-(dimethylamino)acetyl]piperazine-1-carbonyl]phenyl]-5-[6-(dimethylamino)-2,5-difluoro-3-pyridyl]-1-methyl-imidazole-2-carboxamide;

N-[4-[4-[2-(dimethylamino)acetyl]piperazine-1-carbonyl]-3-methyl-phenyl]-5-[6-(dimethylamino)-2,5-difluoro-3-pyridyl]-1-methyl-imidazole-2-carboxamide;

N-[3-chloro-4-[3-[2-(dimethylamino)acetyl]amino]cyclobutyl]carbamoyl]phenyl]-5-[6-(dimethylamino)-2,5-difluoro-3-pyridyl]-1-methyl-imidazole-2-carboxamide;

N-[3-chloro-4-[4-[2-(dimethylamino)acetyl]amino]piperidine-1-carbonyl]phenyl]-5-[6-(dimethylamino)-2,5-difluoro-3-pyridyl]-1-methyl-imidazole-2-carboxamide;

[2-[4-[2-chloro-4-[[5-[6-(dimethylamino)-2,5-difluoro-3-pyridyl]-1-methyl-imidazole-2-carbonyl]amino]benzoyl]piperazin-1-yl]-2-oxo-ethyl]-trimethyl-ammonium;

[2-[4-[4-[5-[6-(dimethylamino)-2,5-difluoro-3-pyridyl]-1-methyl-imidazole-2-carbonyl]amino]-2-methyl-benzoyl]piperazin-1-yl]-2-oxo-ethyl]-trimethyl-ammonium;

6-[[2-chloro-4-[[5-[6-(dimethylamino)-2,5-difluoro-3-pyridyl]-1-methyl-imidazole-2-carbonyl]amino]benzoyl]amino]hexyl-trimethyl-ammonium;

N-[3-chloro-4-[4-(1,1-dimethylpiperidin-1-ium-4-carbonyl) piperazine-1-carbonyl]phenyl]-5-[6-(dimethylamino)-2,5-difluoro-3-pyridyl]-1-methyl-imidazole-2-carboxamide;

N-[3-chloro-4-[4-(1,1-dimethylpyrrolidin-1-ium-3-carbonyl) piperazine-1-carbonyl]phenyl]-5-[6-(dimethylamino)-2,5-difluoro-3-pyridyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[6-(dimethylamino)-2,5-difluoro-3-pyridyl]-1-methyl-imidazole-2-carboxamide;

N-[3-chloro-4-[4-[2-(1,1-dimethylpiperidin-1-ium-4-yl) acetyl]piperazine-1-carbonyl]phenyl]-5-[6-(dimethylamino)-2,5-difluoro-3-pyridyl]-1-methyl-imidazole-2-carboxamide;

[2-[3-[[2-chloro-4-[5-[6-(dimethylamino)-2,5-difluoro-3-pyridyl]-1-methyl-imidazole-2-carbonyl]amino]benzoyl]amino]cyclobutyl]amino]-2-oxo-ethyl]-trimethylammonium;

[2-[1-[2-chloro-4-[5-[6-(dimethylamino)-2,5-difluoro-3-pyridyl]-1-methyl-imidazole-2-carbonyl]amino]benzoyl]-4-piperidyl]amino]-2-oxo-ethyl]-trimethyl-ammonium;

2-[3-[4-[[2-chloro-4-[5-[6-(dimethylamino)-2,5-difluoro-3-pyridyl]-1-methyl-imidazole-2-carbonyl]amino]benzoyl]amino]-1-piperidyl]-3-oxo-propoxy]ethyl-trimethyl-ammonium;

[3-[4-[2-chloro-4-[[5-[6-(dimethylamino)-2,5-difluoro-3-pyridyl]-1-methyl-imidazole-2-carbonyl]amino]benzoyl]piperazine-1-carbonyl]cyclobutyl]methyl-trimethyl-ammonium;

N-[3-chloro-4-[1-[(2S,4R)-4-hydroxy-1,1-dimethyl-pyrrolidin-1-ium-2-carbonyl]-4-piperidyl]carbamoyl]phenyl]-5-[6-(dimethylamino)-2,5-difluoro-3-pyridyl]-1-methyl-imidazole-2-carboxamide;

1-[2-chloro-4-[5-[6-(dimethylamino)-2,5-difluoro-3-pyridyl]-1-methyl-imidazole-2-carbonyl]amino]benzoyl]-N-(1,1-dimethylpyrrolidin-1-ium-3-yl) piperidine-4-carboxamide;

N-[3-chloro-4-[4-(piperidine-4-carbonyl) piperazine-1-carbonyl]phenyl]-5-[2,5-difluoro-6-(methylamino)-3-pyridyl]-1-methyl-imidazole-2-carboxamide;

N-[3-chloro-4-[4-(piperidine-4-carbonyl) piperazine-1-carbonyl]phenyl]-5-[6-(dimethylamino)-2,5-difluoro-3-pyridyl]-1-methyl-imidazole-2-carboxamide;

N-[3-chloro-4-[4-(piperidine-4-carbonyl) piperazine-1-carbonyl]phenyl]-5-[6-(dimethylamino)-2-fluoro-3-pyridyl]-1-methyl-imidazole-2-carboxamide;

N-[3-chloro-4-[4-(piperidine-4-carbonyl) piperazine-1-carbonyl]phenyl]-5-[6-(dimethylamino)-2-methyl-3-pyridyl]-1-methyl-imidazole-2-carboxamide;

5-[2-chloro-6-(dimethylamino)-3-pyridyl]-N-[3-chloro-4-[4-(piperidine-4-carbonyl) piperazine-1-carbonyl]phenyl]-1-methyl-imidazole-2-carboxamide;

N-[3-chloro-4-[4-(4-hydroxypiperidine-4-carbonyl) piperazine-1-carbonyl]phenyl]-5-[6-(dimethylamino)-2,5-difluoro-3-pyridyl]-1-methyl-imidazole-2-carboxamide;

N-[3-chloro-4-[4-[2-[(3S)-pyrrolidin-3-yl]acetyl]piperazine-1-carbonyl]phenyl]-5-[6-(dimethylamino)-2,5-difluoro-3-pyridyl]-1-methyl-imidazole-2-carboxamide;

N-[3-chloro-4-[4-[2-(4-hydroxy-4-piperidyl) acetyl]piperazine-1-carbonyl]phenyl]-5-[6-(dimethylamino)-2,5-difluoro-3-pyridyl]-1-methyl-imidazole-2-carboxamide;

N-[3-chloro-4-[4-(pyrrolidine-3-carbonyl) piperazine-1-carbonyl]phenyl]-5-[6-(dimethylamino)-2,5-difluoro-3-pyridyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[6-(dimethylamino)-2,5-difluoro-3-pyridyl]-1-methyl-imidazole-2-carboxamide;

N-[3-chloro-4-[4-[2-(4-piperidyl) acetyl]piperazine-1-carbonyl]phenyl]-5-[6-(dimethylamino)-2,5-difluoro-3-pyridyl]-1-methyl-imidazole-2-carboxamide;

N-[4-[4-[3-(aminomethyl)cyclobutanecarbonyl]piperazine-1-carbonyl]-3-chloro-phenyl]-5-[6-(dimethylamino)-2,5-difluoro-3-pyridyl]-1-methyl-imidazole-2-carboxamide;

N-[4-[1-[3-(2-aminoethoxy) propanoyl]-4-piperidyl]carbamoyl]-3-chloro-phenyl]-5-[6-(dimethylamino)-2,5-difluoro-3-pyridyl]-1-methyl-imidazole-2-carboxamide;

N-[3-chloro-4-[1-[(2S,4R)-4-hydroxypyrrolidine-2-carbonyl]-4-piperidyl]carbamoyl]phenyl]-5-[6-(dimethylamino)-2,5-difluoro-3-pyridyl]-1-methyl-imidazole-2-carboxamide; and 1-[2-chloro-4-[[5-[6-(dimethylamino)-2,5-difluoro-3-pyridyl]-1-methyl-imidazole-2-carbonyl]amino]benzoyl]-N-pyrrolidin-3-yl-piperidine-4-carboxamide.

22. The compound of formula (I) according to claim 21, or a pharmaceutically acceptable salt thereof, wherein said compound of formula (I) is selected from the group consisting of:

N-[3-chloro-4-[4-[2-[(3S)-pyrrolidin-3-yl]acetyl]piperazine-1-carbonyl]phenyl]-5-(5-fluoro-1H-indol-4-yl)-1-methyl-imidazole-2-carboxamide;

N-[3-chloro-4-[4-[2-[(3S)-pyrrolidin-3-yl]acetyl]piperazine-1-carbonyl]phenyl]-1-methyl-5-[3-(trifluoromethyl)-1H-indazol-5-yl]imidazole-2-carboxamide;

N-[3-chloro-4-[4-[2-[(3S)-pyrrolidin-3-yl]acetyl]piperazine-1-carbonyl]phenyl]-5-[6-methoxy-2-(trifluoromethyl)-3-pyridyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[6-methoxy-2-(trifluoromethyl)-3-pyridyl]-1-methyl-imidazole-2-carboxamide;

N-[3-chloro-4-[4-(piperidine-4-carbonyl) piperazine-1-carbonyl]phenyl]-5-[6-(dimethylamino)-2,5-difluoro-3-pyridyl]-1-methyl-imidazole-2-carboxamide; and N-[3-chloro-4-[4-[2-[(3S)-pyrrolidin-3-yl]acetyl]piperazine-1-carbonyl]phenyl]-5-[6-(dimethylamino)-2,5-difluoro-3-pyridyl]-1-methyl-imidazole-2-carboxamide.

23. A pharmaceutical composition comprising a compound of formula (I) according to claim 1, or a pharmaceutically acceptable salt thereof, and a therapeutically inert carrier.

24. A method for treating infections and the resulting diseases caused by Gram-negative bacteria, the method comprising administering a pharmaceutically effective amount of a compound of formula (I) according to claim 1, or a pharmaceutically acceptable salt thereof, to a patient in need thereof.

25. The method according to claim 24, wherein the Gram-negative bacteria are selected from *Enterococcus faecium, Staphylococcus aureus, Klebsiella pneumoniae, Acinetobacter baumannii, Pseudomonas aeruginosa, Enterobacter* species and *E. coli*, or a combination thereof.

* * * * *